United States Patent
Kelly et al.

(10) Patent No.: US 11,028,061 B2
(45) Date of Patent: Jun. 8, 2021

(54) MODULATORS OF MYOCYTE LIPID ACCUMULATION AND INSULIN RESISTANCE AND METHODS OF USE THEREOF

(71) Applicant: Sanford Burnham Prebys Medical Discovery Institute, La Jolla, CA (US)

(72) Inventors: Daniel Kelly, La Jolla, CA (US); Richard Vega, La Jolla, CA (US); Hampton Sessions, La Jolla, CA (US); Teresa Leone, La Jolla, CA (US); Byungyong Ahn, La Jolla, CA (US); Satyamaheshwar Peddibhotla, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 15/748,515

(22) PCT Filed: Jul. 27, 2016

(86) PCT No.: PCT/US2016/044269
§ 371 (c)(1),
(2) Date: Jan. 29, 2018

(87) PCT Pub. No.: WO2017/019772
PCT Pub. Date: Feb. 2, 2017

(65) Prior Publication Data
US 2018/0222874 A1    Aug. 9, 2018

Related U.S. Application Data

(60) Provisional application No. 62/197,534, filed on Jul. 27, 2015.

(51) Int. Cl.
| | |
|---|---|
| C07D 277/46 | (2006.01) |
| A61K 31/426 | (2006.01) |
| A61K 31/5377 | (2006.01) |
| A61K 31/454 | (2006.01) |
| A61K 31/496 | (2006.01) |
| A61K 31/541 | (2006.01) |
| C07D 417/12 | (2006.01) |
| A61K 31/4439 | (2006.01) |
| C07D 417/04 | (2006.01) |
| C07D 277/82 | (2006.01) |
| A61K 45/06 | (2006.01) |
| A61P 3/10 | (2006.01) |
| A61P 3/04 | (2006.01) |
| A61K 31/5375 | (2006.01) |
| A61K 31/428 | (2006.01) |
| C07D 295/185 | (2006.01) |

(52) U.S. Cl.
CPC .......... *C07D 277/46* (2013.01); *A61K 31/426* (2013.01); *A61K 31/428* (2013.01); *A61K 31/4439* (2013.01); *A61K 31/454* (2013.01); *A61K 31/496* (2013.01); *A61K 31/5375* (2013.01); *A61K 31/5377* (2013.01); *A61K 31/541* (2013.01); *A61K 45/06* (2013.01); *A61P 3/04* (2018.01); *A61P 3/10* (2018.01); *C07D 277/82* (2013.01); *C07D 295/185* (2013.01); *C07D 417/04* (2013.01); *C07D 417/12* (2013.01)

(58) Field of Classification Search
CPC ............... C07D 277/46; C07D 277/82; C07D 295/185; C07D 417/04; C07D 417/12; A61P 3/04; A61P 3/10; A61K 31/426; A61K 31/428; A61K 31/4439; A61K 31/454; A61K 31/496; A61K 31/5375; A61K 31/5377; A61K 31/541; A61K 45/06
USPC ........................................................ 548/185
See application file for complete search history.

(56) References Cited

U.S. PATENT DOCUMENTS

2008/0076771 A1* 3/2008 Reiter ...................... A61P 7/00
514/245

OTHER PUBLICATIONS

AdamsMito J. et al., "Ceramide Content is Increased in Skeletal Muscle From Obese Insulin-Resistant Humans", Diabetes, 53: 25-31 (2004).
Amati, Francesca et al., "Skeletal Muscle Triglycerides, Diacylglycerols, and Ceramides in Insulin Resistance", Diabetes, 60: 2588-2597 (2011).

(Continued)

*Primary Examiner* — Kristin A Vajda
(74) *Attorney, Agent, or Firm* — Kathleen D. Rigaut; Howson & Howson, LLP

(57) ABSTRACT

Formulations and methods for reducing blood glucose and/or increasing insulin signaling in a subject have been developed. The formulations include SBI-477 and compounds based on SBI-477 i.e., SBI-477 analogs (collectively, SBI-477 compounds) and/or Mondo family inhibitors, in an effective amount to inhibit intracellular lipid accumulation and/or increase cellular glucose uptake when compared to levels in a control subject not administered the composition. Also disclosed are methods of reducing intracellular lipid accumulation and/or increase glucose uptake in a subject in need thereof. The method includes administering to the subject an effective amount of SBI-477 compounds and/or Mondo family inhibitor to reducing intracellular lipid accumulation and/or increase glucose uptake in the subject. Also disclosed are method for treating one or more Myc-driven cancers, including neuroblastoma, lung squamous cell carcinoma/lung adenocarcinoma, liver hepatocellular carcinoma, colon adenocarcinoma, acute myeloid leukemia, and breast invasive carcinoma.

7 Claims, 17 Drawing Sheets
Specification includes a Sequence Listing.

(56) References Cited

OTHER PUBLICATIONS

Anderson et al., "Mitochondrial H202 emission and cellular redox state link excess fat intake to insulin resistance to both rodents and humans", The Journal of Clinical Investigation, 119(3): 573-581 (2009).

Bergman, B.C. et al., "Localisation and composition of skeletal muscle diacylglycerol predicts insulin resistance in humans", Diabetologia, 55(4): 1140-1150 (2012).

Billin, A. et al., "MondoA, a Novel Basic Helix-Loop-Helix-Leucine Zipper Transcriptional Activator that Constitutes a Positive Branch of a Max-Like Network", Molecular and Cellular Biology, 20(23): 8845-8854 (2000).

Bricambert et al., "Salt-inducible kinase 2 links transcriptional coactivator p300 phosphorylation to the prevention of ChREBP-dependent hepatic steatosis in mice", The Journal of Clinical Investigation, 120(12): 4316-4331 (2010).

Carroll, P. et al., "Deregulated Myc Requires MondoA/Mix for Metabolic Reprogramming and Tumorigenesis", Cancer Cell, 27(2): 271-285 (2015).

Cha-Molstad et al., "Glucose-stimulated Expression of Txnip is Mediated by Carbohydrate Response element-binding Protein, p300, and Histone H4 Acetylation in Pancreatic Beta Cells", The Journal of Biological Chemistry, 284 (25): 16898-26905 (2009).

Chavez, J. et al., A Role for Ceramide, but Not Diacylglycerol, in the Antagonism of Insulin Signal Transduction by Saturated fatty Acids, The Journal of Biological Chemistry, 278(12): 10297-10303 (2003).

Chiu, Y. et al., "RNAi in Human Cells: Basic Structural and Functional Features of Small Interfering RNA", Molecular Cell, 10: 549-561 (2002).

Coen, P. et al., "Role of intramyocellular lipids in human health", Trends, Endocrinol Metab., 23(8): 391-398 (2012).

Dentin, B. et al., "Hepatic Glucokinase is Required for the Synergistic Action of ChREBP and SREBP-Ic on Glycolytic and Lipogenic Gene Expression", The Journal of Biological Chemistry, 279(19): 20314-20326 (2004).

Goodpaster, B. et al., "Skeletal Muscle Lipid Content and Insulin Resistance: Evidence for a Paradox in Endurance-Trained Athletes", The Journal of Clinical Endocrinology & Metabolism, 86(12): 5755-5761 (2001).

Guinez, Celine et al., "O-GlcNcylation Increases ChREBP Protein Content and Transcriptional Activity in the Liver", Diabetes, 66, 1399-1413 (2011).

Hendry, P. et al., Redesigned and chemically-modified hammerhead ribozymes with improved activity and serum stability, BMC Chemical Biology, 4: 472 (2004).

Iizuka, K. et al., Deficiency of carbohydrate activated transcription factor ChREBP prevents obesity and improved plasma glucose control in leptin-deficient (ob/ob) mice, Am. J. Physiol. Endocrinol. Metab., 291: E364-E364 (2006).

Kaadige, M. et al., "Glutamine-dependent anapleurosis dictates glucose uptake and cell growth by regulating MondA transcriptional activity", PNAS, 106(35): 14878-14883 (2009).

Kabashima, T. et al., "Xylulose 5-phosphate mediates glucose-induced lipogenesis by xylulose 5-phosphate-activated protein phosphatase in rat liver", PNAS, 100(9): 5107-5112 (2003).

Kawaguchi, T. et al., "Glucose and cAMP regulate the L-type pyruvate kinase gene by phosphorylation/dephosphorytlation of the carbohydrate response element binding protein", PNAS, 98(24): 137210-13715 (2001).

Koves, T. et al., "Mitochondrial Overload and Incomplete Fatty Acid Oxidation Contribute to Skeletal Muscle Insulin Resistance", Cell Metabolism, 7: 45-56 (2008).

Krssak, M. et al., "Intramyocellular lipid concentrations are correlated with insulin sensitivity in humans: a 1H NMR spectroscopy study", Diabetologia, 42: 113-116 (1999).

Kumashiro, N. et al., "Cellular mechanism of insulin resistance in nonalcoholic fatty liver disease", PNAS, 108(39): 16381-16385 (2011).

Li, B. et al., "Using siRNA in prophylactic and therapeutic regimens against SARS coronavirus in Rhesus macaque", Nature Medicine, 11(9): 944 (2005).

Listenberger, L. et al., "Triglyceride accumulation protects against fatty acid-reduced lipotoxicity", PNAS, 100(6): 3077-3082 (2003).

Liu, L. et al., "DGAT Expression Increases Heart Triglyceride Content but Ameliorates Lipotoxicity", The Journal of Biological Chemistry, 284(52): 36312-36323 (2009).

McManus, M. et al., "Gene silencing using micro-RNA designed hairpins", RNA, 8: 842-850 (2002).

Mitra, R. et al., "The Transcriptional Coactivators, PGC-1 and B, Cooperate to Maintain Cardiac Mitochondrial Function During the Early Stages of Insulin Resistance", J. Mol. Cell Cardiol., 52(32): 701-710 (2012).

Montell, E. et al., "DAG accumulation from saturate fatty acids desensitizes insulin stimulation of glucose uptake in muscle cells", Am. J. Physiol. Endocrinol. Metals, 280: E229-E237 (2001).

Niman, H. et al., "Generation of protein-reactive antoibodies by short peptides is an event of high frequency: Implications for the structural basis of immune recognition", Proc. Natl. Acad. Sci. USA, 890: 4949-4953 (1983).

Oslowski, C. et al., "Thioredoxin-interacting protein mediates ER stress-induced B cell death through initiation of the inflammasome", Cell Metab., 16(2): 265-273 (2012).

Paddison, P. et al., "Short hairpin RNAs (shRNAs) induce sequence-specific silencing in mammalian cells", Genes & Development, 16: 948-958 (2002).

Pan, D. et al., "Skeletal Muscle Membrane Lipid Composition is related to Adiposity and Insulin Action", J. Clin. Invest., 96: 2802-2808 (1995).

Parikh, H. et al., "TXNIP Regulates Peripheral glucose Metabolism in Humans", PLoS Medicine, 4(5): e158 (2007).

Petersen, K. et al., "Impaired Mitochondrial Activity in the Insulin-Resistant Offspring of Patients with Type 2 Diabetes", N. Engl. J. Med., 350(7): 664-671 (2004).

Petersen, H. et al., "Glucose Controls Nuclear Accumulation, Promoter Binding, and Transcriptional Activity of the MondoA-M1x Heterodimer", Molecular and Cellular Biology, 30(12): 2887-2895 (2010).

Petrie, J. et al., "Glucose Induces Protein Targeting to Glycogen in Hepatocytes by Fructose 2,6-Biphosphate-Mediated Recruitment of MondoA to the Promoter", Molecular and Cellular Biology, 33(4): 725-738 (2013).

Sakiyama, H. et al., "Regulation of Nuclear Import/Export of Carbohydrate Response Element-Binding Protein (ChREBP)", The Journal of Biological Chemistry, 283(36): 24899-24908 (2008).

Samuel, V. et al., "Mechanism of Hepatic Insulin Resistance in Non-Alcoholic Fatty Liver Disease", The Journal of Biological Chemistry, 279(31): 32345-32353 (2004).

Sharp, P. et al., "RNA interference—2001", Genes & Development, 15: 485-490 (2001).

Skovbro, M. et al., "Human skeletal muscle ceramide content is not a major factor in muscle insulin sensitivity", Diabetologia, 51: 1253-1260 (2008).

Sloan, E. et al., "Myc, Mondo and Metabolism", Genes & Cancer, 1(6): 587-596 (2010).

Stoltzman, C. et al., "Glucose sensing by MondoA: M1X complexes: A role for hexokinases and direct regulation of thioredoxin-interacting protein expression", PNAS, 105(19): 6942-6917 (2008).

Sui, G. et al., "A DNA vector-based RNAi technology to suppress gene expression in mammalian cells", PNAS, 99(8): 5515-5520 (2002).

Szendroedi, J. et al., "Role of diacylglycerol activation of PKC0 in lipid-induced muscle insulin resistance in humans", PNAS, 111(26): 9597-9602 (2014).

Yoshihara, E. et al., "Disruption of TBP-2 ameliorates insulin sensitivity and secretion without affecting obesity", Nature Communications, 1: 127 (2010).

Yu, J. et al., "RNA interference by expression of short-interfering RNAs and hairpin RNAs in mammalian cells", PNAS, 99(9): 6047-6052 (2002).

(56) References Cited

OTHER PUBLICATIONS

Yu, C. et al., "Mechanism by Which Fatty Acids Inhibit Activation of Insulin Receptor Substrate-1 (IRS-1)-associated Phosphatidylinositol 3-Kinase Activity in Muscle", The Journal of Biological Chemistry, 277(52): 50230-50236 (2002).

Zheng, Y. et al., "Both Natural and Designed Micro RNAs Can Inhibit the Expression of cognate mRNAs When Expressed in Human Cells", Molecular Cell, 9: 1327-1333 (2002).

* cited by examiner

*P<0.05 vs. Insulin-vehicle
§SBI-477

MODULATORS OF MYOCYTE LIPID ACCUMULATION AND INSULIN RESISTANCE AND METHODS OF USE THEREOF

CROSS-REFERENCE TO RELATED APPLICATIONS

This application is a 371 application of PCT/US2016/044269, filed Jul. 27, 2016, which claims priority to and benefit of U.S. Provisional Application No. 62/197,534, filed Jul. 27, 2015. Application No. 62/197,534, filed Jul. 27, 2015, is hereby incorporated herein by reference in its entirety.

STATEMENT REGARDING FEDERALLY SPONSORED RESEARCH

This invention was made with Government support under Grant Nos. RO1 DK045416, R24 DK092781, and R24 DK084969 awarded by the National Institutes of Health. The Government has certain rights in the invention.

REFERENCE TO SEQUENCE LISTING

The Sequence Listing submitted on Jul. 27, 2016 as a text file named "SBMRI_14-022 PCT_ST25," created on Jul. 26, 2016, and having a size of 13,695 bytes is hereby incorporated by reference.

FIELD OF THE INVENTION

The disclosed invention is generally in the field of compositions and methods of reducing one or more symptoms associated with insulin resistance.

BACKGROUND OF THE INVENTION

The rising prevalence of obesity is driving an alarming increase in type 2 diabetes, a global health threat. Co-morbidities associated with obesity include insulin resistance, fatty liver disease (NAFLD/NASH) and lipotoxic cardiomyopathy. The development of obesity-related diabetes represents a final common pathogenic pathway that further contributes to the comorbid diseases. Accordingly, delineation of the mechanisms involved in the development of insulin resistance is a critical step towards the identification of new therapeutic targets aimed at the early treatment of this progressive feed-forward disease process.

The development of insulin resistance is strongly associated with accumulation of intracellular lipid in tissues outside of adipose including skeletal muscle, liver, and heart. In obese humans, intramyocellular lipid (IMCL) is negatively correlated with whole-body insulin sensitivity (Pan, et al., *Diabetes.* 1997; 46(6):983-988; Krssak, et al., *Diabetologia.* 1999; 42(1):113-116 and Goodpaster et al., *Metabolism.* 2000; 49(4):467-472). The skeletal myocyte imports fatty acids (FA) into the cell from circulating free fatty acid (FAs) or lipoprotein particles, such as very low density lipoprotein (VLDL), to support energy production. Once transported into the cell, FAs are oxidized for ATP production, used to build membranes, or stored as triglyceride. However, excessive skeletal myocyte lipid delivery, such as occurs in the obese state, leads to expansion of IMCL. Increased import of fatty acids is thought to initially trigger an adaptive response within the skeletal muscle to increase capacity for mitochondrial fatty acid oxidation (Mitra, et al. *Mol Cell Cardiol.* 2012; 52(3):701-710). In the long-term, however, increased delivery of fatty acids can exceed mitochondrial oxidative capacity setting the stage for a "vicious cycle" of cellular lipotoxicity, leading to insulin resistance. In support of this notion, some studies have shown that mitochondrial oxidative capacity is reduced in insulin resistant diabetic subjects (Petersen, et al., *New Engl J Med.* 2004; 350(7):664-671; Schrauwen-Hinderling, et al., *Diabetologia.* 2007; 50(1):113-120 and Phielix, et al., *Diabetologia.* 2007; 50(1):113-120).

The mechanistic links between IMCL and the development of insulin resistance are poorly understood. The results of studies to date suggest that the lipid storage depot per se is likely not a culprit in the genesis of cellular "lipotoxicity" and insulin resistance. Indeed, some studies have suggested that capacity to store lipid within the cell serves a protective function (Listenberger, et al., *Proc Natl Acad Sci USA.* 2003; 100(6):3077-3082; Liu, et al., *J Biol Chem.* 2009; 284(52): 36312-36323). Rather, generation and accumulation of lipid intermediates have been proposed to alter insulin stimulated glucose uptake (Samuel, et al., *Biol Chem.* 2004; 279(31): 32345-32353; and Bosma, et al. *Prog Lipid Res.* 2012; 51(1):36-49). For example, lipid-derived diacylglycerol (DAG) species have been shown to activate protein kinase C-$\epsilon$ and $\theta$ isoforms to phosphorylate the insulin receptor substrate-1 (IRS-1), blocking the actions of the insulin receptor (Idris, et al., *Ann NY Acad Sci.* 2002; 967:176-182; Kumashiro et al., *Proc Natl Acad Sci USA.* 2011; 108(39): 16381-16385). Ceramides and reactive oxygen species have also been shown to inhibit insulin signaling in certain contexts (Chavez, et al., *J Biol Chem.* 2003; 278(12):10297-10303; Anderson, et al., *J Clin Invest.* 2009; 119(3):573-581). In addition, intermediates of incomplete fatty acid oxidation have been implicated in insulin resistance (Koves, et al., *Cell Metab.* 2008; 7(1):45-56). However, the role of such processes as primary drivers of insulin resistance related to altered cellular lipid balance (i.e., causes) versus serving as downstream effectors (i.e., effects) has been unclear. Moreover, regulatory circuitry that links control of cellular lipid balance and insulin signaling—which would enable identification of more effective therapeutic intervention methods—has not been identified. There is a still a need for identification of compounds that not only inhibit intramyocellular lipid accumulation but also increase glucose uptake.

It is an object of the present invention to provide compounds which inhibit intracellular lipid.

It is also an object of the present invention to provide compounds which reduce intracellular lipid and increase cellular glucose uptake and insulin signaling.

It is also an object of the present invention to provide small molecule inhibitors of the Mondo transcription factors.

It is also an object of the present invention to provide a method of reducing intracellular lipid in a subject in need thereof.

It is also an object of the present invention to provide a method of increasing insulin sensitivity in a subject in need thereof.

BRIEF SUMMARY OF THE INVENTION

Formulations and methods for reducing blood glucose, increasing insulin signaling, or combinations thereof, in a subject have been developed. The formulations include SBI-477 and compounds based on SBI-477, i.e., SBI-477 analogs (collectively, SBI-477 compounds), Mondo transcription factor inhibitors, or combinations thereof, in an effective amount to inhibit intracellular lipid accumulation, increase cellular glucose uptake, or combinations thereof, when compared to levels in a control subject not administered the composition. In some forms, the compounds are present in an effective amount to inhibit TAG synthesis. In some forms, the compounds are present in an effective amount to increase cellular glucose uptake, for example, by enhancing insulin signaling. Preferably, the formulation is effective to inhibit cellular TAG synthesis and increase cellular glucose uptake. In some forms, the compounds are present in an effective amount to inhibit nuclear localization of MondoA and/or MondoB. In preferred forms, the compounds reduce intramyocellular lipid, measured as, for example, TAG levels. Preferred compounds are SBI-477 and SBI-993, the structures of which are disclosed below.

Also disclosed are methods of reducing intracellular lipid accumulation, increase glucose uptake, or combinations thereof, in a subject in need thereof. The method includes administering to the subject an effective amount of SBI-477 compounds, a Mondo transcription factor inhibitor, or combinations thereof, to reducing intracellular lipid accumulation, increase glucose uptake, or combinations thereof, in the subject. In preferred forms, the subject is obese, has type-2 diabetes or pre-diabetes, or suffers from a condition associated with lipid toxicity.

Also disclosed are methods for treating one or more Myc-driven cancers, including neuroblastoma, lung squamous cell carcinoma/lung adenocarcinoma, liver hepatocellular carcinoma, colon adenocarcinoma, acute myeloid leukemia, and breast invasive carcinoma. The method includes administering the compositions and formulations disclosed herein to a subject in need thereof, where the formulations include the disclosed compounds in an effective amount to inhibit MondoA and/or MondoB.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several forms and embodiments of the disclosed method and compositions and together with the description, serve to explain the principles of the disclosed method and compositions.

FIG. 1A shows the effects of SBI-477, over a dose range, on triglyceride levels in human skeletal myotubes following 24 hour exposure to 100 µM oleate. Data is shown as percent of DMSO vehicle control. Representative of >5 experiments. FIGS. 1B and 1C show dose-dependent inhibition of myocyte TAG accumulation by SBI-477. FIG. 1B—primary human myotubes were incubated with the indicated concentrations of SBI-477, 1 µM triascin C, 1 µM A922500 (DGAT inhibitor) or vehicle control with 100 µM oleate for 24 hours. Fatty acid free bovine serum albumin (BSA) was included as non-lipid loading control. Bars represent mean triglyceride level normalized to total protein±SD. *$p<0.001$ vs. oleate/vehicle control by one-way ANOVA with Bonferroni post hoc test. FIG. 1C—primary human myotubes were incubated with 10 µM SBI-477 or vehicle control for 24 hours. Fatty acid (FA) uptake was measured as cellular uptake of 3H-oleate. Bars represent fatty acid uptake normalized to the vehicle control. FIG. 1D—human skeletal myotubes were incubated with the indicated concentration of SBI-477, AICAR (1 mM) or etomoxir (50 µM) for 24 hours. FAO rates were determined by 3H-palmitate oxidation (n=5). AICAR and etomoxir were included as controls for activation and inhibition of FAO, respectively. *$p<0.01$ vs. vehicle. Total cellular triglyceride levels were determined following incubation with SBI-477 (10 µM) for 24 hours with etomoxir (50 µM) in the absence (FIG. 1E) or presence of 1 mM carnitine (FIG. 1F) (n=4). *$p<0.05$ vs. vehicle control.

(FIG. 2A) Total mean TAG and DAG levels are shown. (FIG. 2B) Levels of individual TAG fatty acyl species with 18:1 species shown separately (left). The data represents mean±SD (n=3). *$p<0.05$ vs. vehicle, †$p<0.05$ vs. vehicle oleate loaded by Student's t-test.

(FIG. 4A) TXNIP and ARRDC4 mRNA levels as determined by quantitative RT- PCR in human myotubes treated with SBI-477 (10 μM) or DGAT1 inhibitor (DGATi, 1 mM) for 24 hours in the absence or presence of 100 μM oleate (n=4). Expression is shown relative to vehicle/BSA treatment. (FIG. 4B) TXNIP gene expression following exposure to a dose range of SBI-477 for 24 hours (n=4). (FIG. 4C) Left, Effect of SBI-477 on TXNIP protein levels as determined by western blot analysis by SBI-477. Right, Quantitation of the TXNIP western blot data is shown (n=5). *p<0.05 vs. Vehicle/BSA control, †p<0.05 vs. Vehicle/oleate by one-way ANOVA with Bonferroni post hoc test. The data are shown as mean±SD.

FIG. 5A—A luciferase reporter construct containing approximately 1.5 kb of the human TXNIP promoter (shown schematically at top) or a pGL3 control vector was transfected into H9c2 skeletal myocytes. The activity of the TXNIP promoter (relative luciferase units, RLU) was measured following treatment with SBI-477 at the indicated concentration (n=5). FIG. 5B—The activity of wild-type versus ChoRE mutant TXNIP promoters was measured in the presence and absence of SBI-477 (10 μM) for 24 hours (n=5). The red "X" notes inactivity mutations. FIG. 5C ChIP-qPCR analysis was performed with anti-MondoA (black bars) or IgG (open bars) control antibodies in human skeletal myotubes. Occupancy of MondoA on the ChoRE of the TXNIP or ARRDC4 promoter following treatment with SBI-477 treatment in the absence or presence of oleate is shown (n=4). Occupation on a Mef2 binding site within the IMPA2 promoter is shown as a negative control. FIG. 5D—Western blot analysis was performed on total cell lysate, and nuclear or cytoplasmic fractions from primary human myotubes treated with 10 μM SBI-477 or DMSO vehicle control for 24 hours. Lamin A/C and GAPDH were included as controls for the nuclear and cytoplasmic fractions, respectively. *p<0.05 vs. Vehicle by one-way ANOVA with Bonferroni post hoc test. The data represent mean±SD. HSE, heat shock element; ChoRE, carbohydrate response element; PPAR, peroxisome proliferator-activated receptor, IMPA2, inositol(myo)-1(or 4)-monophosphate 2.

(FIG. 6C) 2-DG uptake following MondoA KD (or siCon) in the absence or presence of insulin (n=5). *p<0.05 vs. siCon/Vehicle, †p<0.05 vs. siCon/insulin. (FIG. 6D) Cellular triglyceride levels following MondoA KD in the absence or presence of 100 μM oleate (n=5). *p<0.05 vs. siCon/Oleate. Effect of MondoA KD (FIG. 6E) or SBI-477 treatment (FIG. 6F) on the expression of genes encoding lipogenic and triglyceride synthesis enzymes (n=4) is shown. *p<0.05 vs. Veh or siCon. The data represents mean±SD. All statistical significance determined by Mann Whitney test.

FIG. 7C—Blood glucose levels are shown following a glucose tolerance test (1 g/kg glucose, i.p.) after dosing with SBI-993 or vehicle (n=6/group). Data represents mean±SEM. *p<0.05 HFD/Veh vs. HFD/SBI-993 by a two-way ANOVA with Tukey multiple comparison post hoc test. FIG. 7D—Western blot analysis of gastrocnemius skeletal muscle whole cell lysate from mice receiving an acute insulin challenge (1.5 U/kg for 10 minutes) to examine insulin signaling using phosphorylated Akt (S473). Top panel is quantification of western blot analysis (n=4-6/condition). Representative western blots are shown in the bottom panel. *p<0.05 vs. CD/vehicle and †p<0.05 vs. HFD/vehicle by one-way ANOVA with Bonferroni post hoc test. CD, control diet; HFD, high-fat diet.

DETAILED DESCRIPTION OF THE INVENTION

Figure 1A:
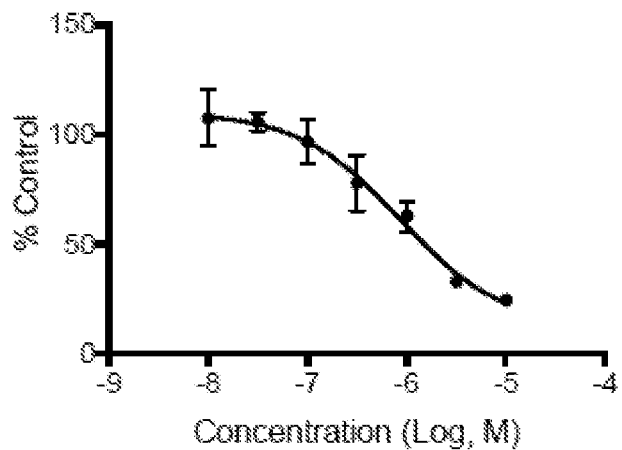
FIGS. 1A-1C show SBI-477 as a small molecule inhibitor of neutral lipid accumulation in human skeletal myotubes.

The disclosed method and compositions may be understood more readily by reference to the following detailed description of particular forms and embodiments and the Example included therein and to the Figures and their previous and following description.

I. Definitions

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular forms and embodiments only and is not intended to be limiting.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted. Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkyl groups, and cycloalkyl substituted alkyl. In preferred forms, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred forms, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

The terms "alkoxyl" or "alkoxy," "aroxy" or "aryloxy," generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits. A "lower alkoxy" group is an alkoxy group containing from one to six carbon atoms.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkenyl" as used herein is a hydrocarbon group of from 2 to 24 carbon atoms and structural formula containing at least one carbon-carbon double bond.

Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl" as used herein is any $C_5$-$C_{26}$ carbon-based aromatic group, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition.

Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $-CH_2-CF_3$, $-CCl_3$), $-CN$, aryl, heteroaryl, and combinations thereof.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, $-CN$, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, $-CN$, aryl, heteroaryl, and combinations thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

"Carbonyl," as used herein, is art-recognized and includes such moieties as can be represented by the general formula:

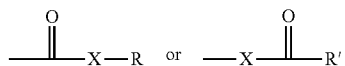

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R''$, or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or $-(CH_2)_m-R''$; R'' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

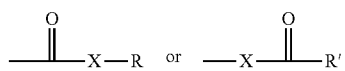

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, $-CN$, aryl, heteroaryl, and combinations thereof.

The term "carboxyl" is as defined above for the formula

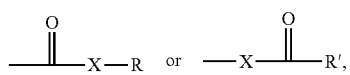

and is defined more specifically by the formula —R$^{iv}$COOH, wherein R$^{iv}$ is an alkyl, alkenyl, alkynyl, cycloalkyl, heterocyclyl, alkylaryl, arylalkyl, aryl, or heteroaryl. In preferred forms, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in R$^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof The term "phenoxy" is art recognized, and refers to a compound of the formula —OR$^v$ wherein R$^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "amide" or "amido" are used interchangeably, refer to both "unsubstituted amido" and "substituted amido" and are represented by the general formula:

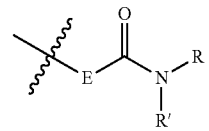

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide. In preferred forms, R and R' each independently represent a hydrogen atom, substituted or unsubstituted alkyl, a substituted or unsubstituted alkenyl, or —$(CH_2)_m$—R'". When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

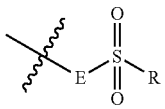

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R'", or E and R taken together with the S atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R'", R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

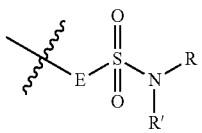

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R'", or R and R' taken together with the N atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide.

The term "phosphonyl" is represented by the formula

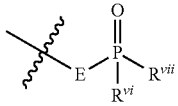

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The compounds and substituents can be substituted with, independently, with the substituents described above in the definition of "Substituted."

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable by the disclosed compounds.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

By the term "effective amount" of a compound as provided herein is meant a nontoxic but sufficient amount of the compound to provide the desired result.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

II. Compositions

An unbiased strategy in which a high-throughput chemical biology screen was employed to identify small molecule probes that influence downstream pathways involved in the control of cellular neutral lipid stores. One such molecule, SBI-477, coordinately reduced myocyte lipid stores and increased glucose uptake.

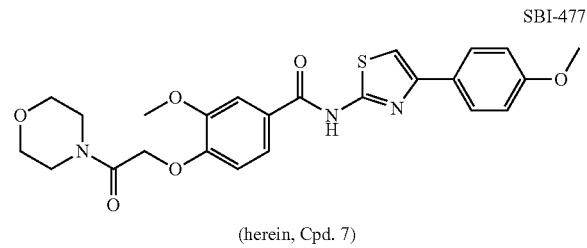 [SMILES: COc1ccc(-c2csc(NC(=O)c3ccc(OCC(=O)N4CCOCC4)c(OC)c3)n2)cc1]

SBI-477

(herein, Cpd. 7)

SBI-477 is a potent inhibitor of fatty acid incorporation into triglyceride in human skeletal myocytes. In parallel, SBI-477 increases myocyte glucose uptake by activating insulin signaling. The cellular actions of SBI-477 are attributable, at least in part, to inhibition of the transcription factor MondoA resulting in reduced expression of TAG synthesis genes and suppressed transcription of genes encoding suppressors of insulin signaling. An analog of SBI-477, named SBI-993 was used, which exhibited improved potency and suitable pharmacokinetic properties for in vivo bioavailability.

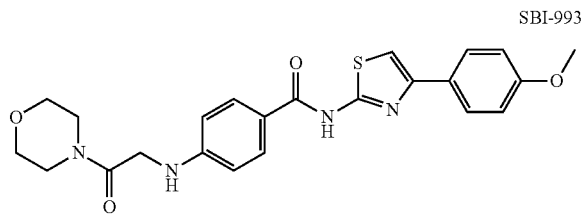 [SMILES: COc1ccc(-c2csc(NC(=O)c3ccc(NCC(=O)N4CCOCC4)cc3)n2)cc1]

SBI-993

Accordingly, in one aspect the compositions disclosed herein include Mondo transcription factor inhibitors (herein, "Mondo inhibitors"), preferably, MondoA and/or MondoB inhibitors. Mondo inhibitors are defined herein generally as compounds and/or molecules that reduce the expression, amount, or activity of at least one Mondo family protein, for example, the transcription factors, MondoA or MondoB cells and particularly, in the nucleus. A MondoA (or MondoB) inhibitor is considered to inhibit the activity of MondoA (or MondoB) if, for example, it reduces nuclear localization/levels of MondoA in cells treated with the inhibitor, when compared to non-treated cells. The inhibitor can reduce nuclear localization of MondoA (or MondoB) by for example, 10, 20, 30, 40, 50, 60, 70, 80, 90 or 100%. These include but are not limited to small molecule compounds as further described below, proteins, peptides and inhibitory nucleic acid molecules.

A. Compounds

The compositions disclosed herein include SBI-477 and its analogs (collectively, SBI-477 compounds) and/or protein/peptide/nucleic acid Mondo inhibitors. In a preferred embodiment, the Mondo inhibitor is an inhibitor of MondoA and/or MondoB.

1. Small Molecule Compounds

In one aspect described herein are compounds having the Formula I:

A-L$_1$-B-L$_2$-D-(R$_2$')$_n$,  Formula I wherein

A is substituted aryl, unsubstituted aryl, substituted heteroaryl, unsubstituted heteroaryl, substituted C$_3$-C$_{30}$ cycloalkyl, unsubstituted C$_3$-C$_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

L$_1$ is —C(O)NR'—, —NR'C(O)—, —C(O)O—, —OC(O)—, —O—, a bond, substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

L$_2$ is —C(O)NR'—, —NR'C(O)—, —C(O)O—, —OC(O)—, —O—, absent, a bond, substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

R' is, for each occurrence, independently hydrogen, substituted aryl, unsubstituted aryl, substituted heteroaryl, unsubstituted heteroaryl, substituted C$_3$-C$_{30}$ cycloalkyl, unsubstituted C$_3$-C$_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

B and D are independently substituted aryl, unsubstituted aryl, substituted heteroaryl, unsubstituted heteroaryl, substituted C$_3$-C$_{30}$ cycloalkyl, unsubstituted C$_3$-C$_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio, wherein if L$_2$ is absent and B and D are each independently substituted aryl, unsubstituted aryl, substituted heteroaryl, unsubstituted heteroaryl, B and D are a fused ring or a polycyclic system;

R$_2$' is, for each occurrence, independently hydrogen, substituted aryl, unsubstituted aryl, substituted heteroaryl, unsubstituted heteroaryl, substituted C$_3$-C$_{30}$ cycloalkyl, unsubstituted C$_3$-C$_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, unsubstituted alkylthio, halogen (F, Cl, Br, I), hydroxyl, nitro, cyano, or two R2' units fuse to form substituted aryl, unsubstituted aryl, substituted heteroaryl, unsubstituted heteroaryl, substituted C$_3$-C$_{30}$ cycloalkyl, unsubstituted C$_3$-C$_{30}$ cycloalkyl, substituted heterocyclyl, or unsubstituted heterocyclyl, and wherein n is an integer between 1 and 5, inclusive.

In some forms, the compounds have the general Formula I, as described above, with the exception that B and D are independently substituted aryl, unsubstituted aryl, substituted heteroaryl, or unsubstituted heteroaryl.

In some forms the compounds of Formula I are represented by the general Formula II:

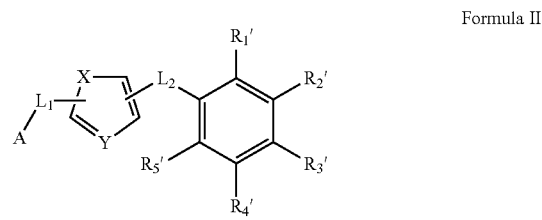

Formula II wherein

A is as defined above for Formula I,

L$_1$ is —C(O)NR'—, —NR'C(O)—, —C(O)O—, —OC(O)—, —O—, a bond, substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

$L_2$ is —C(O)NR'—, —NR'C(O)—, —C(O)O—, —OC(O)—, —O—, absent, a bond, substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

R' is hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;

$R_1'$, $R_2'$, $R_3'$, $R_4'$ and $R_5'$ are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, or cyano, or any two adjacent $R_1'$, $R_2'$, $R_3'$, $R_4'$ and $R_5'$ fuse to form substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, or unsubstituted heterocyclyl, and X and Y are, as valence permits, independently C, O, N, S, $CR_6'R_7'$, or $NR_8'$, wherein $R_6'$, $R_7'$, and $R_8'$ are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio.

In some forms, the compounds of Formula II are represented by the general Formula III:

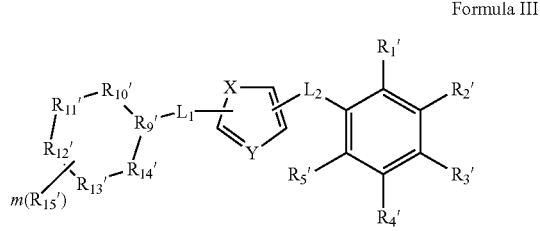

Formula III wherein $L_1$, $L_2$, X, Y, $R_1'$, $R_2'$, $R_3'$, $R_4'$ and $R_5'$ are as described above for formula II, $R_9'$, $R_{10}'$, $R_{11}'$, $R_{12}'$, $R_{13}'$, and $R_{14}'$ are independently C, O, N, S, wherein the bonds between adjacent $R_9'$ to $R_{14}'$ are double or single according to valency, wherein $R_9'$ to $R_{14}'$ are bound to none, one, or two hydrogens according to valency, wherein $R_{15}'$ is, for each occurrence, independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, or cyano, and m is an integer between 1 and 12, inclusive.

In some forms, the compounds of Formula III are represented by the general Formula IV or general Formula V:

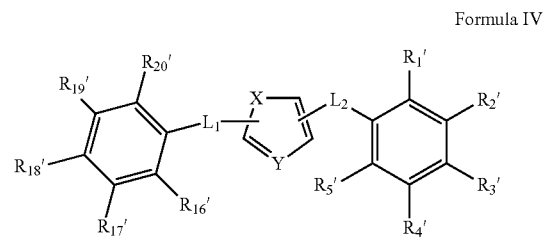

Formula IV

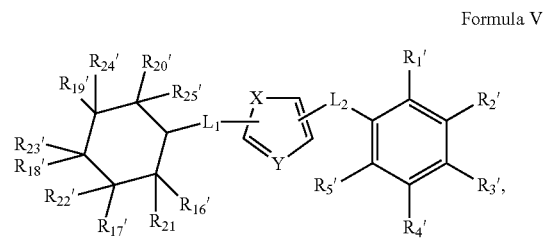

Formula V wherein $L_1$, $L_2$, X, Y, $R_1'$, $R_2'$, $R_3'$, $R_4'$ and $R_5'$ are as described above for Formula III, $R_{16}'$, $R_{17}'$, $R_{18}'$, $R_{19}'$, $R_{20}'$, $R_{21}'$, $R_{22}'$, $R_{23}'$, $R_{24}'$, and $R_{25}'$ are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, or cyano.

In some forms, the compounds of Formula I are represented by the general Formula VI or general Formula VII:

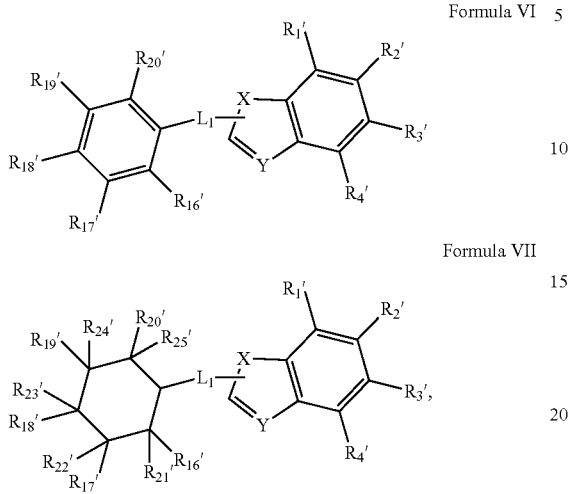

Formula VI

Formula VII wherein $L_1$, $L_2$, X, Y, $R_1'$, $R_2'$, $R_3'$, $R_4'$ and $R_5'$ are as described above for Formula III, $R_{16}'$, $R_{17}'$, $R_{18}'$, $R_{19}'$, $R_{20}'$, $R_{21}'$, $R_{22}'$, $R_{23}'$, $R_{24}'$, and $R_{25}'$ are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, or cyano.

In some forms, the compounds of Formula IV are represented by Formula VIII,

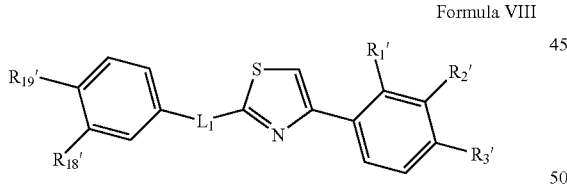

Formula VIII wherein $L_1$ is —NR'C(O)—, —C(O)NR'—, or substituted amino, $R_1'$, $R_2'$ and $R_3'$ are independently hydrogen, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, cyano, $R_2'$ and $R_3'$ combine to form, substituted heterocyclyl or unsubstituted heterocyclyl, and $R_{18}'$ and $R_{19}'$ are independently hydrogen, substituted alkoxy, unsubstituted alkoxy, substituted amino, or unsubstituted amino.

In some forms, the compounds of Formula II are represented by Formula IX:

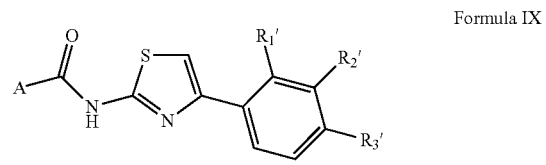

Formula IX wherein $R_1'$, $R_2'$ and $R_3'$ are independently hydrogen, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, cyano, $R_1'$ and $R_2'$, or $R_2'$ and $R_3'$ combine to form substituted heterocyclyl or unsubstituted heterocyclyl, and A is a substituted alkyl, unsubstituted alkyl, substituted $C_3$-$C_{30}$ cycloalkyl, or unsubstituted $C_3$-$C_{30}$ cycloalkyl.

In some forms, the compounds of Formula VI are represented by the general Formula X,

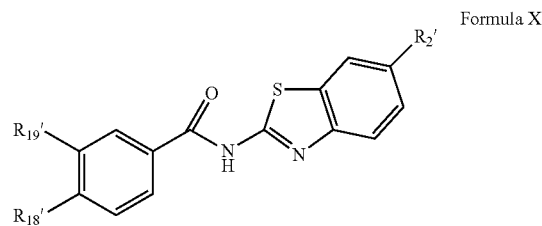

Formula X wherein $R_2'$ is hydrogen, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, cyano, and $R_{18}'$ and $R_{19}'$ are independently substituted alkoxy, or unsubstituted alkoxy.

In some forms, the compounds have the general Formula XI

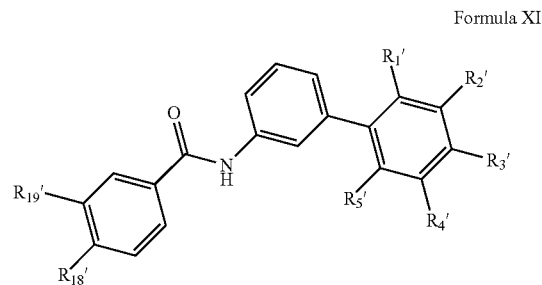

Formula XI $R_1'$, $R_2'$, $R_3'$, $R_4'$, and $R_5'$ are independently hydrogen, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, cyano, and $R_{18}'$ and $R_{19}'$ are independently substituted alkoxy, or unsubstituted alkoxy.

In some forms, the compounds of Formula IV have the general Formula XII,

Formula XII

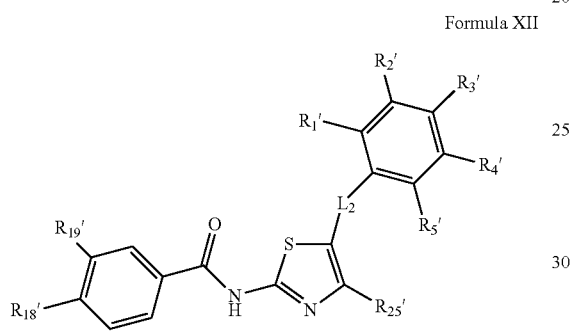

wherein $L_2$ is a bond, substituted alkylene, or unsubstituted alkylene, $R_1'$, $R_2'$, $R_3'$, $R_4'$, $R_5'$, and $R_{25}'$ are independently hydrogen, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, cyano, and $R_{18}'$ and $R_{19}'$ are independently substituted alkoxy, or unsubstituted alkoxy.

Specific compounds (Cpd) prepared according to General Synthetic Scheme I are shown below.

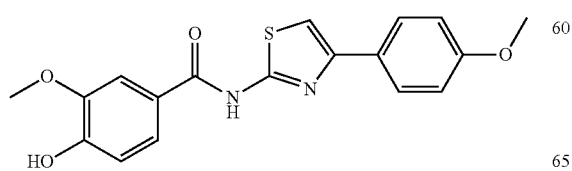

4-hydroxy-3-methoxy-N-(4-(4-methoxyphenyl)thiazol-2-yl)benzamide (Cpd. 1)

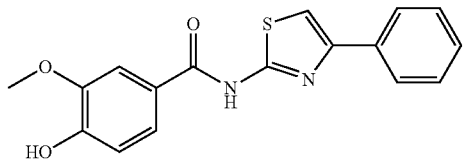 [SMILES: COc1cc(C(=O)Nc2nc(-c3ccccc3)cs2)ccc1O]

4-hydroxy-3-methoxy-N-(4-phenylthiazol-2-yl)benzamide (Cpd. 2)

4-hydroxy-3-methoxy-N-(4-(p-tolyl)thiazol-2-yl)benzamide (Cpd. 3)

N-(4-(4-chlorophenyl)thiazol-2-yl)-4-hydroxy-3-methoxybenzamide (Cpd. 4)

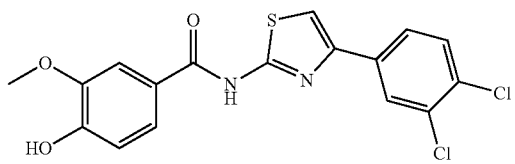 [SMILES: COc1cc(C(=O)Nc2nc(-c3ccc(Cl)c(Cl)c3)cs2)ccc1O]

N-(4-(3,4-dichlorophenyl)thiazol-2-yl)-4-hydroxy-3-methoxybenzamide (Cpd. 5)

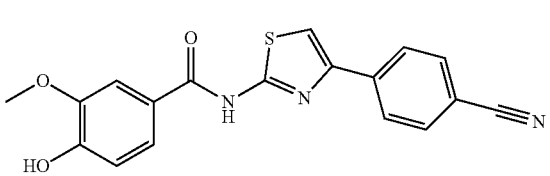 [SMILES: COc1cc(C(=O)Nc2nc(-c3ccc(C#N)cc3)cs2)ccc1O]

N-(4-(4-cyanophenyl)thiazol-2-yl)-4-hydroxy-3-methoxybenzamide (Cpd. 6)

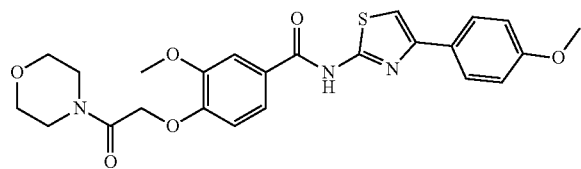 [SMILES: COc1ccc(-c2csc(NC(=O)c3ccc(OCC(=O)N4CCOCC4)c(OC)c3)n2)cc1]

3-methoxy-N-(4-(4-methoxyphenyl)thiazol-2-yl)-4-(2-morpholino-2-oxoethoxy)benzamide (Cpd. 7)

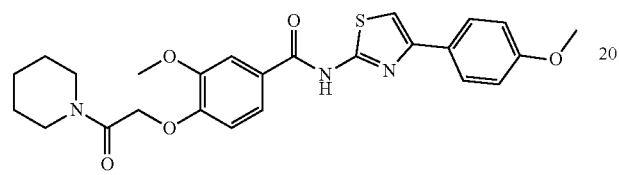

3-methoxy-N-(4-(4-methoxyphenyl)thiazol-2-yl)-4-(2-oxo-2-(piperidin-1-yl)ethoxy)benzamide (Cpd. 8)

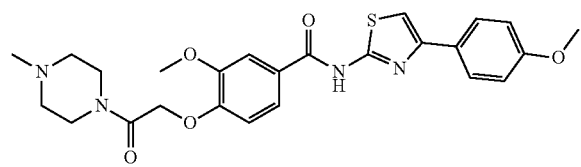

3-methoxy-N-(4-(4-methoxyphenyl)thiazol-2-yl)-4-(2-(4-methylpiperazin-1-yl)-2-oxoethoxy)benzamide (Cpd. 9)

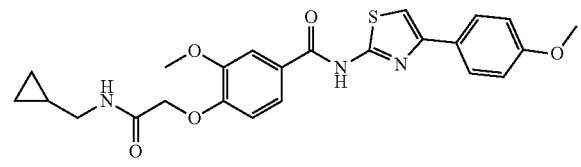 [SMILES: COc1ccc(-c2csc(NC(=O)c3ccc(OCC(=O)NCC4CC4)c(OC)c3)n2)cc1]

4-(2-((cyclopropylmethyl)amino)-2-oxoethoxy)-3-methoxy-N-(4-(4-methoxyphenyl)thiazol-2-yl)benzamide (Cpd. 10)

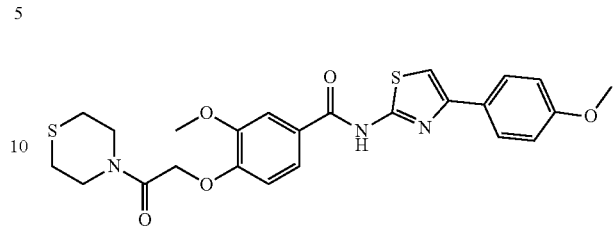

3-methoxy-N-(4-(4-methoxyphenyl)thiazol-2-yl)-4-(2-oxo-2-thiomorpholinoethoxy)benzamide (Cpd. 11)

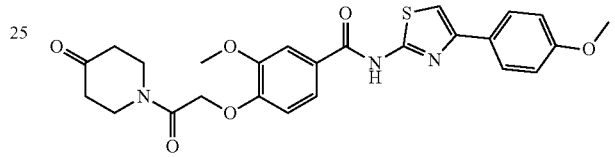

3-methoxy-N-(4-(4-methoxyphenyl)thiazol-2-yl)-4-(2-oxo-2-(4-oxopiperidin-1-yl)ethoxy)benzamide (Cpd. 12)

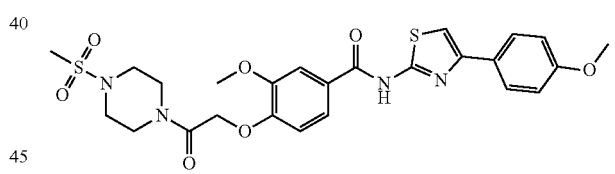

3-methoxy-N-(4-(4-methoxyphenyl)thiazol-2-yl)-4-(2-(4-(methylsulfonyl)piperazin-1-yl)-2-oxoethoxy)benzamide (Cpd. 13)

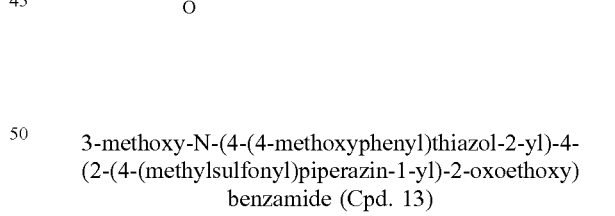

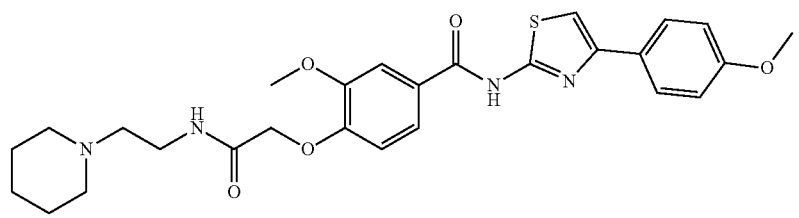 [SMILES: COc1ccc(-c2csc(NC(=O)c3ccc(OCC(=O)NCCN4CCCCC4)c(OC)c3)n2)cc1]

| 31 | 32 |
|---|---|
| 3-methoxy-N-(4-(4-methoxyphenyl)thiazol-2-yl)-4-(2-oxo-2-((2-(piperidin-1-yl)ethyl)amino)ethoxy)benzamide (Cpd. 14) | 4-(2-amino-2-oxoethoxy)-3-methoxy-N-(4-(4-methoxyphenyl)thiazol-2-yl)benzamide (Cpd. 17) |

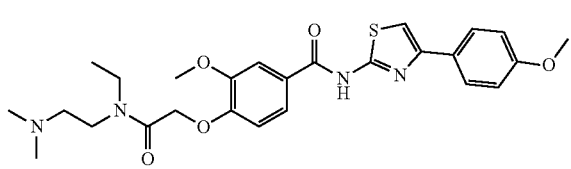

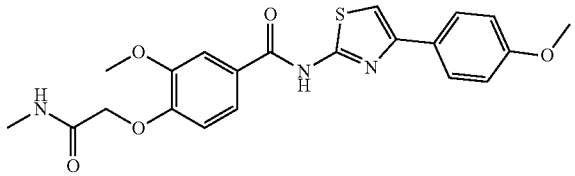

4-(2-((2-(dimethylamino)ethyl)(ethyl)amino)-2-oxo-ethoxy)-3-methoxy-N-(4-(4-methoxyphenyl)thiazol-2-yl)benzamide (Cpd. 15)

3-methoxy-N-(4-(4-methoxyphenyl)thiazol-2-yl)-4-(2-(methylamino)-2-oxoethoxy)benzamide (Cpd. 18)

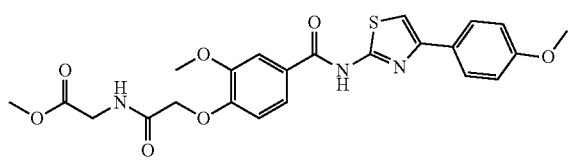

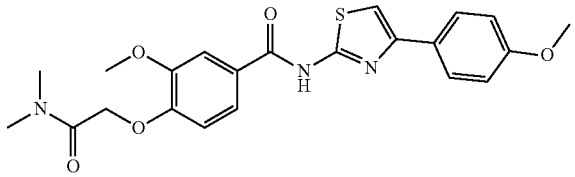

Methyl (2-(2-methoxy-4-((4-(4-methoxyphenyl)thiazol-2-yl)carbamoyl)phenoxy)acetyl)glycinate (Cpd. 16)

4-(2-(dimethylamino)-2-oxoethoxy)-3-methoxy-N-(4-(4-methoxyphenyl)thiazol-2-yl)benzamide (Cpd. 19)

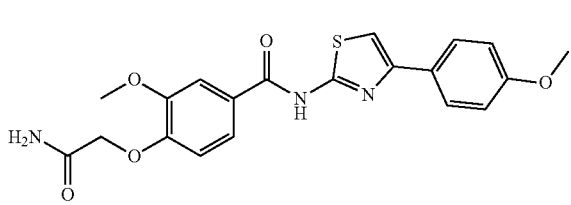 [SMILES: COc1ccc(-c2csc(NC(=O)c3ccc(OCC(N)=O)c(OC)c3)n2)cc1]

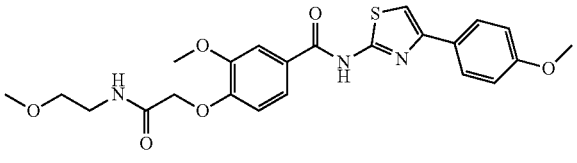

3-methoxy-4-(2-((2-methoxyethyl)amino)-2-oxoethoxy)-N-(4-(4-methoxyphenyl)thiazol-2-yl)benzamide (Cpd. 20)

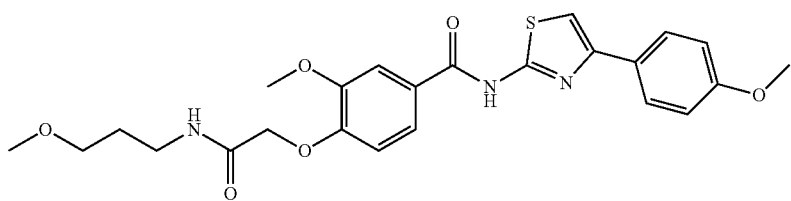

33

3-methoxy-N-(4-(4-methoxyphenyl)thiazol-2-yl)-4-
(2-((3-methoxypropyl)amino)-2-oxoethoxy)benz-
amide (Cpd. 21)

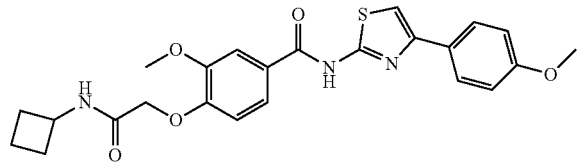 [SMILES: COc1ccc(-c2csc(NC(=O)c3ccc(OCC(=O)NC4CCC4)c(OC)c3)n2)cc1]

4-(2-(cyclobutylamino)-2-oxoethoxy)-3-methoxy-N-
(4-(4-methoxyphenyl)thiazol-2-yl)benzamide (Cpd.
22)

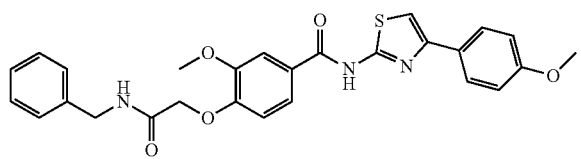 [SMILES: COc1ccc(-c2csc(NC(=O)c3ccc(OCC(=O)NCc4ccccc4)c(OC)c3)n2)cc1]

4-(2-(benzylamino)-2-oxoethoxy)-3-methoxy-N-(4-
(4-methoxyphenyl)thiazol-2-yl)benzamide (Cpd. 23)

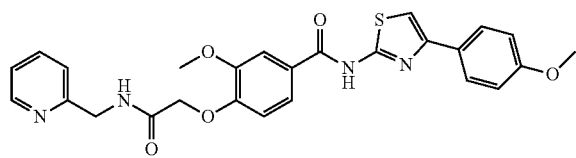 [SMILES: COc1ccc(-c2csc(NC(=O)c3ccc(OCC(=O)NCc4ccccn4)c(OC)c3)n2)cc1]

3-methoxy-N-(4-(4-methoxyphenyl)thiazol-2-yl)-4-
(2-oxo-2-((pyridin-2-ylmethyl)amino)ethoxy) Benz-
amide (Cpd. 24)

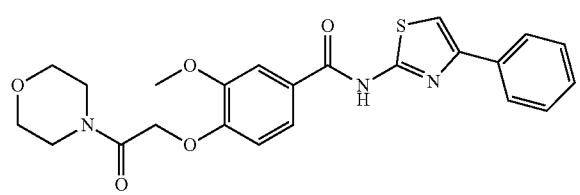 [SMILES: COc1cc(C(=O)Nc2nc(-c3ccccc3)cs2)ccc1OCC(=O)N1CCOCC1]

3-methoxy-4-(2-morpholino-2-oxoethoxy)-N-(4-
phenylthiazol-2-yl)benzamide (Cpd. 25)

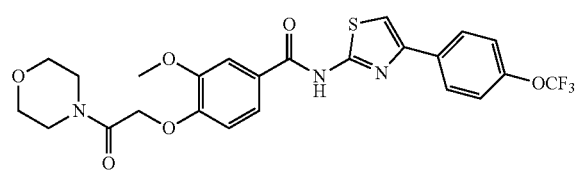 [SMILES: COc1cc(C(=O)Nc2nc(-c3ccc(OC(F)(F)F)cc3)cs2)ccc1OCC(=O)N1CCOCC1]

34

3-methoxy-4-(2-morpholino-2-oxoethoxy)-N-(4-(4-
(trifluoromethoxy)phenyl)thiazol-2-yl)benzamide
(Cpd. 26)

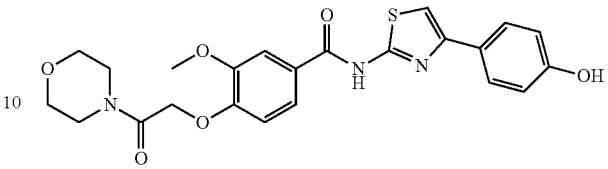

N-(4-(4-hydroxyphenyl)thiazol-2-yl)-3-methoxy-4-
(2-morpholino-2-oxoethoxy)benzamide (Cpd. 27)

N-(4-(4-ethoxyphenyl)thiazol-2-yl)-3-methoxy-4-(2-
morpholino-2-oxoethoxy)benzamide (Cpd. 28)

N-(4-(4-isopropoxyphenyl)thiazol-2-yl)-3-methoxy-
4-(2-morpholino-2-oxoethoxy)benzamide (Cpd. 29)

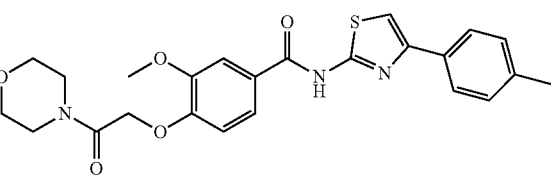

3-methoxy-4-(2-morpholino-2-oxoethoxy)-N-(4-(p-
tolyl)thiazol-2-yl)benzamide (Cpd. 30)

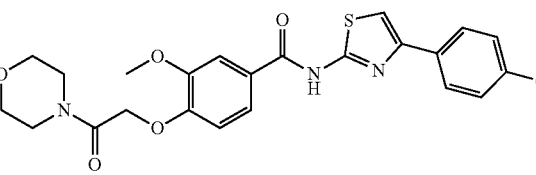

N-(4-(4-chlorophenyl)thiazol-2-yl)-3-methoxy-4-(2-morpholino-2-oxoethoxy)benzamide (Cpd. 31)

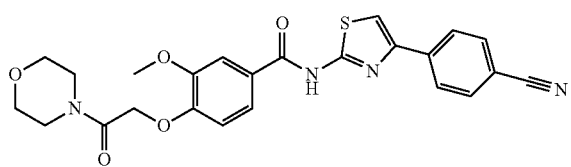 [SMILES: COc1cc(C(=O)Nc2nc(-c3ccc(C#N)cc3)cs2)ccc1OCC(=O)N1CCOCC1]

N-(4-(4-cyanophenyl)thiazol-2-yl)-3-methoxy-4-(2-morpholino-2-oxoethoxy)benzamide (Cpd. 32)

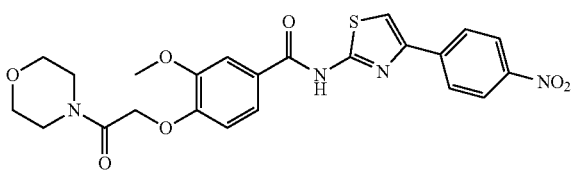 [SMILES: COc1cc(C(=O)Nc2nc(-c3ccc([N+](=O)[O-])cc3)cs2)ccc1OCC(=O)N1CCOCC1]

3-methoxy-4-(2-morpholino-2-oxoethoxy)-N-(4-(4-nitrophenyl)thiazol-2-yl)benzamide (Cpd. 33)

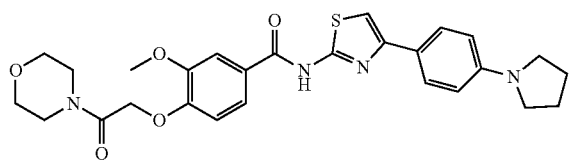 [SMILES: COc1cc(C(=O)Nc2nc(-c3ccc(N4CCCC4)cc3)cs2)ccc1OCC(=O)N1CCOCC1]

3-methoxy-4-(2-morpholino-2-oxoethoxy)-N-(4-(4-(pyrrolidin-1-yl)phenyl)thiazol-2-yl)benzamide (Cpd. 34)

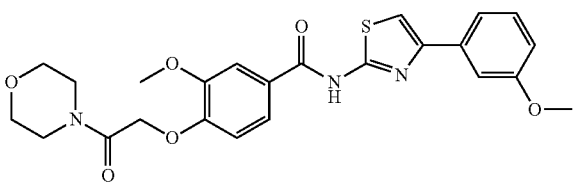 [SMILES: COc1cccc(-c2csc(NC(=O)c3ccc(OCC(=O)N4CCOCC4)c(OC)c3)n2)c1]

3-methoxy-N-(4-(3-methoxyphenyl)thiazol-2-yl)-4-(2-morpholino-2-oxoethoxy)benzamide (Cpd. 35)

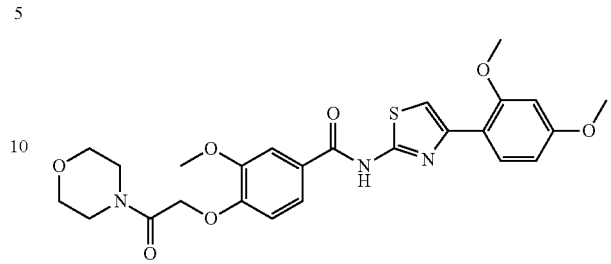

N-(4-(2,4-dimethoxyphenyl)thiazol-2-yl)-3-methoxy-4-(2-morpholino-2-oxoethoxy)benzamide (Cpd. 36)

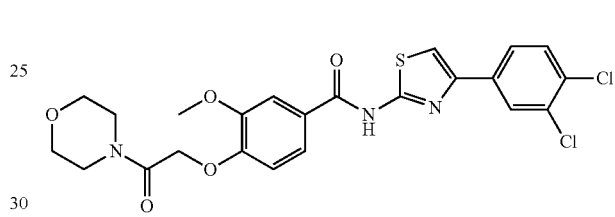

N-(4-(3,4-dichlorophenyl)thiazol-2-yl)-3-methoxy-4-(2-morpholino-2-oxoethoxy)benzamide (Cpd. 37

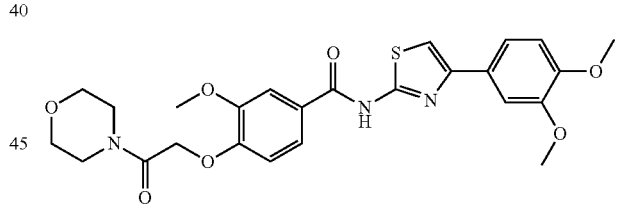

N-(4-(3,4-dimethoxyphenyl)thiazol-2-yl)-3-methoxy-4-(2-morpholino-2-oxoethoxy)benzamide (Cpd. 38)

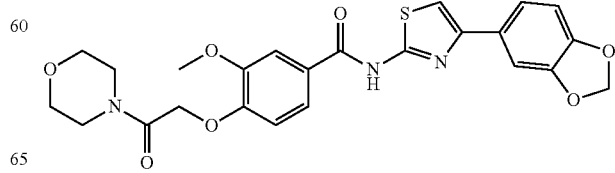

37

N-(4-(benzo[d][1,3]dioxol-5-yl)thiazol-2-yl)-3-methoxy-4-(2-morpholino-2-oxoethoxy)benzamide (Cpd. 39)

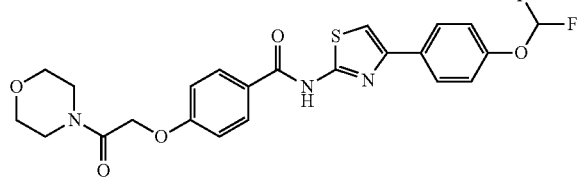

N-(4-(4-(difluoromethoxy)phenyl)thiazol-2-yl)-4-(2-morpholino-2-oxoethoxy)benzamide (Cpd. 40)

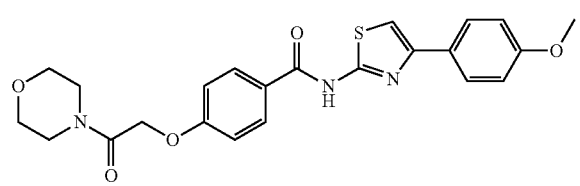 [SMILES: COc1ccc(-c2csc(NC(=O)c3ccc(OCC(=O)N4CCOCC4)cc3)n2)cc1]

N-(4-(4-methoxyphenyl)thiazol-2-yl)-4-(2-morpholino-2-oxoethoxy)benzamide (Cpd. 41)

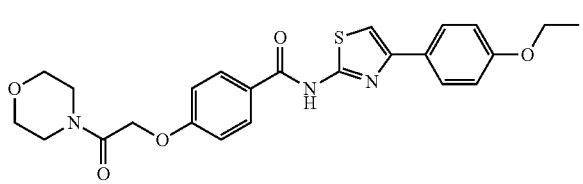 [SMILES: CCOc1ccc(-c2csc(NC(=O)c3ccc(OCC(=O)N4CCOCC4)cc3)n2)cc1]

N-(4-(4-ethoxyphenyl)thiazol-2-yl)-4-(2-morpholino-2-oxoethoxy)benzamide (Cpd. 42)

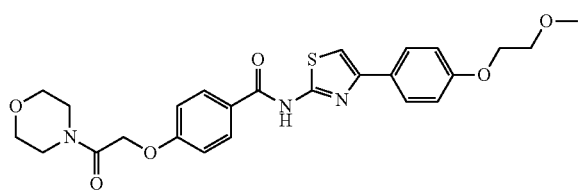 [SMILES: COCCOc1ccc(-c2csc(NC(=O)c3ccc(OCC(=O)N4CCOCC4)cc3)n2)cc1]

38

N-(4-(4-(2-methoxyethoxy)phenyl)thiazol-2-yl)-4-(2-morpholino-2-oxoethoxy)benzamide (Cpd. 43)

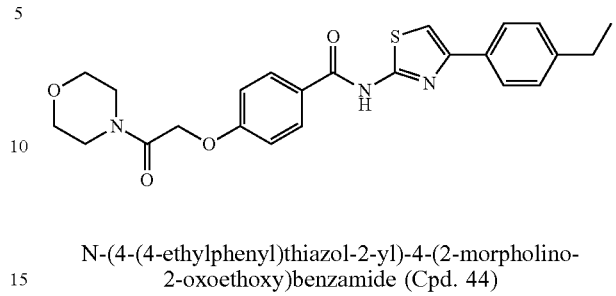

N-(4-(4-ethylphenyl)thiazol-2-yl)-4-(2-morpholino-2-oxoethoxy)benzamide (Cpd. 44)

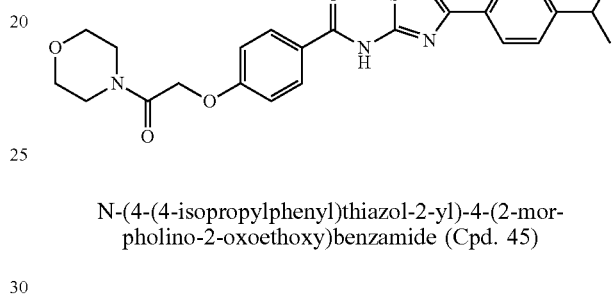

N-(4-(4-isopropylphenyl)thiazol-2-yl)-4-(2-morpholino-2-oxoethoxy)benzamide (Cpd. 45)

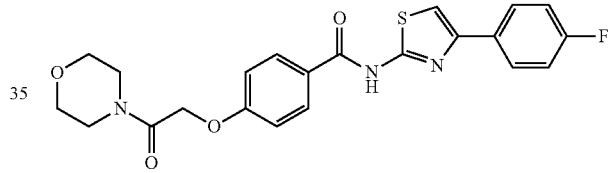

N-(4-(4-fluorophenyl)thiazol-2-yl)-4-(2-morpholino-2-oxoethoxy)benzamide (Cpd. 46)

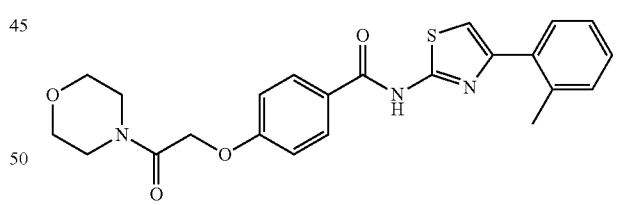

4-(2-morpholino-2-oxoethoxy)-N-(4-(o-tolyl)thiazol-2-yl)benzamide (Cpd. 47)

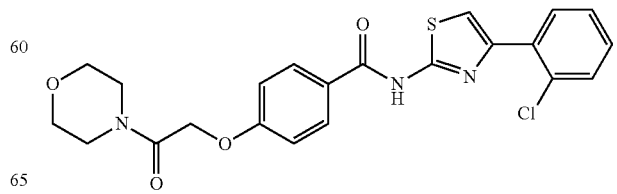

| 39 | 40 |
|---|---|
| N-(4-(2-chlorophenyl)thiazol-2-yl)-4-(2-morpholino-2-oxoethoxy)benzamide (Cpd. 48) | 4-(2-morpholino-2-oxoethoxy)-N-(4-(m-tolyl)thiazol-2-yl)benzamide (Cpd. 51) |

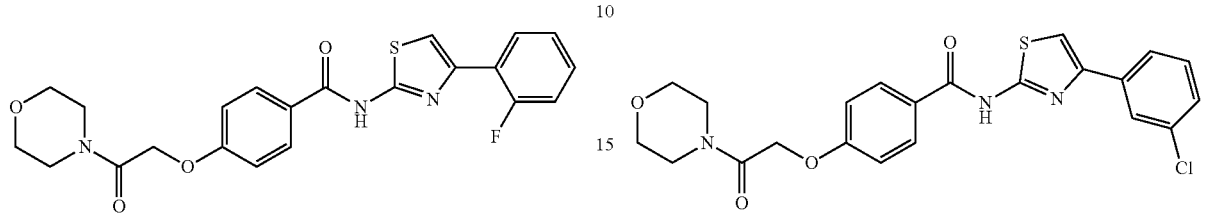

N-(4-(2-fluorophenyl)thiazol-2-yl)-4-(2-morpholino-2-oxoethoxy)benzamide (Cpd. 49)

N-(4-(3-chlorophenyl)thiazol-2-yl)-4-(2-morpholino-2-oxoethoxy)benzamide (Cpd. 52)

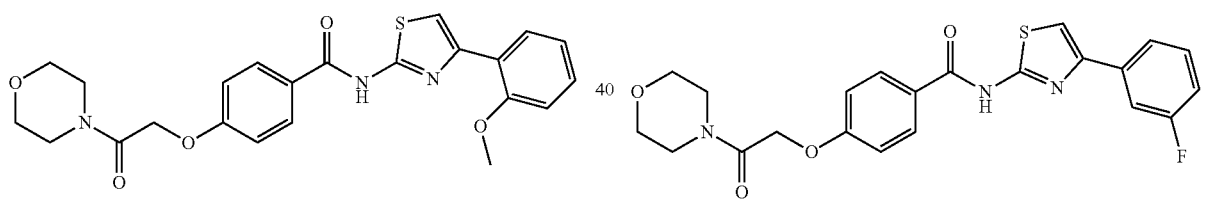

N-(4-(2-methoxyphenyl)thiazol-2-yl)-4-(2-morpholino-2-oxoethoxy)benzamide (Cpd. 50)

N-(4-(3-fluorophenyl)thiazol-2-yl)-4-(2-morpholino-2-oxoethoxy)benzamide (Cpd. 53)

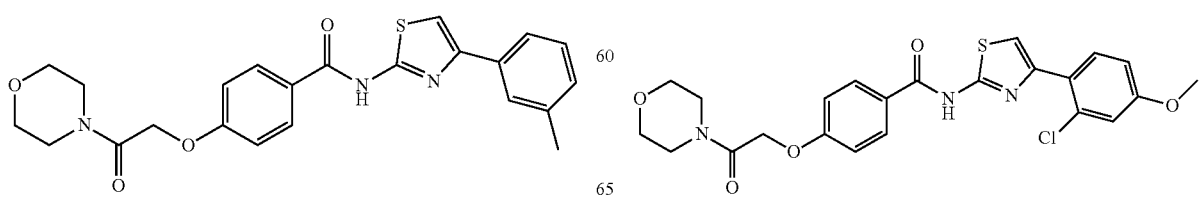

N-(4-(2-chloro-4-methoxyphenyl)thiazol-2-yl)-4-(2-morpholino-2-oxoethoxy)benzamide (Cpd. 54)

4-(2-amino-2-oxoethoxy)-N-(4-(2-chloro-4-methoxyphenyl)thiazol-2-yl)benzamide (Cpd. 57)

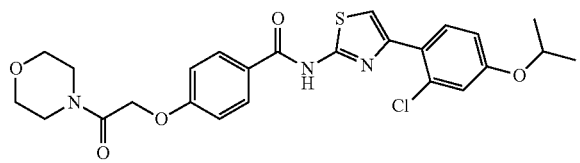 [SMILES: CC(C)Oc1ccc(-c2csc(NC(=O)c3ccc(OCC(=O)N4CCOCC4)cc3)n2)c(Cl)c1]

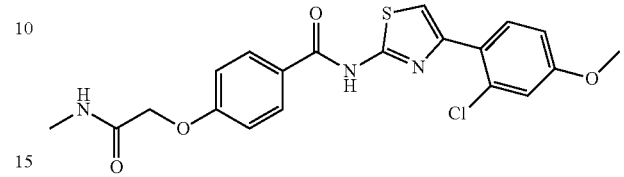

N-(4-(2-chloro-4-isopropoxyphenyl)thiazol-2-yl)-4-(2-morpholino-2-oxoethoxy)benzamide (Cpd. 55)

N-(4-(2-chloro-4-methoxyphenyl)thiazol-2-yl)-4-(2-(methylamino)-2-oxoethoxy)benzamide (Cpd. 58)

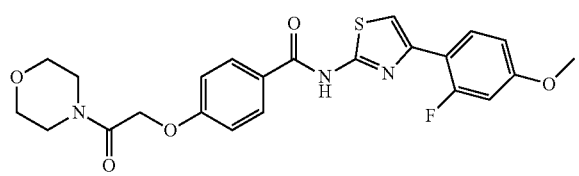 [SMILES: COc1ccc(-c2csc(NC(=O)c3ccc(OCC(=O)N4CCOCC4)cc3)n2)c(F)c1]

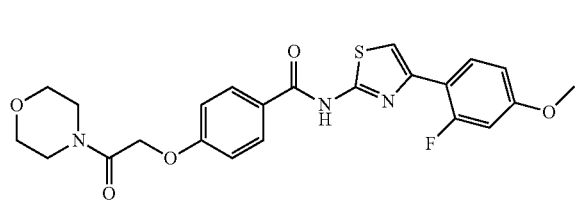

N-(4-(2-chloro-4-methoxyphenyl)thiazol-2-yl)-4-(2-(ethylamino)-2-oxoethoxy)benzamide (Cpd. 59)

N-(4-(2-fluoro-4-methoxyphenyl)thiazol-2-yl)-4-(2-morpholino-2-oxoethoxy)benzamide (Cpd. 56)

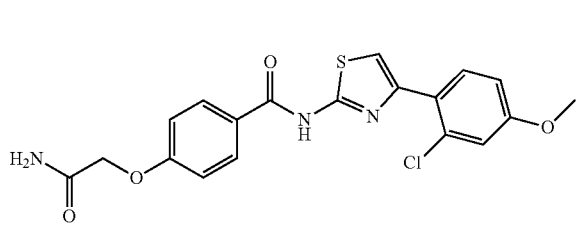 [SMILES: COc1ccc(-c2csc(NC(=O)c3ccc(OCC(N)=O)cc3)n2)c(Cl)c1]

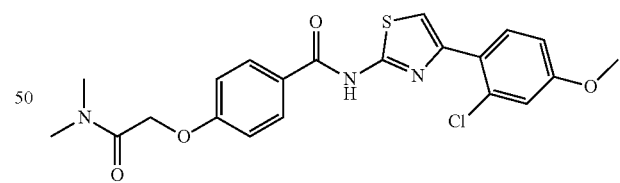 [SMILES: CCNC(=O)COc1ccc(C(=O)Nc2nc(-c3ccc(OC)cc3Cl)cs2)cc1]

N-(4-(2-chloro-4-methoxyphenyl)thiazol-2-yl)-4-(2-(dimethylamino)-2-oxoethoxy)benzamide (Cpd. 60)

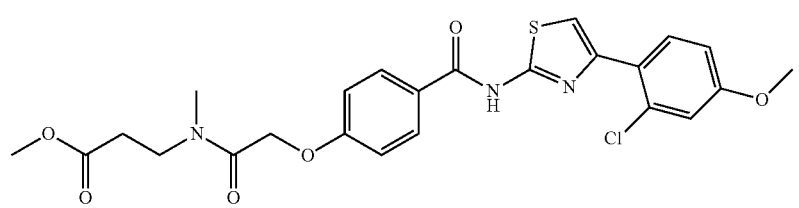

| 43 | 44 |
|---|---|
| methyl 3-(2-(4-((4-(2-chloro-4-methoxyphenyl)thiazol-2-yl)carbamoyl)phenoxy)-N-methylacetamido) propanoate (Cpd. 61) | N-(4-(2-chlorophenyl)thiazol-2-yl)-4-(2-(dimethylamino)-2-oxoethoxy)-3-(hept-6-ynamido)benzamide (Cpd. 64) |

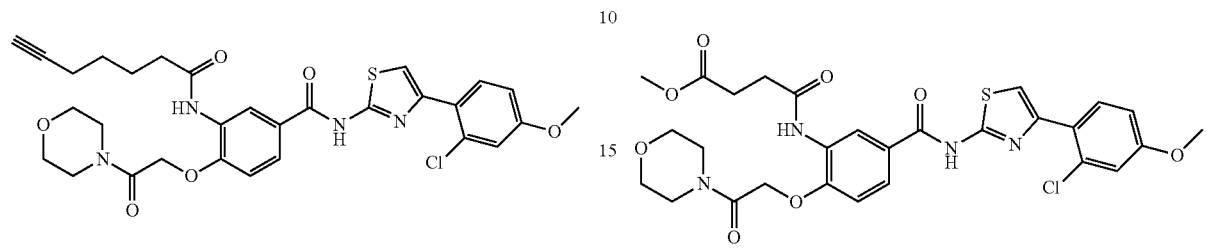

N-(4-(2-chloro-4-methoxyphenyl)thiazol-2-yl)-3-(hept-6-ynamido)-4-(2-morpholino-2-oxoethoxy) Benzamide (Cpd. 62)

methyl 4-((5-((4-(2-chloro-4-methoxyphenyl)thiazol-2-yl)carbamoyl)-2-(2-morpholino-2-oxoethoxy) phenyl)amino)-4-oxobutanoate (Cpd. 65)

Exemplary compounds (Cpd) prepared according to General Synthetic Scheme 2 are shown below

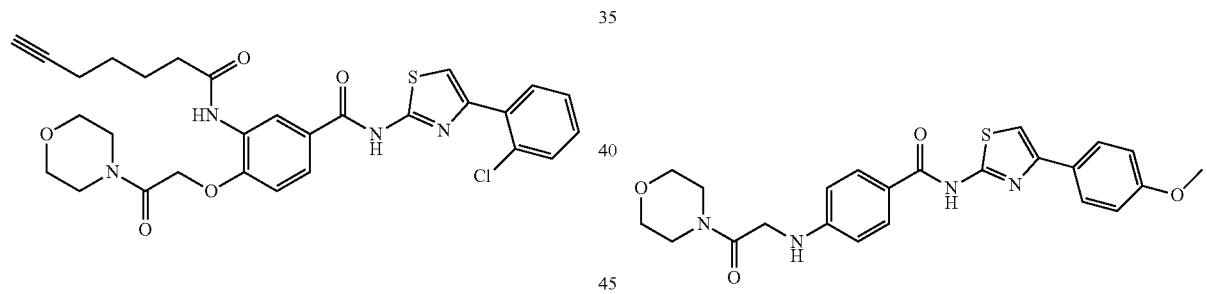

N-(4-(2-chlorophenyl)thiazol-2-yl)-3-(hept-6-ynamido)-4-(2-morpholino-2-oxoethoxy)benzamide (Cpd. 63)

N-(4-(4-methoxyphenyl)thiazol-2-yl)-4-((2-morpholino-2-oxoethyl)amino)benzamide (Cpd. 66)

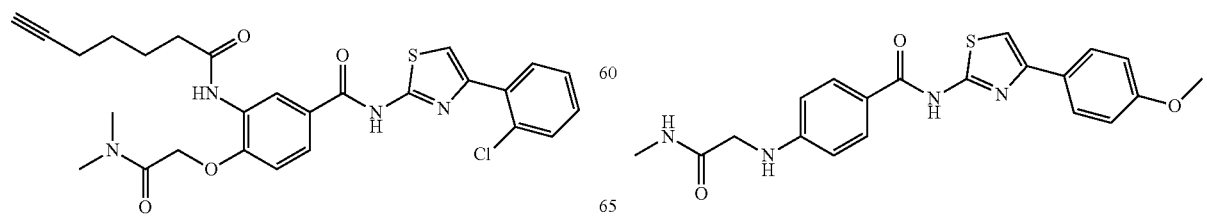

45

N-(4-(4-methoxyphenyl)thiazol-2-yl)-4-((2-(methyl-amino)-2-oxoethyl)amino)benzamide (Cpd 67)

46

N-(4-(2-chloro-4-methoxyphenyl)thiazol-2-yl)-4-((2-morpholino-2-oxoethyl)amino)benzamide (Cpd 70)

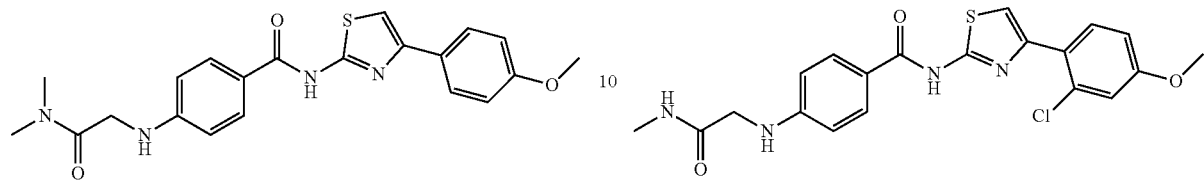

4-((2-(dimethylamino)-2-oxoethyl)amino)-N-(4-(4-methoxyphenyl)thiazol-2-yl)benzamide (Cpd 68)

N-(4-(2-chloro-4-methoxyphenyl)thiazol-2-yl)-4-((2-(methylamino)-2-oxoethyl)amino)benzamide (Cpd 71)

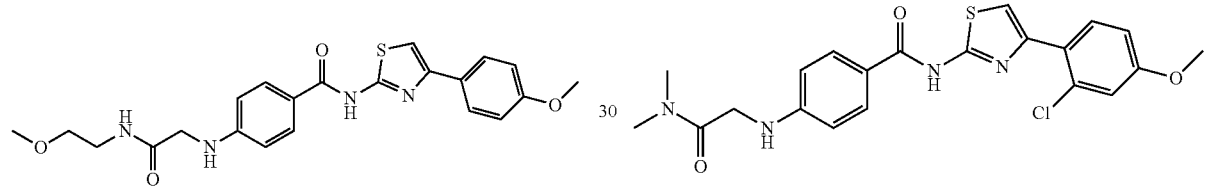

4-((2-((2-methoxyethyl)amino)-2-oxoethyl)amino)-N-(4-(4-methoxyphenyl)thiazol-2-yl)benzamide (Cpd 69)

N-(4-(2-chloro-4-methoxyphenyl)thiazol-2-yl)-4-((2-(dimethylamino)-2-oxoethyl)amino)benzamide (Cpd 72)

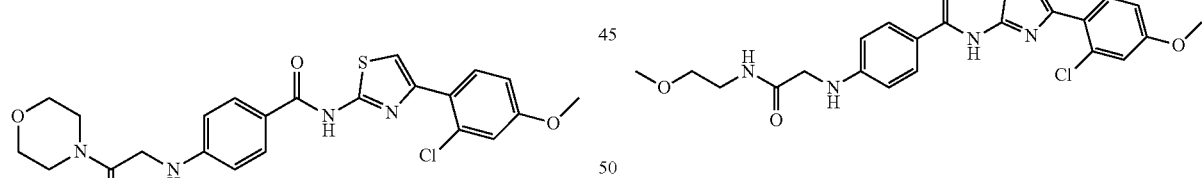

N-(4-(2-chloro-4-methoxyphenyl)thiazol-2-yl)-4-((2-((2-methoxyethyl)amino)-2-oxoethyl)amino)benz-amide (Cpd 73)

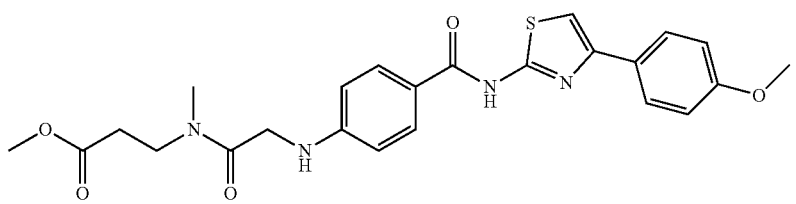

methyl 3-(2-((4-((4-(4-methoxyphenyl)thiazol-2-yl)carbamoyl)phenyl)amino)-N-methylacetamido) propanoate (Cpd 74)

3-methoxy-N-(4-(4-methoxyphenyl)thiazol-2-yl)-4-((2-morpholino-2-oxoethyl)amino)benzamide (Cpd 75)

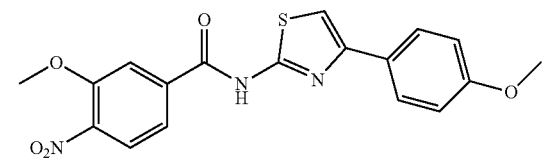

Exemplary compounds (Cpd) prepared according to General Synthetic Scheme 3 are shown below.

3-methoxy-N-(4-(4-methoxyphenyl)thiazol-2-yl)-4-nitrobenzamide (Cpd 76)

Example 75

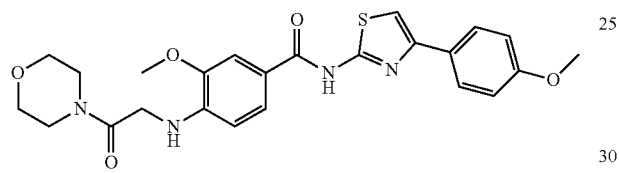

4-amino-3-methoxy-N-(4-(4-methoxyphenyl)thiazol-2-yl)benzamide (Cpd 77)

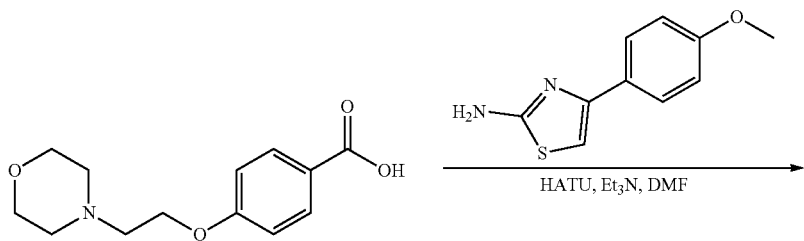

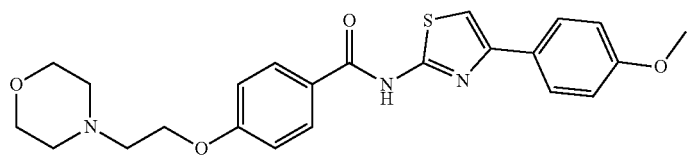

N-(4-(4-methoxyphenyl)thiazol-2-yl)-4-(2-morpholinoethoxy)benzamide (Cpd 78)

Exemplary compounds (Cpd) prepared according to General Synthetic Scheme 4 are shown below.

Example 79

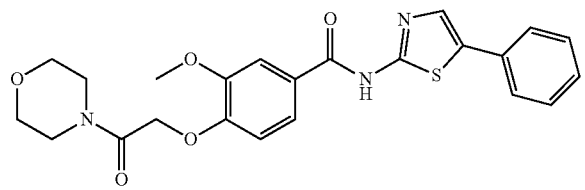 [SMILES: COc1cc(C(=O)Nc2ncc(-c3ccccc3)s2)ccc1OCC(=O)N1CCOCC1]

3-methoxy-4-(2-morpholino-2-oxoethoxy)-N-(5-phenylthiazol-2-yl)benzamide (Cpd 79)

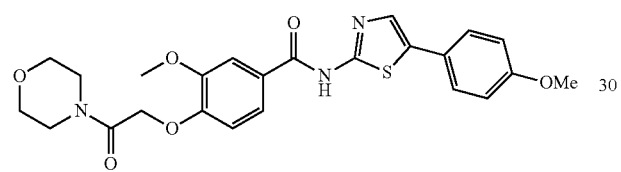

3-methoxy-N-(5-(4-methoxyphenyl)thiazol-2-yl)-4-(2-morpholino-2-oxoethoxy)benzamide (Cpd 80)

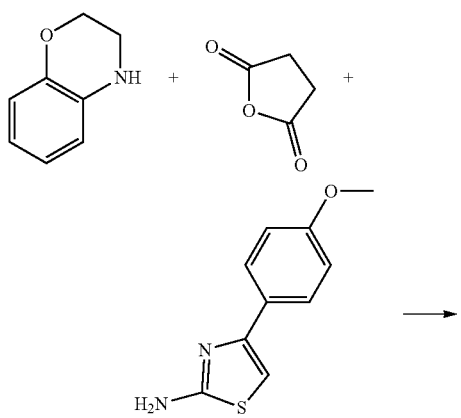

4-(2,3-dihydro-4H-benzo[b][1,4]oxazin-4-yl)-N-(4-(4-methoxyphenyl)thiazol-2-yl)-4-oxobutanamide (Cpd. 81)

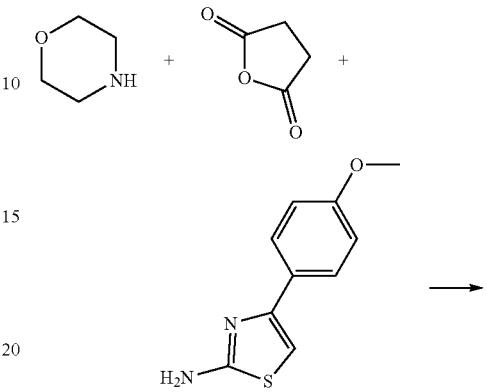

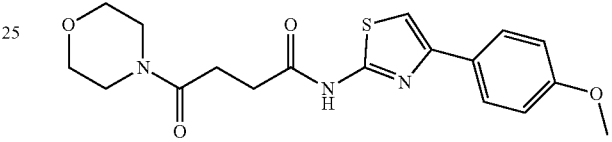

N-(4-(4-methoxyphenyl)thiazol-2-yl)-4-morpholino-4-oxobutanamide (Cp. 82)

Exemplary compounds (Cpd) prepared according to General Synthetic Scheme 5 are shown below.

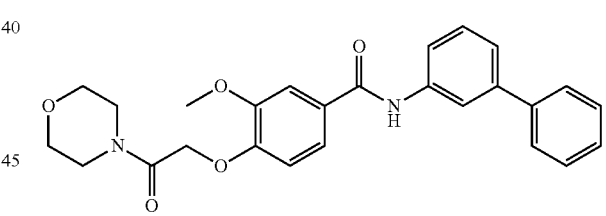

N-([1,1'-biphenyl]-3-yl)-3-methoxy-4-(2-morpholino-2-oxoethoxy)benzamide (Cpd. 83)

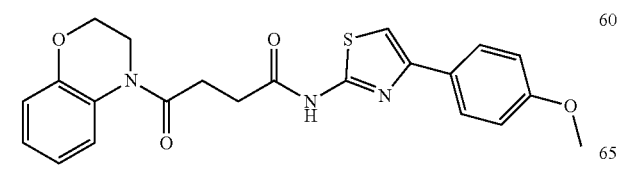

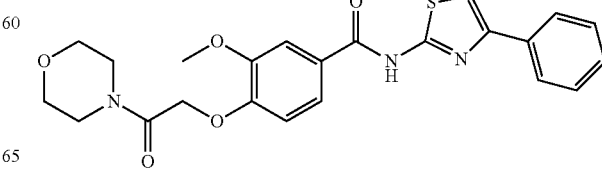

51
N-(5-benzyl-4-phenylthiazol-2-yl)-3-methoxy-4-(2-morpholino-2-oxoethoxy)benzamide (Cpd. 84)
52
N-(4-(4-methoxybenzyl)thiazol-2-yl)-4-(2-morpholino-2-oxoethoxy)benzamide (Cpd. 86)
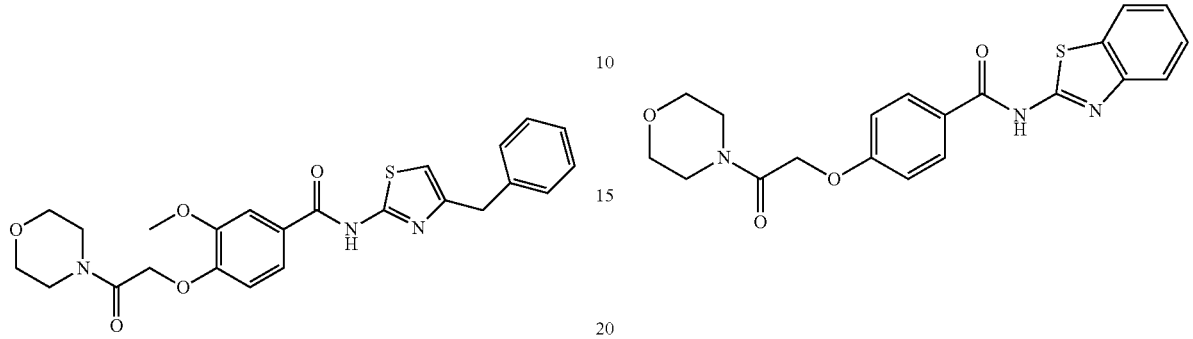
N-(benzo[d]thiazol-2-yl)-4-(2-morpholino-2-oxoethoxy)benzamide (Cpd. 87)
N-(4-benzylthiazol-2-yl)-3-methoxy-4-(2-morpholino-2-oxoethoxy)benzamide (Cpd. 85)
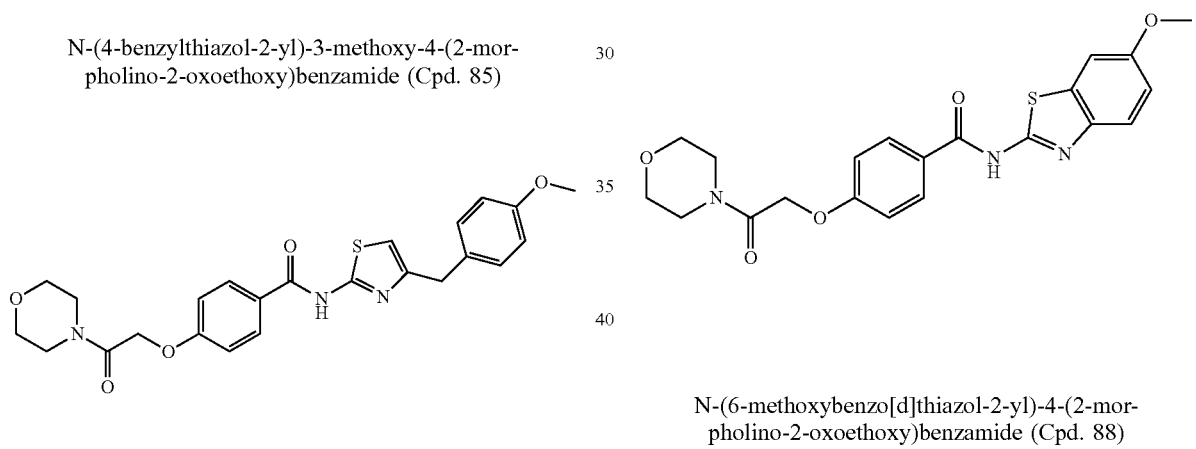
N-(6-methoxybenzo[d]thiazol-2-yl)-4-(2-morpholino-2-oxoethoxy)benzamide (Cpd. 88)
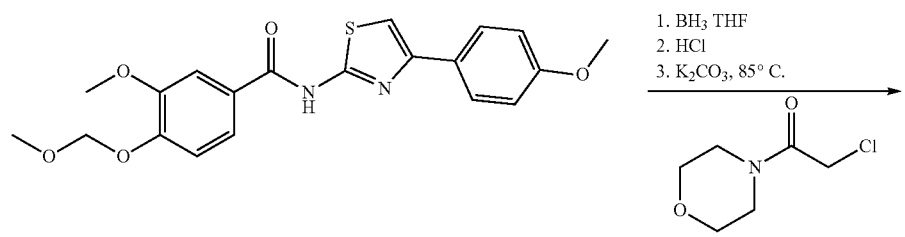
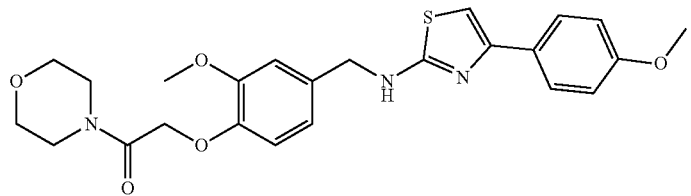

2-(2-methoxy-4-(((4-(4-methoxyphenyl)thiazol-2-yl)
amino)methyl)phenoxy)-1-morpholinoethan-1-one
(Cpd. 89)
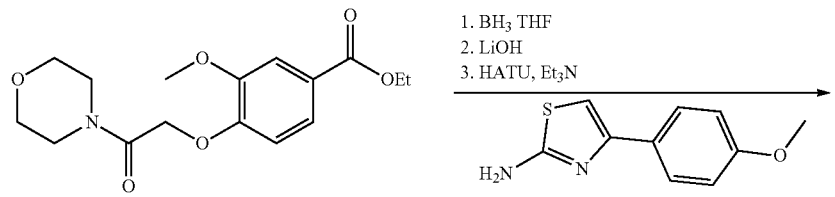
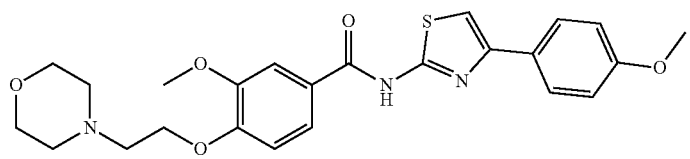
3-methoxy-N-(4-(4-methoxyphenyl)thiazol-2-yl)-4-
(2-morpholinoethoxy)benzamide (Cpd 90)
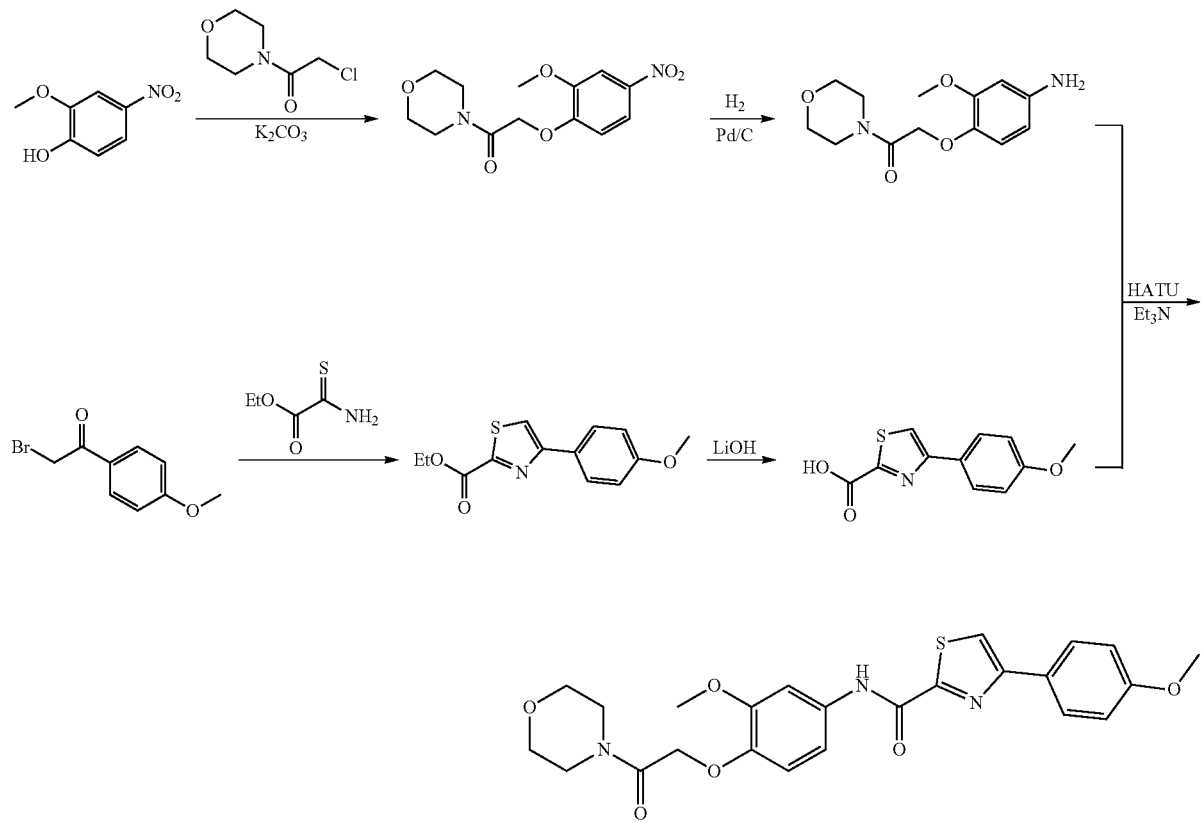

55

N-(3-methoxy-4-(2-morpholino-2-oxoethoxy)phenyl)-4-(4-methoxyphenyl)thiazole-2-carboxamide (Cpd 91)

Exemplary compounds (Cpd) prepared according to General Synthetic Scheme 6 are shown below.

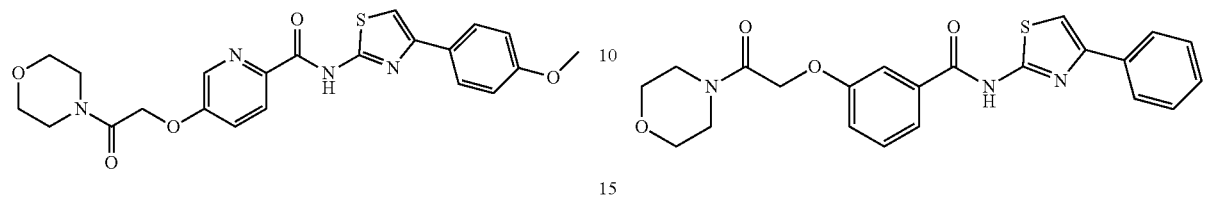

N-(4-(4-methoxyphenyl)thiazol-2-yl)-5-(2-morpholino-2-oxoethoxy)picolinamide (Cpd. 92)

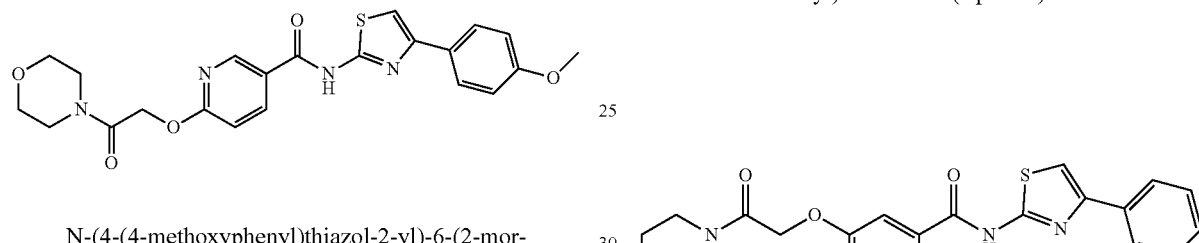

N-(4-(4-methoxyphenyl)thiazol-2-yl)-6-(2-morpholino-2-oxoethoxy)nicotinamide (Cpd. 93)

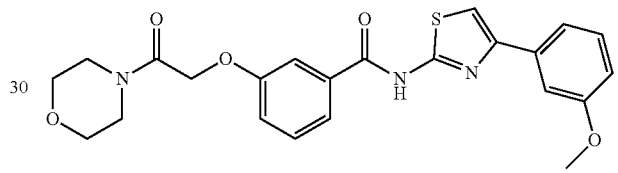

56

N-(4-(4-methoxyphenyl)thiazol-2-yl)-3-(2-morpholino-2-oxoethoxy)benzamide (Cpd. 94)

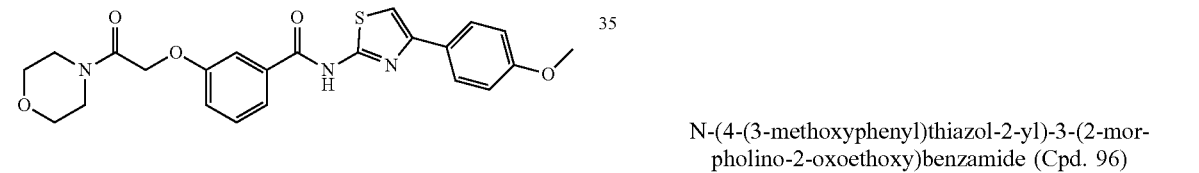

3-(2-morpholino-2-oxoethoxy)-N-(4-phenylthiazol-2-yl)benzamide (Cpd. 95)

N-(4-(3-methoxyphenyl)thiazol-2-yl)-3-(2-morpholino-2-oxoethoxy)benzamide (Cpd. 96)

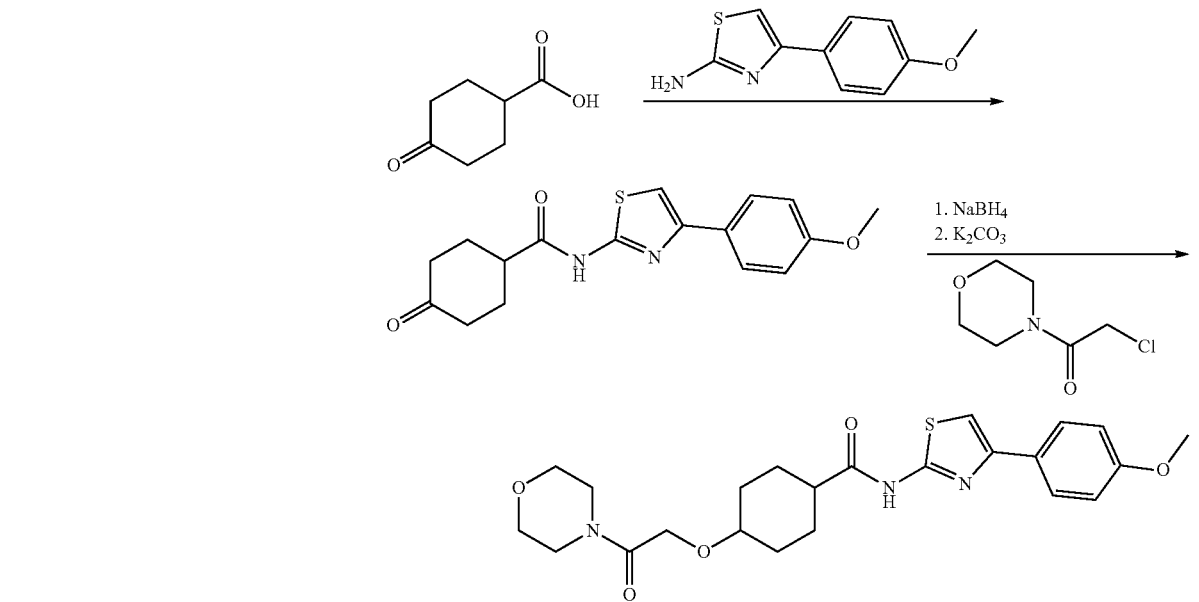

N-(4-(4-methoxyphenyl)thiazol-2-yl)-4-(2-morpholino-2-oxoethoxy)cyclohexane-1-carboxamide (Cpd. 97)
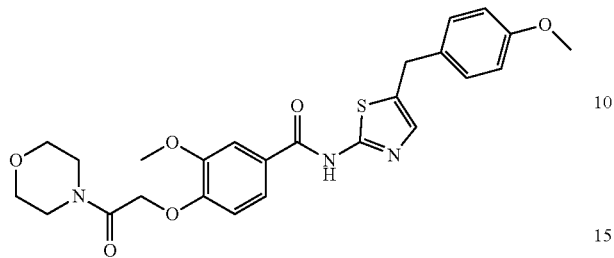
3-methoxy-N-(5-(4-methoxybenzyl)thiazol-2-yl)-4-(2-morpholino-2-oxoethoxy)benzamide (Cpd. 98)
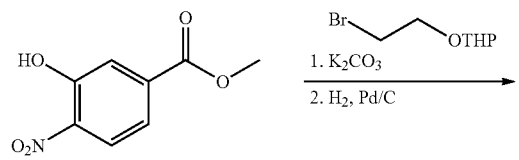
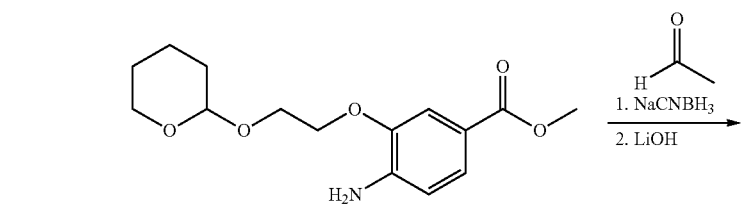
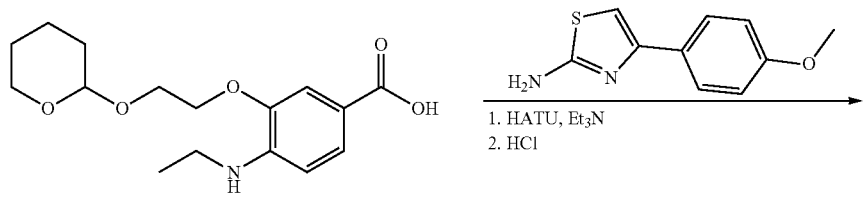
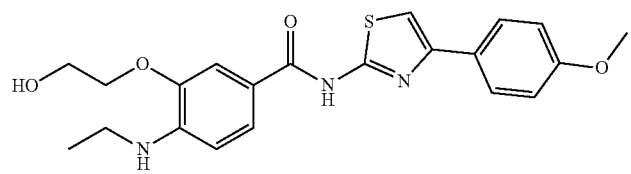

4-(ethylamino)-3-(2-hydroxyethoxy)-N-(4-(4-methoxyphenyl)thiazol-2-yl)benzamide (Cpd. 99)
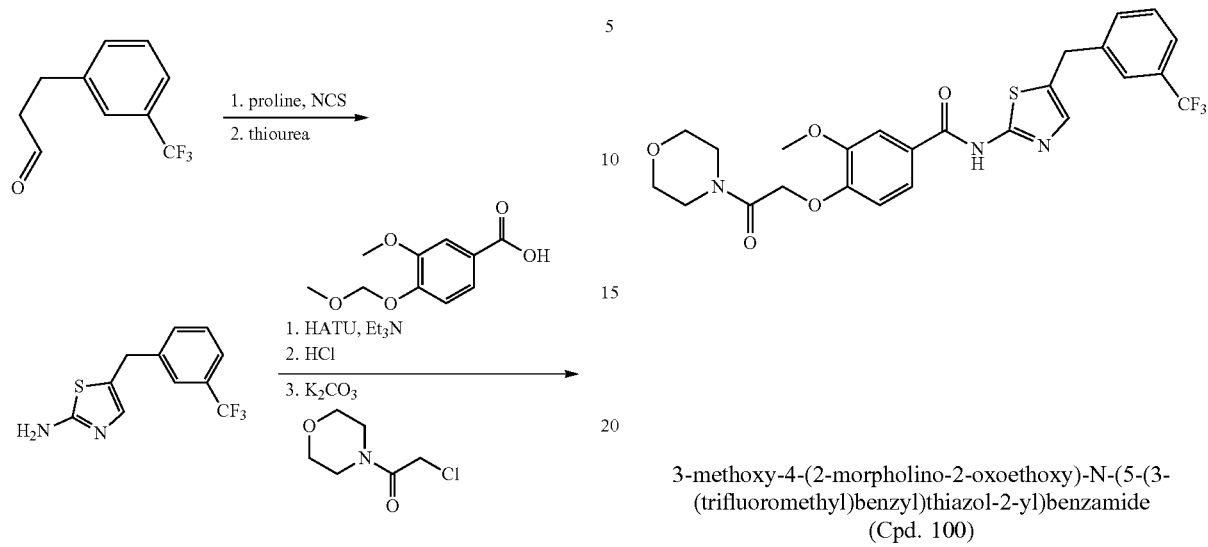
3-methoxy-4-(2-morpholino-2-oxoethoxy)-N-(5-(3-(trifluoromethyl)benzyl)thiazol-2-yl)benzamide (Cpd. 100)
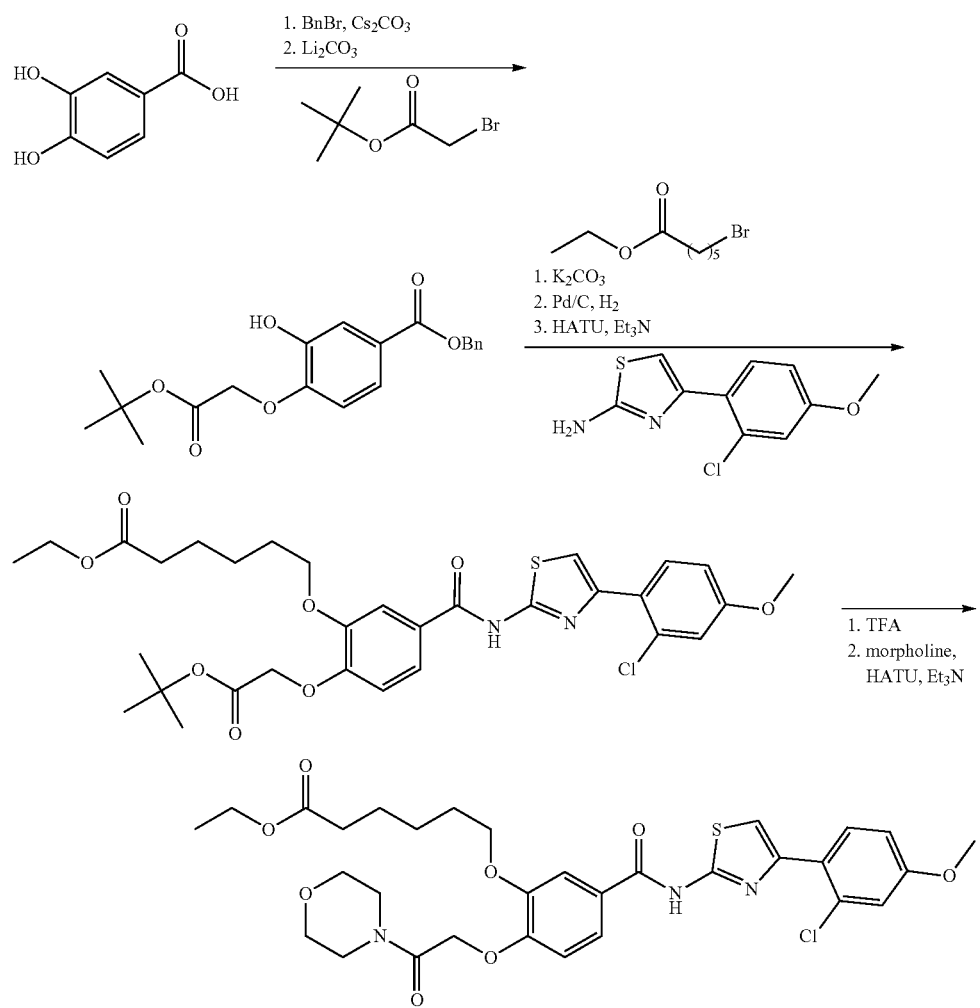

Ethyl 6-(5-((4-(2-chloro-4-methoxyphenyl)thiazol-2-yl)carbamoyl)-2-(2-morpholino-2-oxoethoxy) phenoxy)hexanoate (Cpd. 101)

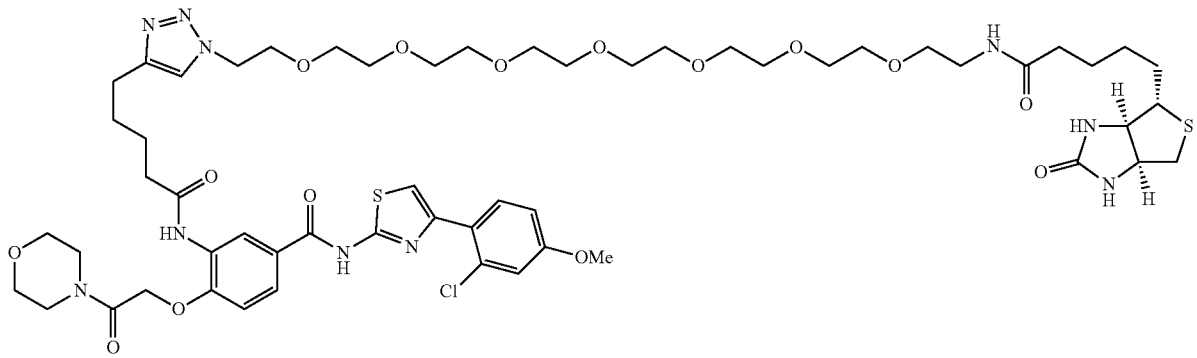 [SMILES: COc1ccc(-c2csc(NC(=O)c3ccc(OCC(=O)N4CCOCC4)c(NC(=O)CCCCc4cn(CCOCCOCCOCCOCCOCCOCCOCCNC(=O)CCCC[C@@H]5SC[C@H]6NC(=O)N[C@@H]56)nn4)c3)n2)c(Cl)c1]

N-(4-(2-chloro-4-methoxyphenyl)thiazol-2-yl)-4-(2-morpholino-2-oxoethoxy)-3-(5-(1-(25-oxo-29-43aR,4S,6aS)-2-oxohexahydro-1H-thieno[3,4-d]imidazol-4-yl)-3,6,9,12,15,18,21-heptaoxa-24-azanonacosyl)-1H-1,2,3-triazol-4-yl)pentanamido)benzamide (Cpd. 102)

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds. For example, any one or more of the compounds described herein, with a structure depicted herein, or referred to in the Tables or the Examples herein can be specifically included, excluded, or combined in any combination, in a set or subgroup of such compounds. Such specific sets, subgroups, inclusions, and exclusions can be applied to any aspect of the compositions and methods described here. For example, a set of compounds that specifically excludes one or more particular compounds can be used or applied in the context of compounds per se (for example, a list or set of compounds), compositions including the compound (including, for example, pharmaceutical compositions), any one or more of the disclosed methods, or combinations of these. Different sets and subgroups of compounds with such specific inclusions and exclusions can be used or applied in the context of compounds per se, compositions including one or more of the compounds, or any of the disclosed methods. All of these different sets and subgroups of compounds—and the different sets of compounds, compositions, and methods using or applying the compounds—are specifically and individual contemplated and should be considered as specifically and individually described. As an example, compound 7, compound 38, and compound 82 can be specifically included or excluded, as a group or individually, from any compounds per se (for example, a list or set of compounds), compositions including the compound (including, for example, pharmaceutical compositions), or any one or more of the disclosed methods, or combinations of these.

The compounds represented by Formula I can be optically active or racemic.

2. Salts and Derivatives

Also described herein are pharmaceutically acceptable nontoxic ester, amide, and salt derivatives of those compounds of formula (I) containing a carboxylic acid moiety.

Formula I also encompasses pharmaceutically acceptable salts. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula (I) to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

B. Protein/Peptide/Nucleic Acid Mondo Inhibitors

The disclosed composition can also include a Mondo family transcription factor inhibitor (herein, a Mondo inhibitor) which is a protein, peptide or nucleic acid molecule. In a preferred embodiment the family transcription factor is MondoA and/or MondoB (ChREBP). MondoA, also known as MLXIP (MLX interacting protein), KIAA0867 or MIR, is a 919 amino acid protein that localizes to the nucleus and the cytoplasm, as well as to the outer mitochondrial membrane, and contains one bHLH domain. Expressed in a variety of tissues with highest expression in skeletal muscle, MondoA functions as a dimeric structure that binds DNA at the canonical E box sequence 5'-CACGTG-3' and is involved in transcriptional activation and glucose-responsive gene regulation. Multiple isoforms of MondoA exist due to alternative splicing events (UniprotKB identifier Q9HAP2 (MLXIP HUMAN) which includes 5 isoforms: Q9HAP2-1 (the "canonical sequence"); Q9HAP2-2; Q9HAP2-3; Q9HAP2-4 or Q9HAP2-5 (Billin, et al., Mol. Cell. Biol. 20:8845-8854 (2000); Nagase, et al., DNA Res. 5:355-364 (1998); Genome Res. 14:2121-2127 (2004)).

Nucleic acid molecules that inhibit expression of a gene or nucleic acid can be referred to as "inhibitory nucleic acid" (referring to their composition). Inhibitory nucleic acid technologies are known in the art and include, but are not limited to, antisense oligonucleotides, catalytic nucleic acids such as ribozymes and deoxyribozymes, aptamers, triplex forming nucleic acids, external guide sequences, and RNA interference molecules (RNAi), particularly small nucleic acid molecules, such as short interfering nucleic acid (siNA), short interfering RNA (siRNA), double-stranded RNA (dsRNA), micro-RNA (mRNA), and short hairpin RNA (shRNA) molecules capable of mediating RNA interference (RNAi).

An inhibitory nucleic acid can reduce expression of a protein having the amino acid sequence of MondoA disclosed under UniprotKB accession no. Q9HAP2 (MLXIP HUMAN) (including Q9HAP2-1; Q9HAP2-2; Q9HAP2-3; Q9HAP2-4 or Q9HAP2-5;) or a variant thereof, collectively, "MondoA proteins") or ChREBP (MondoB) disclosed UniprotKB accession no. Q9NP71 (which include alternative splice variants disclosed under Q9NP71-1 ("canonical" sequence); Q9NP71-2; Q9NP71-3; Q9NP71-4; Q9NP71-5; or Q9NP71-6) or a variant thereof, collectively, "MondoB proteins". The inhibitory nucleic acid can reduce expression of an mRNA sequence encoding a MondoA or MondoB protein or genomic DNA encoding the mRNA.

i. Inhibitory Nucleic Acids

The expression or amount of MondoA (and/or MondoB) can be reduced in some cases using RNA interference, whereby double-stranded RNA (dsRNA, also referred to herein as siRNAs or ds siRNAs, for double-stranded small interfering RNAs) induces the sequence-specific degradation of targeted mRNA in cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which can be expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

In a preferred embodiment, the inhibitory nucleic acid is an siRNA. In one embodiment, the inhibitory nucleic acid has 100% sequence identity with at least a part of the target mRNA. However, inhibitory nucleic acids having 70%, 80% or greater than 90% or 95% sequence identity may be used. Thus sequence variations that might be expected due to genetic mutation, strain polymorphism, or evolutionary divergence can be tolerated. siRNA specific for MondoA and MondoB are commercially available. For example, MondoA siRNA (h) and ChREBP siRNA (h), each a pool of 3 target-specific 19-25 nt siRNAs designed to knock down gene expression of MondoA and MondoB respectively, is available from Santa Cruz Biotechnology, Inc. In addition, there are a number of companies that will generate interfering RNAs for a specific gene. Thermo Electron Corporation (Waltham, Mass.) has launched a custom synthesis service for synthetic short interfering RNA (siRNA). Each strand is composed of 18-20 RNA bases and two DNA bases overhang on the 3' terminus. Dharmacon, Inc. (Lafayette, Colo.) provides siRNA duplexes using the 2'-ACE RNA synthesis technology. Qiagen (Valencia, Calif.) uses TOM-chemistry to offer siRNA with high individual coupling yields (Li, et al., Nat. Med., 11(9):944-951 (2005).

In some forms the Mondo inhibitor is an antisense oligonucleotide. An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the Mondo or MondoB mRNA. Antisense nucleic acid sequences and delivery methods are well known in the art (Goodchild, Curr. Opin. Mol. Ther., 6(2):120-128 (2004); Clawson, et al., Gene Ther., 11(17):1331-1341 (2004)), which are incorporated herein by reference in their entirety. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In some forms the Mondo inhibitor is a ribozyme specific for a Mondo family transcription factor. Ribozymes are a type of RNA that can be engineered to enzymatically cleave and inactivate other RNA targets in a specific, sequence-dependent fashion. Ribozymes and methods for their delivery are well known in the art (Hendry, et al., BMC Chem. Biol., 4(1):1 (2004); Grassi, et al., Curr. Pharm. Biotechnol., 5(4):369-386 (2004); Bagheri, et al., Curr. Mol. Med., 4(5): 489-506 (2004); Kashani-Sabet M., Expert Opin. Biol. Ther., 4(11):1749-1755 (2004), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art.

In some forms, the Mondo inhibitor is a Triplex forming nucleic acid. Triplex forming nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Examples of how to make and use triplex forming molecules to bind a variety of different target molecules are known in the art.

In some forms, the Mondo inhibitor is an external guide sequences (EGSs). EGSs are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Examples of how to make and use EGS molecules to facilitate cleavage of a variety of different target molecules are known in the art.

ii. Antibodies

In some forms, the Mondo inhibitor can be an antibody. For example, the Mondo inhibitor can be an anti-MondoA or anti-MondoB antibody. For example, an anti-MondoA (or MondoB) antibody can be an antibody specific for MondoA (or MondoB), preferably, a monoclonal antibody. A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature,* 1975, 256:495-497, the disclosure of which is herein incorporated by reference. An exemplary hybridoma technology is described by Niman et al., *Proc. Natl. Acad. Sci. U.S.A.,* 1983, 80:4949-4953. Other methods of producing monoclonal antibodies, a hybridoma cell, or a hybridoma cell culture are also well known. See for example, Antibodies: A Laboratory Manual, Harlow et al., Cold Spring Harbor Laboratory, 1988; or the method of isolating monoclonal antibodies from an immunological repertoire as described by Sasatry, et al., *Proc. Natl. Acad. Sci. USA,* 1989, 86:5728-5732; and Huse et al., *Science,* 1981, 246:1275-1281.

iii. Aptamers

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules as well as large molecules, such as reverse transcriptase. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules are known in the art.

C. Formulations

The SBI-477 compounds and/or Mondo inhibitors described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients. See, e.g., *Remington's Pharmaceutical Sciences,* latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

These compositions can take the form of solutions, suspensions, emulsion, tablets, pills, capsules, powders, sustained-release formulations and the like.

1. Parenteral Formulations

The compounds described herein can be formulated for parenteral administration. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

If for intravenous administration, the compositions are packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachet indicating the amount of active agent. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine, and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

(a) Controlled Release Formulations

The parenteral formulations described herein can be formulated for controlled release including immediate release, delayed release, extended release, pulsatile release, and combinations thereof.

1. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In forms wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

2. Method of Making Nano- and Microparticles

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some forms, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some forms, drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above.

Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

(b) Injectable/Implantable Formulations

The compounds described herein can be incorporated into injectable/implantable solid or semi-solid implants, such as polymeric implants. In some forms, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

2. Enteral Formulations

Oral formulations can include standard carriers such as pharmaceutical grades of mannitol, lactose, sodium saccharine, starch, magnesium stearate, cellulose, magnesium carbonate, etc. Such compositions will contain a therapeutically effective amount of the compound and/or antibiotic together with a suitable amount of carrier so as to provide the proper form to the patient based on the mode of administration to be used. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

(a) Controlled Release Enteral Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another form, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another form, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

(1) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred forms, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred forms, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred form, the acrylic polymer is an acrylic resin lacquer such as that which is commercially available from Rohm Pharma under the tradename EUDRAGIT®. In further preferred forms, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(2) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers.

Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

III. Methods of Making and Using

Methods of making and using compounds disclosed herein are also disclosed.

A. Synthetic Methods

The compounds disclosed herein can be readily synthesized following the generic schemes outlined below and specific synthesis methods as disclosed in the Examples. In one aspect, a generic scheme for synthesizing the disclosed compounds is General Synthetic Scheme I.

General Synthetic Scheme 1

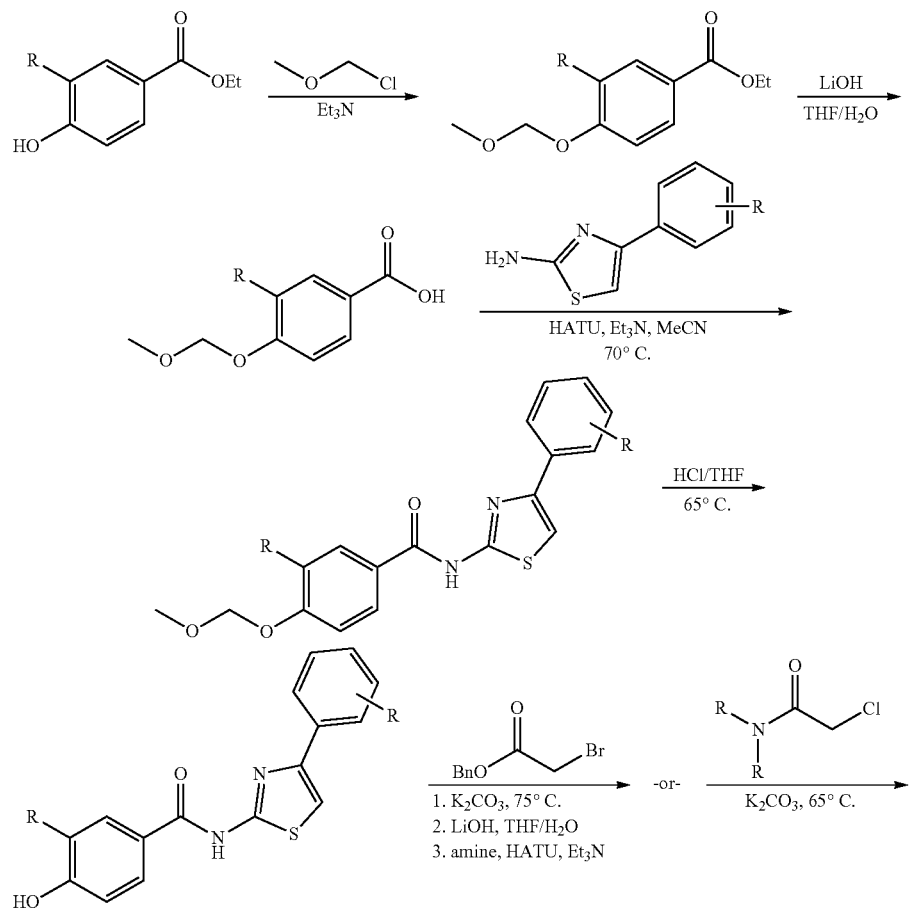

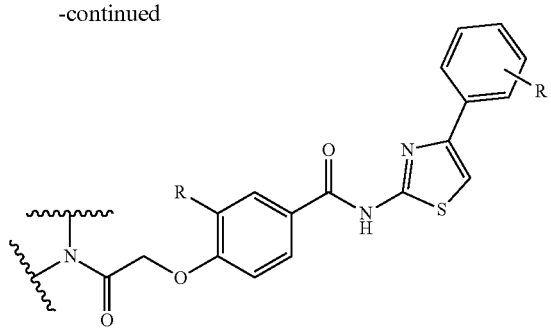

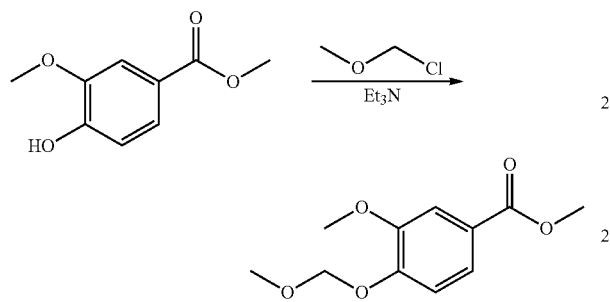

A round bottom flask is charged with ethyl 4-hydroxy-3-methoxybenzoate (4.95 g, 1.0 eq) and acetonitrile (100 mL). To this solution is then sequentially added NEt₃ (5.27 mL, 1.5 eq) and chloromethyl methylether (2.01 mL, 1.05 eq) and the resulting solution is stirred at 50° C. Additional Et₃N and MOMCl are added as necessary to drive the reaction to completion. Upon completion, the solution is cooled to room temperature and partially concentrated. The solution is then diluted with EtOAc and sequentially washed with ammonium chloride (aq.), water, and brine. The organic portion is dried over sodium sulfate and concentrated in vacuo to give ethyl 3-methoxy-4-(methoxymethoxy)benzoate (6.06 g) as a pale yellow oil which is used without further purification. $^{1}$H NMR (500 MHz, Chloroform-d) δ 7.57 (dd, J=8.5, 2.0 Hz, 1H), 7.51 (d, J=2.0 Hz, 1H), 7.09 (d, J=8.4 Hz, 1H), 5.21 (s, 2H), 4.29 (q, J=7.2 Hz, 2H), 3.86 (s, 3H), 3.43 (s, 3H), 1.31 (t, J=7.2 Hz, 3H).

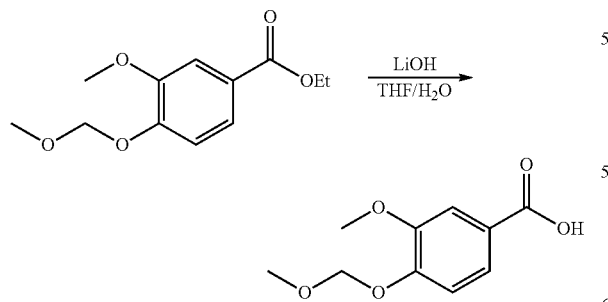

A round bottom flask is charged with ethyl 3-methoxy-4-(methoxymethoxy)benzoate (6.06 g, 1.0 eq), THF (30 mL) and water (15 mL). To this solution is then added LiOH (2.4 g, 4.0 eq) and the resulting mixture is warmed to 65° C. Upon completion of the reaction (by LCMS), the solution is cooled to room temperature, treated with a 10% citric acid solution and thrice extracted with EtOAc. The combined organic portions are washed with brine and dried over sodium sulfate. Concentration in vacuo gives 3-methoxy-4-(methoxymethoxy)benzoic acid (3.99 g, 75% yield) as a white solid which is clean by NMR. mp=158-160° C. $^{1}$H NMR (500 MHz, Chloroform-d) δ 7.76 (dd, J=8.5, 1.9 Hz, 1H), 7.66 (d, J=2.0 Hz, 1H), 7.23 (d, J=8.4 Hz, 1H), 5.34 (s, 2H), 3.98 (s, 3H), 3.55 (s, 3H).

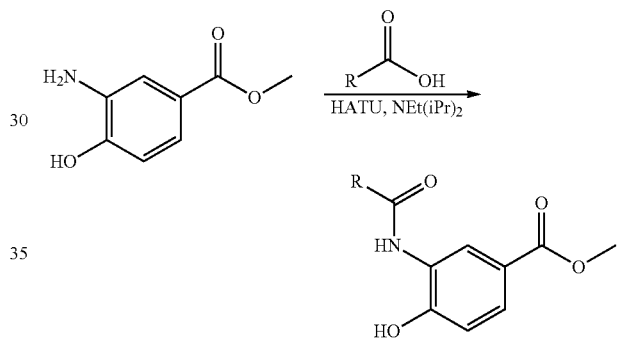

HATU (3.0 eq) is weighed into a vial and dry acetonitrile (0.2 M) is added. A carboxylic acid (1.05 eq) is added followed by Hünig's base (3.0 eq). The mixture is stirred at 23° C. for 5 min before the addition of methyl 3-amino-4-hydroxybenzoate (1.0 eq). After stirring for 18 h at 23° C., the reaction is diluted with dichloromethane and extracted with 1N HCl, sat. NaHCO₃ solution (2×) and brine. The organic layer is dried over anhydrous Na₂SO₄ and evaporated. The residue is chromatographed by silica gel flash chromatography and elution with 0-20% ethyl acetate in hexanes to give the expected N-acylated product.

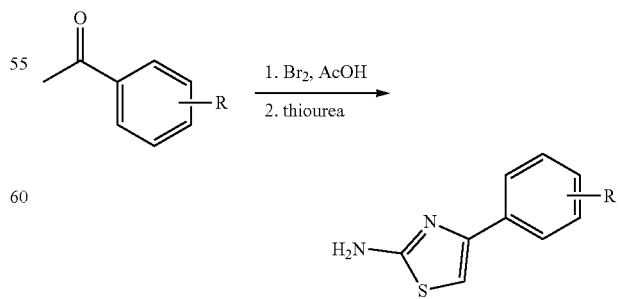

A flask is charged with an acetophenone (1.0 eq) and THF (1.0 M, 2 mL). The solution is then diluted with chloroform (0.33 M, 6 mL) and AcOH (0.065 mL). Br₂ (1.1 eq) is then slowly added to the solution (an ice bath was used for larger scale reactions). The solution is stirred until the characteristic bromine color faded (~30 min). To the solution is then added thiourea (1.5 eq) and the resulting mixture stirred overnight (~18 h). The resulting mixture contains a precipitate which is collected via filtration, washing sequentially with dichloromethane and water. The solid is dissolved in THF and concentrated in vacuo to aid in drying. The resulting 2-aminothiazole is used without further purification.

to 70° C. Stirring at 70° C. is continued until full consumption of the carboxylic acid by LCMS. The solution is cooled to room temperature, diluted with EtOAc, and thrice washed with water. Concentration in vacuo gives an oil that was is without further purification. This oil is directly dissolved in THF (4 mL) and treated with 1N HCl (1 mL). The solution is warmed to 65° C. and stirred until the acetal deprotection is complete by LCMS. Upon completion, the solution is cooled to room temperature, diluted with EtOAc and sequentially washed with water and brine. Concentration and purification on silica gel (hex/EtOAc gradient 5-50%) gives the clean phenol as a white solid.

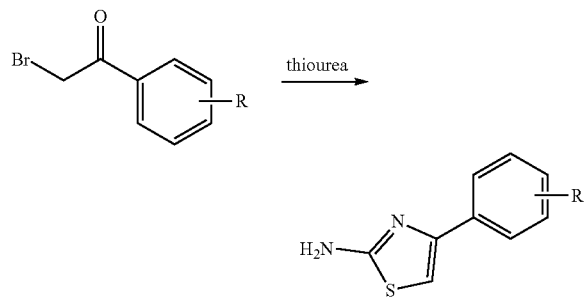

A microwave vial is charged with an α-bromoacetophenone (1.0 eq) and 1:1 EtOH/water (0.5 M). Thiourea (1.1 eq) is added, and the mixture warmed in the microwave reactor at 75° C. for 30 min. Upon completion, the room temperature solution contains a precipitate which could be collected via filtration (washing with water), and dried to give the desired 2-aminothiazole.

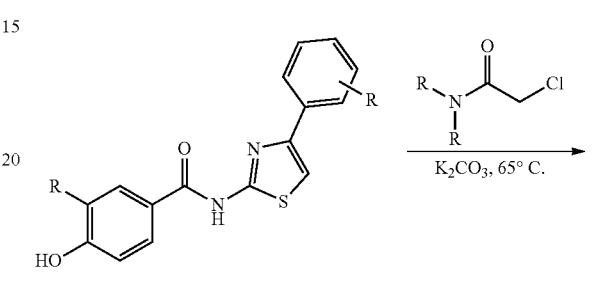

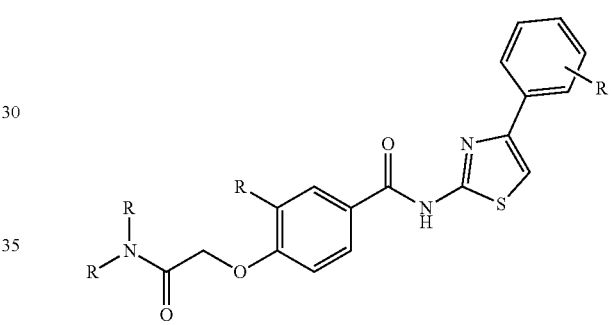

A vial is charged with the appropriate phenol (1.0 eq) and DMF (0.1 M). Potassium carbonate (3.0 eq) is added, followed by an α-chloroacetamide (1.1 eq). This solution is warmed to 70° C. and stirred until complete by LCMS (~2-4 h). Upon completion, the solution is cooled to room temperature and diluted with water. In most instances, the addition of water initiated the precipitation of the product from the solution, which could then be collected via filtration (washing with water). If precipitation does not occur, then the reaction is diluted with EtOAc, thrice washed with water, and concentrated. Purification of either the concentrated material, or the precipitated solid is performed either on silica gel (hex/EtOAc gradient 50%-100%) or mass-triggered, reverse phase preparative HPLC (water/MeCN gradient).

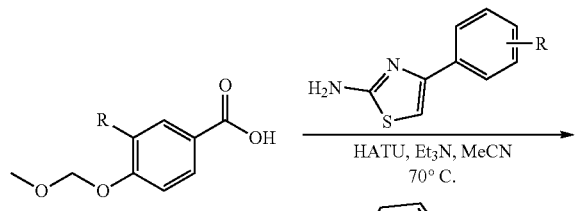

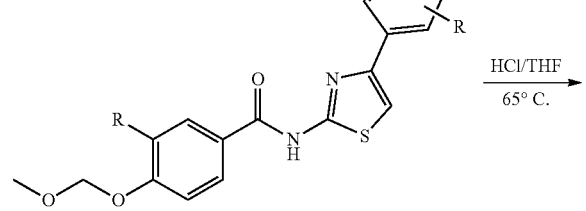

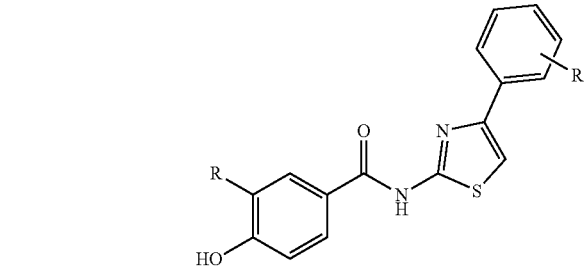

A vial is charged with the 2-aminothiazole (1.0 eq), triethylamine (3.0 eq), and acetonitrile (~0.4 M). To this solution is added the acetal-protected carboxylic acid (1.0 eq). Finally, HATU (1.0 eq) is added and the vial is warmed

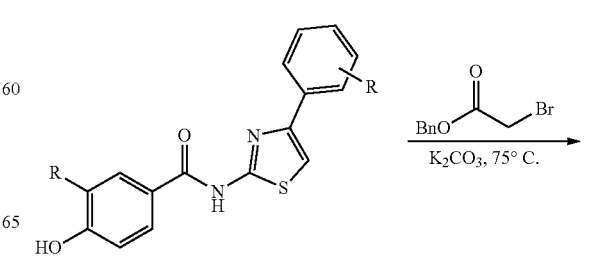

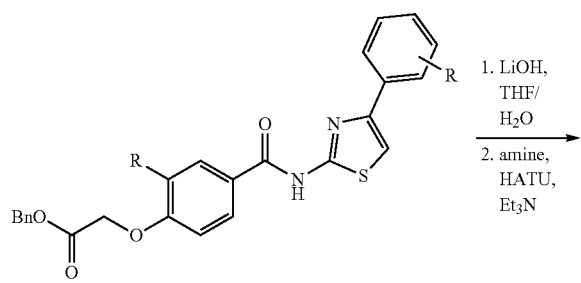

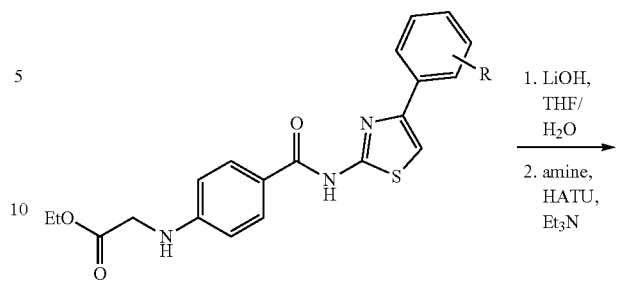

A vial is charged with an appropriate phenol (1.0 eq) and potassium carbonate (2.0 eq) in acetonitrile (0.2 M). To this mixture is added an α-bromoacetate (1.05 eq), which is warmed to 75° C. Upon completion (~1 h), the solution is decanted from the remaining carbonate salts and then purified directly on silica gel (hex/EtOAc gradient 5%-60%) to give the intermediate ester as a tan solid. This material (1.0 eq) is added to a solution of THF (3 mL) and water (1.5 mL). LiOH is then added (4 eq) and stirred at room temperature until the saponification is complete (1.5 h). The solution is quenched with 1N HCl and twice extracted with EtOAc. The combined organic portions are dried over sodium sulfate and concentrated in vacuo to give the expected carboxylic acid as a white solid. This carboxylic acid (1.0 eq) is dissolved in DMF (0.1 M) and treated with triethylamine (2.0 eq) and various amines (1.2 eq). Lastly, HATU (1.2 eq) is added and stirred for 60 min. At this time the reaction is complete and the solution is purified directly on a reverse phase preparatory HPLC to give the corresponding amides as white solids.

In another aspect, a generic scheme for synthesizing the disclosed compounds is General Synthetic Scheme 2.

General Synthetic Scheme 2

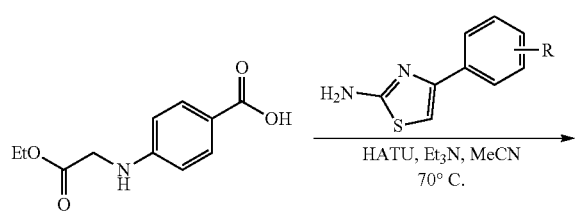

The commercially available 4-((2-ethoxy-2-oxoethyl)amino)benzoic acid (1.0 eq) is dissolved in acetonitrile (0.3 M) and treated with triethylamine (4.0 eq) and a 2-aminothiazole (1.0 eq). To this mixture is added HATU (1.5 eq). The resulting solution is warmed to 75° C. and stirred until the reaction was complete. At this time the solution is cooled to room temperature and diluted with EtOAc. The solution is sequentially washed with water (2×) and brine, dried over sodium sulfate, and then concentrated in vacuo. Purification on silica gel (hex/EtOAc gradient 10%-100%) gives an impure mixture which could be dissolved in DMF and precipitated by the addition of water. This solid is dissolved in THF:H$_2$O (3:1) and treated with LiOH (4.0 eq). Saponification is completed within one hour of stirring at room temperature. The solution is then diluted with EtOAc and washed with a 10% citric acid solution followed by brine. Drying on sodium sulfate and concentration gives a colored solid which is then washed with a dichloromethane and methanol solution to give the intermediate carboxylic acid as an off-white solid. This carboxylic acid (1.0 eq) is dissolved in DMF (0.25 M). Triethylamine (2.0 eq) and an amine (4.0 eq) are then added. Lastly, HATU (1.2 eq) is added and the solution is stirred at room temperature until the reaction is complete. Water is then slowly added to the reaction which then formed a precipitate. This precipitate was collected via filtration and washed with a mixture of THF and methanol to cleanly the expected amide. If precipitation did not occur, then the mixture could be purified via reverse phase HPLC to give the expected product.

In another aspect, a generic scheme for synthesizing the disclosed compounds is General Synthetic Scheme 3.

General Synthetic Scheme 3

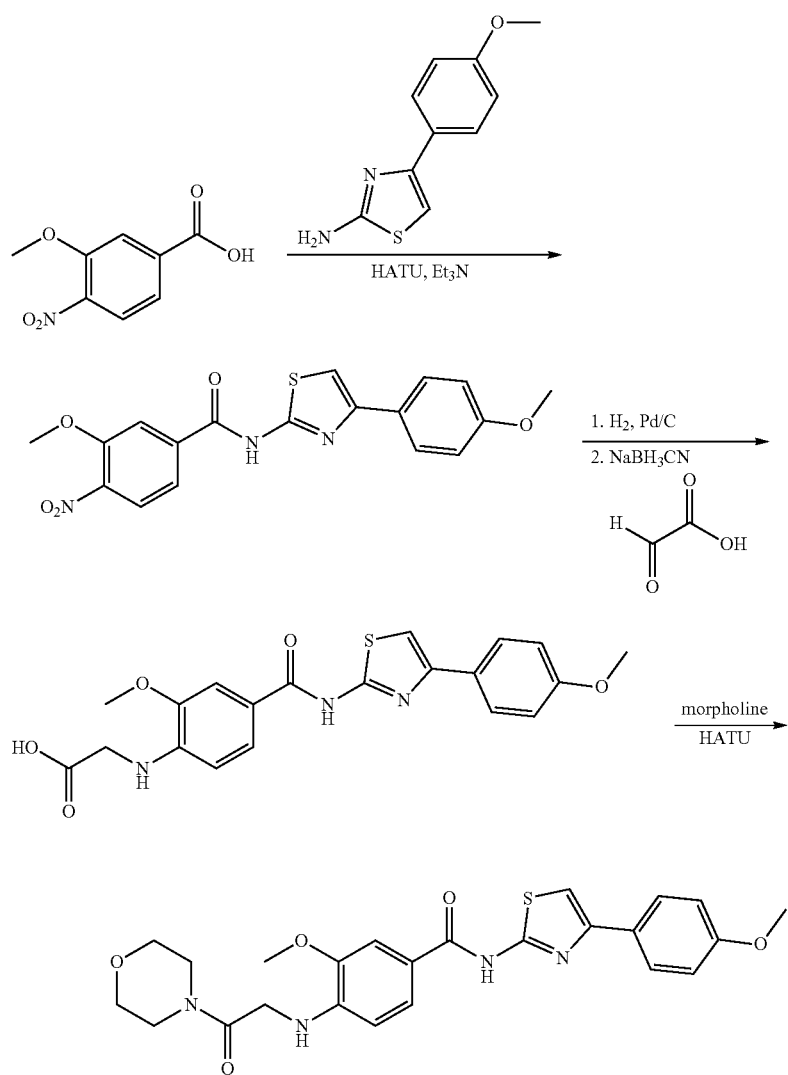

The commercially available 3-methoxy-4-nitrobenzoic acid (1.0 eq) is dissolved in acetonitrile (0.25 M) and treated with triethylamine (2.0 eq) and HATU (1.0 eq). To this mixture is added 4-(4-methoxyphenyl)thiazol-2-amine (1.0 eq). The resulting solution is warmed to 65° C. and stirred until the reaction is complete. At this time the solution is cooled to room temperature and diluted with water. The resulting precipitate was collected via filtration, washed with additional water, and dried in vacuo to give 3-methoxy-N-(4-(4-methoxyphenyl)thiazol-2-yl)-4-nitrobenzamide as a pale yellow solid (82% yield). A dry round bottom flask is charged with 10% palladium on carbon (0.05 eq) under an atmosphere of nitrogen. EtOAc (~0.2 M) is then added, followed by 3-methoxy-N-(4-(4-methoxyphenyl)thiazol-2-yl)-4-nitrobenzamide (1.0 eq). A hydrogen-filled balloon is then affixed to the flask and the airspace was evacuated and back-filled with hydrogen. The mixture is vigorously stirred until the reaction was complete, adding additional catalyst as needed and some methanol to ensure solubility. The mixture is then filtered through celite, washing with methanol to give 3-methoxy-N-(4-(4-methoxyphenyl)thiazol-2-yl)-4-nitrobenzamide as a yellow solid. This solid (1.0 eq) is then dissolved in acetonitrile (0.1 M) and treated with excess glyoxylic acid (~15 eq of a 50% aqueous solution). Sodium cyanoborohydride (5.0 eq) is added and stirred at room temperature until the reaction was complete. The solution is quenched with acetic acid, and partitioned between EtOAc and 1N HCl. The organic portion is concentrated to a yellow solid that is used without further purification. The crude (2-methoxy-4-((4-(4-methoxyphenyl)thiazol-2-yl)carbamoyl) phenyl)glycine (1.0 eq) is dissolved in DMF and treated with morpholine (10.0 eq). To this room temperature solution is added HATU (3.0 eq) and stirring is continued until the reaction is complete. The solution is then quenched with water which initiates the formation of a white precipitate. This impure solid is collected via filtration and then purified on silica gel (hexane/EtOAc gradient 35%-100%) to give 3-methoxy-N-(4-(4-methoxyphenyl)thiazol-2-yl)-4-((2-morpholino-2-oxoethyl)amino)benzamide as a white solid. Other compounds can be prepared using this generic scheme as exemplified herein.

In still another aspect, a generic scheme for synthesizing the disclosed compounds is General Synthetic Scheme 4.

General Synthetic Scheme 4

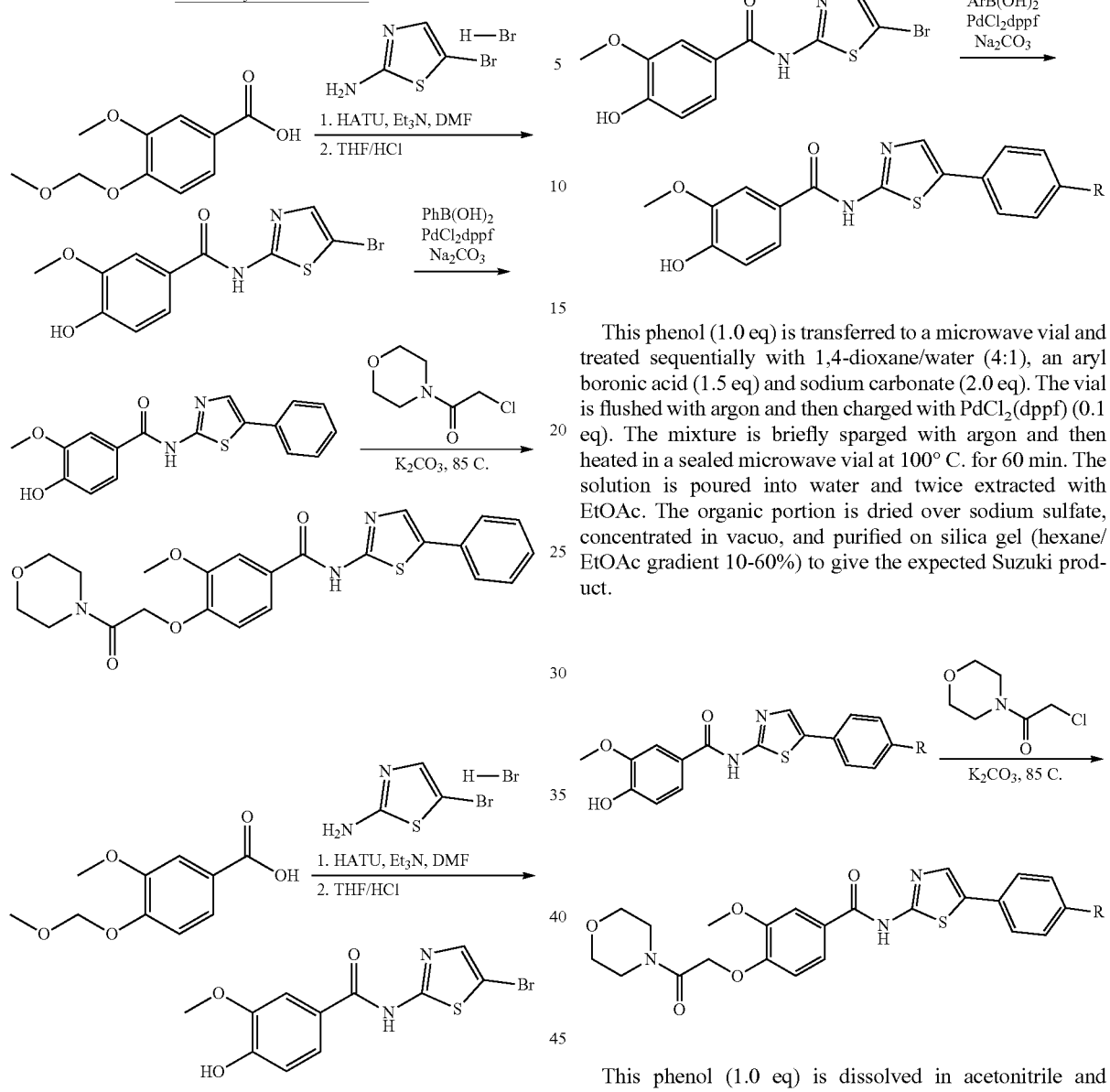

A vial is charged with the 5-bromothiazol-2-amine hydrobromide (1.0 eq), triethylamine (3.0 eq), and DMF (~0.2 M). To this solution is added the 3-methoxy-4-(methoxymethoxy)benzoic acid (1.2 eq). Finally, HATU (1.2 eq) is added and the vial was warmed to 75° C. Stirring at 75° C. is continued until full consumption of the carboxylic acid by LCMS. The solution is then cooled to room temperature, diluted with EtOAc, and washed with brine. The solution is concentrated in vacuo and was used without further purification. This material is dissolved in THF (4 mL) and treated with 1N HCl (1 mL). The solution is then warmed to 65° C. and stirred until the acetal deprotection was complete by LCMS. Upon completion, the solution was cooled to room temperature, diluted with EtOAc and sequentially washed with NaHCO$_3$ and brine. The solution is concentrated in vacuo, and purified on silica gel (hex/EtOAc gradient 10-75%) to give the clean phenol as a white solid.

This phenol (1.0 eq) is transferred to a microwave vial and treated sequentially with 1,4-dioxane/water (4:1), an aryl boronic acid (1.5 eq) and sodium carbonate (2.0 eq). The vial is flushed with argon and then charged with PdCl$_2$(dppf) (0.1 eq). The mixture is briefly sparged with argon and then heated in a sealed microwave vial at 100° C. for 60 min. The solution is poured into water and twice extracted with EtOAc. The organic portion is dried over sodium sulfate, concentrated in vacuo, and purified on silica gel (hexane/EtOAc gradient 10-60%) to give the expected Suzuki product.

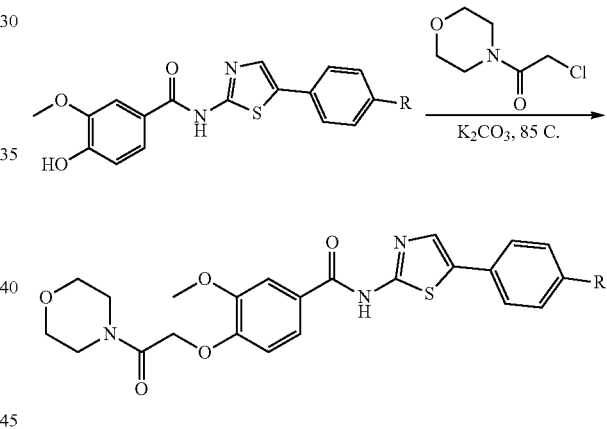

This phenol (1.0 eq) is dissolved in acetonitrile and treated with potassium carbonate (2.0 eq). Lastly, 2-chloro-1-morpholinoethan-1-one (1.0 eq) is added and this solution warmed to 85° C. and stirred for 4 h. The solution is cooled to room temperature and the inorganic salts are removed via filtration. The solution is then purified either on reverse phase preparatory HPLC, or silica gel to give the expected product as a white solid.

In still another aspect, a generic scheme for synthesizing the disclosed compounds is General Synthetic Scheme 5.

General Synthetic Scheme 5

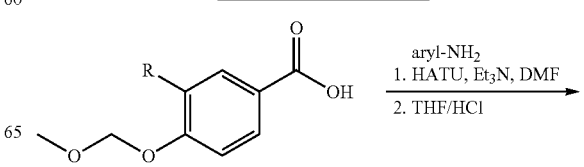

-continued

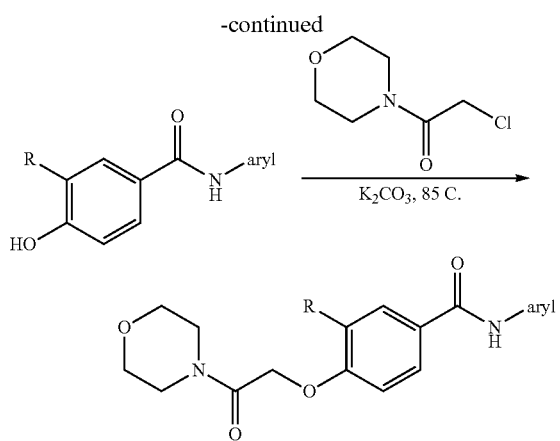

In still another aspect, a generic scheme for synthesizing the disclosed compounds is General Synthetic Scheme 6.

General Synthetic Scheme 6

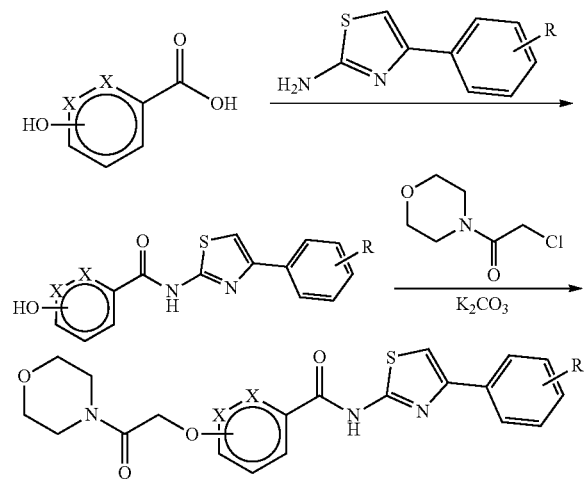

B. Administration

The compounds described herein can be administered in an effective amount to a subject that is in need of alleviation or amelioration from one or more symptoms associated with cellular lipotoxicity or insulin resistance. Additionally, the data disclosed herein shows that SBI-993 treatment resulted in a small but significant reduction in body weight as compared to vehicle. Accordingly, method for reducing body weight in a subject in need thereof, are also contemplated and disclosed.

As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation. The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The compositions are administered in an effective amount and for a period of time effect to reduce one or more symptoms associated with the disease to be treated. Exemplary symptoms include, but are not limited to higher than normal blood glucose levels or higher than normal cellular lipid/TAG levels. It is within the abilities of one of ordinary skill in the art to determine higher than normal blood glucose cellular lipid/TAG levels, which are used herein to refer to levels found in a healthy individual.

In preferred forms, patients to be treated include those with noninsulin dependent diabetes mellitus (NIDDM or Type II diabetes), insulin dependent diabetes mellitus (IDDM or Type I diabetes), insulin resistance such as impaired glucose tolerance. Insulin resistance is defined as a state in which circulating insulin levels in excess of the normal response to a glucose load are required to maintain the euglycemic state (Ford et al. *JAMA* (2002) 287:356-9). Insulin resistance, and the response of a subject with insulin resistance to therapy, may be quantified by assessing the homeostasis model assessment to insulin resistance (HOMA-IR) score, a reliable indicator of insulin resistance (Katsuki, et al. *Diabetes Care* 2001; 24:362-5,). The estimate of insulin resistance by the homeostasis assessment model (HOMA)-IR score is calculated with the formula (Galvin, et al. *Diabet Med* 1992; 9:921-8): HOMA-IR= [fasting serum insulin (μU/mL)]×[fasting plasma glucose (mmol/L)/22.5]. Subjects with a predisposition for the development of impaired glucose tolerance (IGT) or type 2 diabetes are those having euglycemia with hyperinsulinemia are by definition, insulin resistant. A typical subject with insulin resistance is usually overweight or obese.

However, the compositions disclosed herein can be administered to subjects with any disorder associated with cellular lipotoxicity, abnormally increased TAG synthesis and/or deposition; etc. or subjects who can benefit from increasing insulin sensitivity and/or increased cellular glucose uptake, Examples include subjects with obesity, including insulin resistant obesity, obesity or diabetes-related heart disease (including atheromatous disease), metabolic syndrome, non-alcoholic fatty liver disease including hepatic steatosis and nonalcoholic steatohepatitis, triglyceride storage disease, dysfunctions associated with lipid biosynthesis and triglyceride levels, as seen for example in renal lipotoxicity-associated inflammation, diabetic nephropathy, pancreatic beta cell lipotoxicity-induced dysfunction (*Diabetes*, 50(Suppl 1:S118-21 (2001).

The compounds disclosed herein are potent inhibitors of MondoA. Carroll, et al. identified a critical role for lipid biosynthesis in survival of Myc-driven cancer requiring MondoA in different cancer types including neuroblastoma, lung squamous cell carcinoma/lung adenocarcinoma, liver hepatocellular carcinoma, colon adenocarcinoma, acute myeloid leukemia, and breast invasive carcinoma. Carroll, et al., *Cancer Cell,* 2015; 27(2):271-285). Their studies showed that knockdown of MondoA significantly reduces survival of human B cells expressing c-Myc. Accordingly, methods for reducing MondoA activity/function within the context of Myc-driven cancers are also contemplated and disclosed herein.

The present invention will be further understood by reference to the following non-limiting examples.

Examples

Materials and Methods

Cell Culture

Primary human skeletal myoblasts, kindly provided by Dr. Steven Smith (Translational Research Institute for Metabolism and Diabetes, Florida Hospital, Orlando, Fla.), were isolated and cultured from lean healthy male subjects obtained by muscle biopsy. Myoblasts were grown to approximately 80-90% confluence and differentiated into myotubes as previously described (Sparks, et al., *PLoS One*, 2011; 6(7):e21068). Rat heart myoblast H9c2 cells (ATCC) were maintained in Dulbecco's modified Eagle medium (DMEM) containing 10% fetal bovine serum (FBS) in a 5% $CO_2$ incubator. At approximately 80-90% confluence, H9c2 myoblasts were differentiated into myotubes by culturing in DMEM supplemented with 1% FBS for 4-5 days.

Fatty Acid Oxidation (FAO) Assay

FAO rates were determined for primary human skeletal myotubes with or without SBI-477 using 125 µM [3H]-palmitic acid (Djouadi, et al., *Mol Genet Metab.* 2003; 78(2):112-118). Primary human skeletal myotubes were grown and differentiated in 24-well plates. Cells were treated with the indicated concentration of SBI-477 for 24 hours. Following compound treatment, cells were rinsed three times with PBS and then incubated in 125 µM [3H]-palmitic acid (60 Ci/mmol) bound to fatty acid free albumin containing 1 mM carnitine for 2 hours at 37° C. The cell medium was transferred to a tube containing cold 10% trichloroacetic acid (TCA). The tubes were centrifuged at 8,500×g for 10 minutes at 4° C. The supernatant was immediately removed, mixed with 6N NaOH, and applied to ion-exchange resin (DOWEX 1; Sigma-Aldrich). The eluate was collected, measured by liquid scintillation analyzer (PerkinElmer) and normalized to total protein amount. The amount of cell protein was measured by Micro BCA protein assay kit (Thermo Scientific).

SBI-477 and SBI-993 Synthesis

Synthesis Route for SBI-477

A round bottom flask was charged with ethyl 4-hydroxy-3-methoxybenzoate (4.95 g, 1.0 eq) and acetonitrile (100 mL). To this solution was then sequentially added NEt3 (5.27 mL, 1.5 eq) and chloromethyl methylether (2.01 mL, 1.05 eq); the resulting solution was stirred at 50° C. Additional Et3N and MOMCl were added as necessary to drive the reaction to completion. Upon completion, the solution was cooled to room temperature and partially concentrated. The solution was then diluted with EtOAc and sequentially washed with aqueous ammonium chloride, water, and brine. The organic portion was dried over sodium sulfate and concentrated in vacuo to give ethyl 3-methoxy-4-(methoxymethoxy)benzoate (6.06 g) as a pale yellow oil which was used without further purification. 1H NMR (500 MHz, Chloroform-d) δ 7.57 (dd, J=8.5, 2.0 Hz, 1H), 7.51 (d, J=2.0 Hz, 1H), 7.09 (d, J=8.4 Hz, 1H), 5.21 (s, 2H), 4.29 (q, J=7.2 Hz, 2H), 3.86 (s, 3H), 3.43 (s, 3H), 1.31 (t, J=7.2 Hz, 3H).

A round bottom flask was charged with ethyl 3-methoxy-4-(methoxymethoxy)benzoate (6.06 g, 1.0 eq), THF (30 mL) and water (15 mL). To this solution was then added LiOH (2.4 g, 4.0 eq) and the resulting mixture was warmed to 65° C. Upon completion of the reaction (by LCMS), the solution was cooled to room temperature, treated with a 10% citric acid solution and thrice extracted with EtOAc. The combined organic portions were washed with brine and dried over sodium sulfate. Concentration in vacuo gave 3-methoxy-4-(methoxymethoxy)benzoic acid (3.99 g, 75% yield) as a white solid which was pure by NMR. mp=158-160° C. 1H NMR (500 MHz, Chloroform-d) δ 7.76 (dd, J=8.5, 1.9 Hz, 1H), 7.66 (d, J=2.0 Hz, 1H), 7.23 (d, J=8.4 Hz, 1H), 5.34 (s, 2H), 3.98 (s, 3H), 3.55 (s, 3H).

A vial was charged with 4-(4-methoxyphenyl)thiazol-2-amine (412 mg, 1.0 eq), triethylamine (558 µL, 2.0 eq), and acetonitrile (~0.4 M). To this solution was then added 3-methoxy-4-(methoxymethoxy)benzoic acid (509 mg, 1.2 eq). Finally, HATU (912 mg, 1.0 eq) was added and the vial was warmed to 75° C. Stirring at 75° C. was continued until full consumption of the carboxylic acid by LCMS. The solution was then cooled to room temperature, diluted with EtOAc, and then sequentially washed with water and brine. Concentration in vacuo gave an oil that was used without further purification. This oil was directly dissolved in THF (16 mL) and treated with 1N HCl (4 mL). The solution was then warmed to 65° C. and stirred until the acetal deprotection was complete by LCMS (45 min). Upon completion, the solution was cooled to room temperature, diluted with EtOAc and sequentially washed with saturated NaHCO3, water, and brine. After drying over sodium sulfate, the material was concentrated and purified on silica gel (10-50% hex/EtOAc gradient) to give 4-hydroxy-3-methoxy-N-(4-(4-ethoxyphenyl)thiazol-2-yl)benzamide as a white solid (441 mg, 62% yield). 1H NMR (500 MHz, Chloroform-d) δ 7.76 (d, J=8.8 Hz, 2H), 7.57 (d, J=2.0 Hz, 1H), 7.45 (dd, J=8.3, 2.1 Hz, 1H), 7.04 (s, 1H), 7.01 (d, J=8.3 Hz, 1H), 6.95 (d, J=8.8 Hz, 2H), 3.99 (s, 3H), 3.85 (s, 3H).

A vial was charged with 4-hydroxy-3-methoxy-N-(4-(4-methoxyphenyl)thiazol-2-yl)benzamide (441 mg, 1.0 eq) and DMF (0.1 M). Potassium carbonate (343 mg, 2.0 eq) was added, followed by 2-chloro-1-morpholinoethan-1-one (163 µL, 1.0 eq). This solution was then warmed to 85° C. in a microwave reactor for 4 hours. The solution was partially concentrated and then partitioned between EtOAc and water. The aqueous layer was further extracted with EtOAc and the combined organic layers were dried over sodium sulfate. Purification on silica gel (10-100% hex/EtOAc gradient) gave 3-methoxy-N-(4-(4-methoxyphenyl)thiazol-2-yl)-4-(2-morpholino-2-xoethoxy)benzamide (398 mg, 66%) as a white solid. 1H NMR (500 MHz, methanol-d4) δ 7.87 (d, J=8.7 Hz, 2H), 7.69 (s, 1H), 7.69-7.62 (m, 1H), 7.26 (s, 1H), 7.08 (d, J=8.4 Hz, 1H), 6.96 (d, J=8.8 Hz, 2H), 4.94 (s, 2H), 3.97 (s, 3H), 3.83 (s, 3H), 3.69 (m, 4H), 3.61 (m, 4H). 13C NMR (125 MHz, methanol-d4) δ 166.10, 164.42, 159.76, 158.80, 151.04, 150.15, 149.73, 127.58, 127.38, 126.00, 120.52, 114.28, 112.98, 111.43, 106.61, 68.53, 67.02, 66.95, 56.21, 55.53, 46.18, 42.80.

Synthesis Route for SBI-993

The commercially available 4-((2-ethoxy-2-oxoethyl)amino)benzoic acid (1.21 g, 1.0 eq) was dissolved in acetonitrile (0.3 M) and treated with triethylamine (3.0 mL, 4.0 eq) and a 4-(4-methoxyphenyl)thiazol-2-amine hydrobromide (1.56 g, 1.0 eq). To this mixture was then added HATU (3.09 g, 1.5 eq). The resulting solution was warmed to 75° C. and stirred until the reaction was complete (~48 h). At this time the solution was cooled to room temperature and diluted with EtOAc. The solution was then sequentially washed with water (2×) and brine, dried over sodium sulfate, and then concentrated in vacuo. Purification on silica gel (hex/EtOAc gradient 10%-100%) gave an impure mixture which could be dissolved in DMF and precipitated by the addition of water. This solid was dissolved in THF (12 mL)

and water (4 mL) and treated with LiOH (308 mg, 4.0 eq). Saponification was completed within one hour of stirring at room temperature.

The solution was then diluted with EtOAc and washed with a 10% citric acid solution followed by brine. Drying on sodium sulfate and concentration gave a colored solid, which was then washed with a dichloromethane and methanol solution to give the intermediate carboxylic acid as an off-white solid (571 mg). This carboxylic acid (570 mg, 1.0 eq) was dissolved in DMF (0.25 M). Triethylamine (415 µL, 2.0 eq) and morpholine (518 µL, 4.0 eq) were then added. Lastly, HATU (680 mg, 1.2 eq) was added and the solution was stirred at room temperature for 2 h. Water was then slowly added to the reaction which then formed a precipitate. This precipitate was collected via filtration and washed with a mixture of THF and methanol to cleanly give N-(4-(4-methoxyphenyl)thiazol-2-yl)-4-((2-morpholino-2-oxoethyl)amino)benzamide (422 mg) as a white solid. 1H NMR (500 MHz, DMSO-d6) δ 12.22 (s, 1H), 7.95 (d, J=8.7 Hz, 2H), 7.88 (d, J=8.8 Hz, 2H), 7.44 (s, 1H), 7.01 (d, J=8.8 Hz, 2H), 6.76 (d, J=8.8 Hz, 2H), 6.48 (t, J=5.2 Hz, 1H), 4.05 (d, J=5.1 Hz, 2H), 3.80 (s, 3H), 3.61 (m, 4H), 3.56-3.47 (m, 4H).

Microarray Studies

Differentiated primary human myotubes were incubated with 10 µM SBI-477, 1 µM A922500 (DGAT inhibitor) or DMSO vehicle control for 24 hours. Total RNA was extracted using RNABee (Amsbio, Lake Forest, Calif.) and cleaned up using the RNeasy column (Qiagen, Valencia, Calif.) following manufacturer protocols. The Genomics core at Sanford Burnham Prebys-Lake Nona performed the hybridization to a GeneChip® Human gene 1.0 ST Array (Affymetrix, Santa Clara, Calif.). Two independent samples were analyzed for each group. Affymetrix experiment console version 1.1 was employed to normalize array data using the RMA approach. R package LIMMA (Linear Model for Microarray Data) was applied for differential gene expression analysis. The gene array data discussed in this publication have been deposited in NCBI's Gene Expression Omnibus and are accessible through GEO Series accession number GSE77212.

Lipidomics

Quantitative lipidomic analyses was performed on human skeletal myotubes exposed to bovine albumin serum (BSA) or 100 µM oleate in the presence of DMSO vehicle (white bars) or 10 µM SBI-477 (black bars) for 24 hours.

Primary human myotubes were treated with BSA or 100 µM oleate with 10 µM SBI-477 or a vehicle control for 24 hours. The cells were added to 3004, PBS in an Eppendorf tube and homogenized for 1 minute using a disposable soft tissue homogenizer. A 25 µL aliquot was used to determine the protein content (BCA protein assay kit, Thermo Scientific, Rockford, Ill.). The remaining homogenate was accurately transferred into a disposable glass culture test tube, and a mixture of lipid internal standards was added prior to lipid extraction for quantification of all reported lipid species. Lipid extraction was performed by using a modified Bligh and Dyer procedure as described previously (Wang and Han, 2014). Each lipid extract was resuspended into a volume of 500 µL of chloroform/methanol (1:1, v/v) per mg of protein and flushed with nitrogen, capped, and stored at −20° C. for lipid analysis. For ESI direct infusion analysis, lipid extract was further diluted to a final concentration of ~500 fmol/µL, and the mass spectrometric analysis was performed on a QqQ mass spectrometer (Thermo TSQ VANTAGE, San Jose, Calif.) equipped with an automated nanospray device (TriVersa NanoMate, Advion Bioscience Ltd., Ithaca, N.Y.).

Glycogen Synthesis Assay

Human skeletal myotubes were incubated with or without SBI-477 and then treated with or without insulin (100 nM) for 30 minutes. Glycogen synthesis rates were then measured as described (Halse, et al., *J Biol Chem.* 1999; 274 (2):776-780). Briefly, differentiated primary human skeletal myotubes were treated with SBI-477 as described in the glucose uptake assay. Following incubation with SBI-477, cells were serum starved in α-MEM for 1 hour. The medium was replaced with α-MEM supplemented with [14C]-D-glucose (1 µCi/mL) for three hours and then treated in the absence or presence of insulin (100 nM) for 30 minutes. After incubation, the cells were washed three times with ice-cold PBS and then lysed in 30% potassium hydroxide (KOH) containing 6 mg/mL glycogen. For glycogen precipitation, the samples were added to ice-cold 100% ethanol for 18 hours at 4° C. The samples were centrifuged at 8,500×g for 10 minutes at 4° C. and the supernatant was discarded. After one wash with 75% ethanol, the glycogen precipitate was dissolved in distilled water. [14C]-D-glucose incorporated to glycogen was counted by liquid scintillation analyzer (PerkinElmer) and normalized to total protein.

Glucose Tolerance Test and Insulin Signaling

Following a 5 hour fast, a blood sample was obtained from the tail tip for the measurement of baseline glucose using a hand-held glucometer (Accu-Chek Aviva Plus, Roche). A bolus of glucose (1 g/kg) was then administered via i.p. injection. Blood samples were obtained at 5, 15, 30, 60 and 90 minutes following the glucose bolus for measurement of blood glucose. For detection of insulin signaling, mice were fasted for 5 hours on the last day of the study. Gastrocnemius skeletal muscle and liver tissues were harvested 10 minutes after an acute insulin administration (1.5 U/kg, i.p.) and immediately snap frozen. The tissue samples were homogenized in RIPA buffer containing 1% NP-40, 5 mM Na4P2O7, 1 mM EDTA, 20 mM NaF, 2 mM Na3VO4, 1× Complete protease inhibitor (Roche) and 1 mM phenylmethylsulfonyl fluoride. Western blot analysis for levels of phospho-Akt (S473) and total Akt was then performed.

Myocyte Triglyceride Measurements

Human skeletal myotubes were differentiated for 8 days. On day 7, 100 µM of oleic acid complexed to fatty acid-free BSA was added to the cells with the indicated concentration of test compound for 24 hours. Following incubation with oleate and compound, cells were formaldehyde fixed and stained with AdipoRed™ (Lonza). Triglyceride accumulation was measured using signal intensity at excitation 540/emission 590 nm (Bio-Tek Instruments, Inc.). Dose response curves were generated in Prism 6 (GraphPad Software). EC50 values were calculated using non-linear regression analysis. For biochemical measurement of triglyceride, human skeletal myotubes were incubated with oleate-BSA and test compound as described above. After 24 hour incubation, cells were collected with a lysis buffer containing 0.1% IGEPAL CA-630 (Sigma-Aldrich) in PBS. The harvested cells were sonicated for 5 seconds and then centrifuged at 10,000×g for 10 minutes at 4° C. The supernatant was removed and stored on ice. TAG levels were quantified using Infinity™ Triglycerides Liquid Stable Reagent (Thermo Scientific), following the manufacturer's instructions for colorimetric assay.

Immunoblotting Analysis

Cells were lysed in the RIPA buffer containing 1% NP-40, 5 mM Na4P2O7, 1 mM EDTA, 20 mM NaF, 2 mM Na3VO4, 1× cOmplete™ protease inhibitor (Roche) and 1 mM phenylmethylsulfonyl fluoride. Whole cell lysates were subjected to SDS-PAGE and transferred to a nitrocellulose membrane. The blots were hybridized with specific antibodies and developed with enhanced chemiluminescence kit (Pierce). The following antibodies were used: phospho-Akt (Ser473), Akt, phospho-IRS-1 (Ser636/639), S6K, phospho-S6K (T389), AMPKα, phospho-AMPKα (T172), alpha-tubulin, and Lamin A/C (Cell Signaling Technology; catalog numbers 4058, 9272, 2388, 9202, 9234, 2532, 2531, 3873, and 2032 respectively); β-actin and IRS-1 (Y612) (Sigma-Aldrich; catalog numbers A5316 and I2658); IRS-1 and GAPDH (Santa Cruz Biotechnology; catalog numbers SC-560 and SC-25778); TXNIP (MBL; catalog number K0205-3); MondoA (Bethyl Laboratories; catalog number A303-195A). Protein quantification was performed using FluorChemQ (Alpha Innotech) and normalized to □-actin or total protein where indicated.

Cellular Glucose Uptake Assay

After differentiation, primary human skeletal myotubes were incubated with the indicated concentration of SBI-477 for 24 hours and then treated with insulin (100 nM) for 30 minutes. Cells were washed in phosphate-buffered saline (PBS) three times at room temperature and then incubated with Krebs-Ringer HEPES buffer (140 mM NaCl, 5 mM KCl, 1 mM CaCl2, 2.5 mM MgSO4, 2.5 mM, NaH2PO4, 20 mM HEPES and 0.1% bovine serum albumin) containing [3H]-2-deoxyglucose (1.0 μCi/mL) for 15 min. Glucose uptake was terminated by washing five times with ice-cold PBS. The cells were then solubilized with 0.5N sodium hydroxide (NaOH). The amount of [3H]-2-deoxyglucose taken up was measured by liquid scintillation analyzer (PerkinElmer) and normalized to total protein.

RNA Isolation and Quantitative RT-PCR

Total RNA was isolated using RNeasy Mini Kit (Qiagen) according to the manufacturer's instructions. cDNA was synthesized using the Affinity Script cDNA Synthesis Kit (Stratagene) with 0.5 μg of total RNA. PCR reactions were performed in triplicate The Sanford Burnham Prebys Medical Discovery Institute's Institutional Animal Care and Use Committee (IACUC) approved all animal studies. Roche LightCycler® 480 Instrument II) with specific primers for each gene. Primer sets are listed in Table 2.

TABLE 2

Primer sequences for qRT-PCR.

| Human | Gene Forward (5' to 3') | Reverse (5' to 3') |
| --- | --- | --- |
| ACACA (ACC1) | GTCAATCTTGAGGGCTAGGTCT (SEQ ID NO: 1) | CTGGTTCAGCTCCAGAGGTT (SEQ ID NO: 2) |
| ACACB (ACC2) | CAGGTGGGCCTATGAGATGT (SEQ ID NO: 3) | GGACGTAATGATCCGCCATCTT (SEQ ID NO: 4) |
| ARRDC4 | AGTTTCCTGCATGTTCATTCCT (SEQ ID NO: 5) | CCACAATTCGGGAACATGTATT (SEQ ID NO: 6) |
| DGAT1 | GTGGCTTCAGCAACTACCGT (SEQ ID NO: 7) | CAGGAACAGAGAAACCACCTG (SEQ ID NO: 8) |
| DGAT2 | GCTCTACTTCACTTGGCTGGT (SEQ ID NO: 9) | CAGCAGGTTGTGTGTCTTCAC (SEQ ID NO: 10) |
| ELOVL6 | GCAGTCAGTTTGTGACCAGG (SEQ ID NO: 11) | ATCAGCTTCTGCTTCCTCAGA (SEQ ID NO: 12) |
| FASN | GATGCCTCCTTCTTCGGAGT (SEQ ID NO: 13) | CCTCGGAGTGAATCTGGGTT (SEQ ID NO: 14) |
| GPAM (GPAT1) | TCAAGAGCGAGATGTGCATAAG (SEQ ID NO: 15) | CATCAGGGTTTAATTCAGCAG (SEQ ID NO: 16) |
| MLXIP (MondoA) | GCTCACCAAGCTCTTCGAGT (SEQ ID NO: 17) | GCCGGATCTTGTCTCTCCAC (SEQ ID NO: 18) |
| MLXIPL (ChREBP) | GTGTCTCCCAAGTGGAAGAATTT (SEQ ID NO: 19) | GCTCTTCCTCCGCTTCACAT (SEQ ID NO: 20) |
| SCD | CTTCTCTCACGTGGGTTGGC (SEQ ID NO: 21) | ATCAGCAAGCCAGGTTTGTAG (SEQ ID NO: 22) |
| TXNIP | AGTTTCCTGCATGTTCATTCCT (SEQ ID NO: 23) | CCACAATTCGGGAACATGTATT (SEQ ID NO: 24) |
| RPLP0 (36B4) | TCTACAACCCTGAAGTGCTTGAT (SEQ ID NO: 25) | ATAGAATGGGGTACTGATGCAA (SEQ ID NO: 26) |
| Mouse Gene | Forward (5' to 3') | Reverse (5' to 3') |
| Acaca (ACC1) | GGCCAGTGCTATGCTGAGAT (SEQ ID NO: 27) | ATCACACAGCCAGGGTCAAG (SEQ ID NO: 28) |
| Acacb (ACC2) | CGCTCACCAACAGTAAGGTGG (SEQ ID NO: 29) | GCTTGGCAGGGAGTTCCTC (SEQ ID NO: 30) |

TABLE 2-continued

Primer sequences for qRT-PCR.

| | | |
|---|---|---|
| Dgat1 | GTGCACAAGTGGTGCATCAG (SEQ ID NO: 31) | CAGTGGGATCTGAGCCATCA (SEQ ID NO: 32) |
| Dgat2 | GCATTTGACTGGAACACGCC (SEQ ID NO: 33) | CTGGTGGTCAGCAGGTTGTG (SEQ ID NO: 34) |
| Elovl6 | CGTAGCGACTCCGAAGATCA (SEQ ID NO: 35) | AGCGTACAGCGCAGAAAACA (SEQ ID NO: 36) |
| Fasn | CCAAGCAGGCACACACAATG (SEQ ID NO: 37) | GTTCGTTCCTCGGAGTGAGG (SEQ ID NO: 38) |
| Gpam (GPAT1) | ACAGTTGGCACAATAGACGTTT (SEQ ID NO: 39) | CTTCCATTTCAGTGTTGCAGA (SEQ ID NO: 40) |
| G6pc | GCTGGAGTCTTGTCAGGCAT (SEQ ID NO: 41) | GCCGCTCACACCATCTCTTA (SEQ ID NO: 42) |
| Pklr (LPK) | GCTAGGAGCACCAGCATCAT (SEQ ID NO: 70) | TGGGAGAAGTTGAGTCGTGC (SEQ ID NO: 43) |
| Mlx | CATGGACTCCCTCTTCCAGTC (SEQ ID NO: 44) | GATGAAGGACACCGATCACA (SEQ ID NO: 45) |
| Mlxip (MondoA) | TGCTACCTGCCACAGGAGTC (SEQ ID NO: 46) | GACTCAAACAGTGGCTTGATGA (SEQ ID NO: 47) |
| Mlxipl (ChREBP) | CAGCATCGATCCGACACTCA (SEQ ID NO: 48) | CGGATCTTGTCCCGGCATAG (SEQ ID NO: 49) |
| Pepck | AGTTCGTGGAAGGCAAT (SEQ ID NO: 50) | GTGAGAGCCAGCCAACA (SEQ ID NO: 51) |
| Scd1 | CCAAGCTGGAGTACGTCTGG (SEQ ID NO: 52) | CAGAGCGCTGGTCATGTAGT (SEQ ID NO: 53) |
| Txnip | GTCTCAGCAGTGCAAACAGACTT (SEQ ID NO: 54) | GCTCGAAGCCGAACTTGTACTC (SEQ ID NO: 55) |
| Rplp0 (36B4) | TGGAAGTCCAACTACTTCCTCAA (SEQ ID NO: 56) | ATCTGCTGCATCTGCTTGGAG (SEQ ID NO: 57) |

The expression of Rplp0 (36B4) was used to normalize all gene expression data.

Transient Transfection and Luciferase Reporter Assay

Transient transfections were performed using Attractene (Qiagen) according to the manufacturer's protocols. A full length (1.5 kb) and two serial deletion (1.0 kb and 0.5 kb) reporters of the human TXNIP promoter were generously provided by Dr. Fumihiko Urano (Washington University School of Medicine). Mutation of the carbohydrate-responsive elements (ChoREs) of the reporters was generated by QuikChange II Site-Directed Mutagenesis kit (Agilent). H9c2 myoblast cells (ATCC) were cotransfected with 700 ng of the reporter and 25 ng of CMV promoter driven Renilla luciferase as a control for transfection efficiency. Eighteen hours after transfection, the cells were cultured in DMEM supplemented with 1% fetal bovine serum to induce differentiation for 4 days. SBI-477 was added during the last 24 hours at the indicated concentration. After compound incubation, luciferase activity was measured using the Dual-Glo luciferase assay system (Promega) according to the manufacturer's protocols.

Chromatin IP (ChIP) Assay

ChIP assays were performed as previously described (Gan, et al., Genes Dev., 2011, 25(24):2619-2630). Briefly, differentiated human skeletal myotubes were cross-linked with 1% formaldehyde for 10 minutes at room temperature, and glycine was added to stop the cross-linking reaction. Cells were harvested and lysed. For chromatin fragmentation, sonication was performed using a Bioruptor (Diagenode). Proteins were immunoprecipitated by using anti-MondoA (Bethyl Laboratories; catalog number A303-195A) or IgG control (Sigma; catalog number 15006) overnight at 4° C. DNA fragments were purified using a QIAquick PCR purification kit (Qiagen) and quantified by a LightCycler® 480 Instrument II (Roche) with the specific primers listed in Table 1.

TABLE 1

Primer sequences for ChIP-qRT-PCR.

| Human promoter | Forward (5' to 3') | Reverse (5' to 3') |
|---|---|---|
| TXNIP ChoRE | CCGGGCAGCCAATGGGAG (SEQ ID NO: 58) | GCAGGAGGCGGAAACGTCTC (SEQ ID NO: 59) |
| ARRDC4 ChoRE | CGGAGATAACCCTGTTCCGC (SEQ ID NO: 60) | CAGGCCGTTTACTGGCTGA (SEQ ID NO: 61) |
| Impa2 MEF2 | CTATCGGATGGTCAGCTTCAA (SEQ ID NO: 62) | GCACTGGCTTCTCATGTTTATC (SEQ ID NO: 63) |
| Mouse promoter | Forward (5' to 3') | Reverse (5' to 3') |
| Txnip ChoRE | GCCTGGTAAACAAGGGCCAA (SEQ ID NO: 64) | GCTGCCGGAAACGGCTTATA (SEQ ID NO: 65) |
| Pklr ChoRE | GATCCAGGCTCTGCAGACAG (SEQ ID NO: 66) | CAGCTAGCATCTCTCTTGCCA (SEQ ID NO: 67) |
| Myh7 Intron 26 | TGCATACAGACTTGGTGAATAG (SEQ ID NO: 68) | GAACAGTGTGAAGACTCCTATG (SEQ ID NO: 69) |

In Vivo Studies

All animal studies were performed in accordance with the National Institute of Health guidelines for humane treatment of animals and approved by the IACUC of the Sanford Burnham Prebys Medical Discovery Institute at Lake Nona. Six week old male C57BL/6J mice were obtained from Jackson Laboratory (stock number 000664) and acclimated for 1 week prior to study. Mice were maintained on standard chow or a 60% high fat diet (Research Diets, USA) for 8 weeks. SBI-993 was dissolved in a vehicle containing 2% DMSO, 2% Tween-80, and 96% water (pH9.0). Seven weeks after HFD feeding, mice were subcutaneously injected with SBI-993 (50 mg/kg mouse body weight) once daily for 7 days. Each group contains 6-10 mice and three independent experiments were conducted.

Statistics

Student's t-test, Mann Whitney test, one-way ANOVA with Bonferroni post hoc test, or two-way ANOVA with Tukey post hoc test was performed to determine statistical significance as indicated. Non-linear regression analysis was used to calculate EC50 values of SBI-477 and SBI-993 in the triglyceride accumulation assay in human skeletal myotubes (GraphPad Prism 6).

Results

Figure 1B:
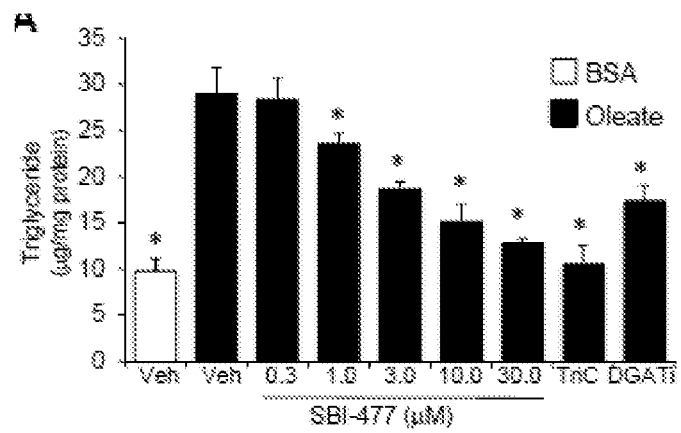
Figure 1C:
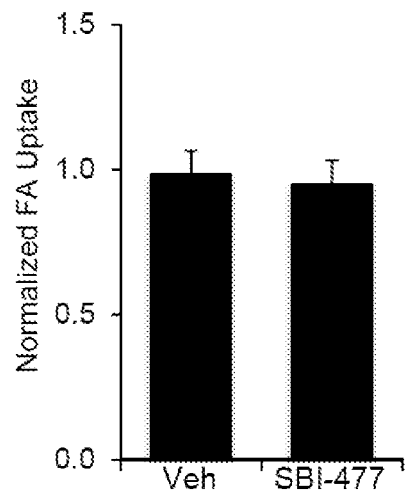
Figure 1D:
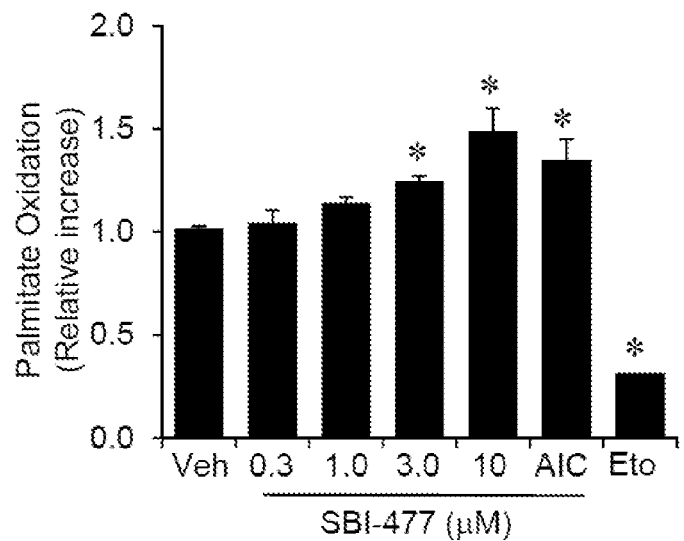
FIGS. 1D-1F show the effect of SBI-477 on FAO rates in human skeletal myotubes.
Figure 1E:
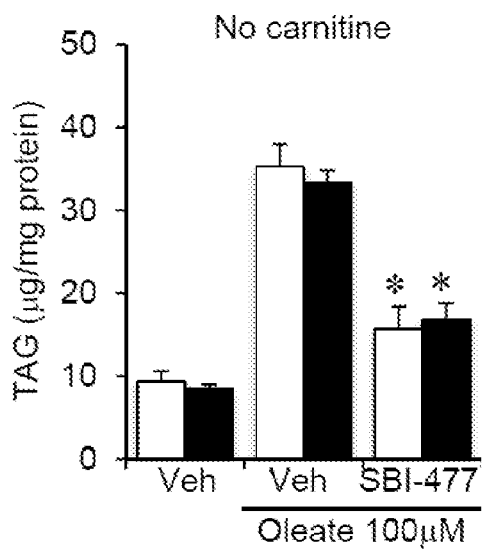
Figure 1F:
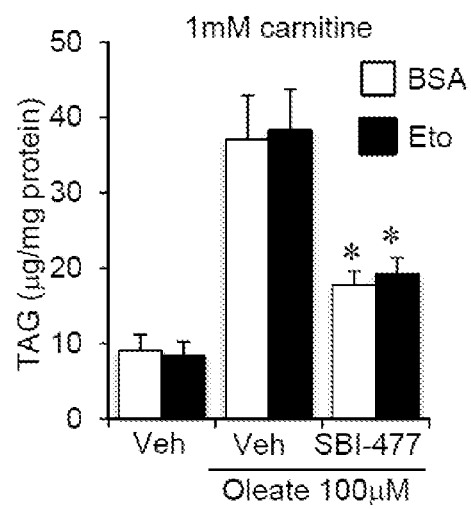

Identification of a Small Molecule Inhibitor of Myocyte Neutral Lipid Accumulation Hits from a cell-based high-throughput screen performed on murine AML12 hepatocytes to identify molecular probes that decrease triacylglyceride (TAG) accumulation resultant from oleate loading were examined for chemical tractability and activity in human skeletal myocytes. One particular compound, an N-(thiazol-2-yl)-benzamide termed SBI-477, showed potent inhibition of TAG accumulation in rat H9c2 myocytes (EC50≈100 nM, data not shown) and human skeletal myotubes (EC50≈1 µM; FIGS. 1A and 1B, data not). Inhibition of TAG accumulation by SBI-477 was not due to blocking cellular fatty acid uptake or increasing intracellular lipolysis rates (FIG. 1C and data not shown). In addition, SBI-477 had no effect on the gene expression of the fatty acid transporter, CD36 (data not shown). Increased oxidation of fatty acids could also account for the TAG-lowering actions of SBI-477. Indeed, FAO rates were increased by SBI-477 in a dose-dependent manner concordant with inhibition of increased triglyceride storage (FIG. 1D). Acylcarnitine species indicative of mitochondrial fatty acid oxidation (FAO) intermediates were also increased following exposure to SBI-477 in human myotubes consistent with increased mitochondrial FAO rates (FIG. 1E). However, inhibition of FAO did not prevent the actions of SBI-477 on TAG levels, even in the presence of carnitine, suggesting that this effect is likely downstream of the primary site of TAG-lowering action (FIGS. 1E and 1F).

Figure 2A:
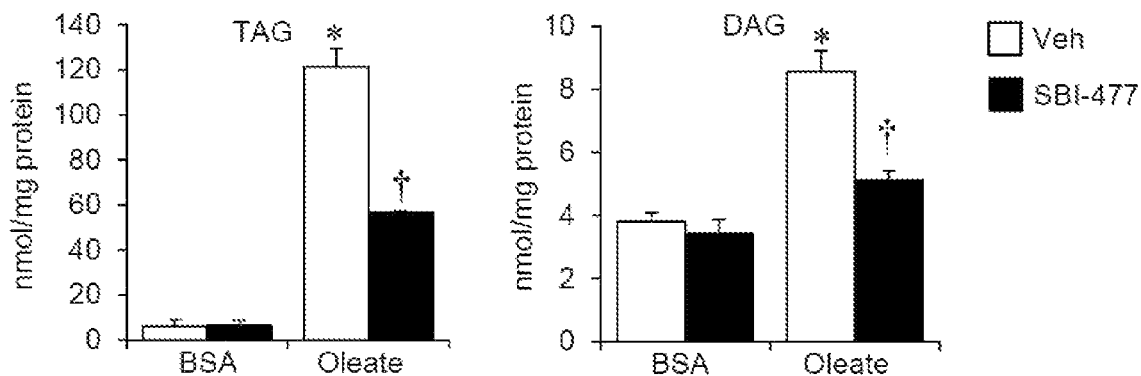
FIGS. 2A and 2B show SBI-477 inhibition of expansion of cellular DAG and TAG pools in oleate-loaded myocytes. The results of quantitative lipidomic analyses performed on human skeletal myotubes exposed to bovine albumin serum (BSA) or 100 oleate in the presence of DMSO vehicle (white bars) or 10 µM SBI-477 (black bars) for 24 hours.
Figure 2B:
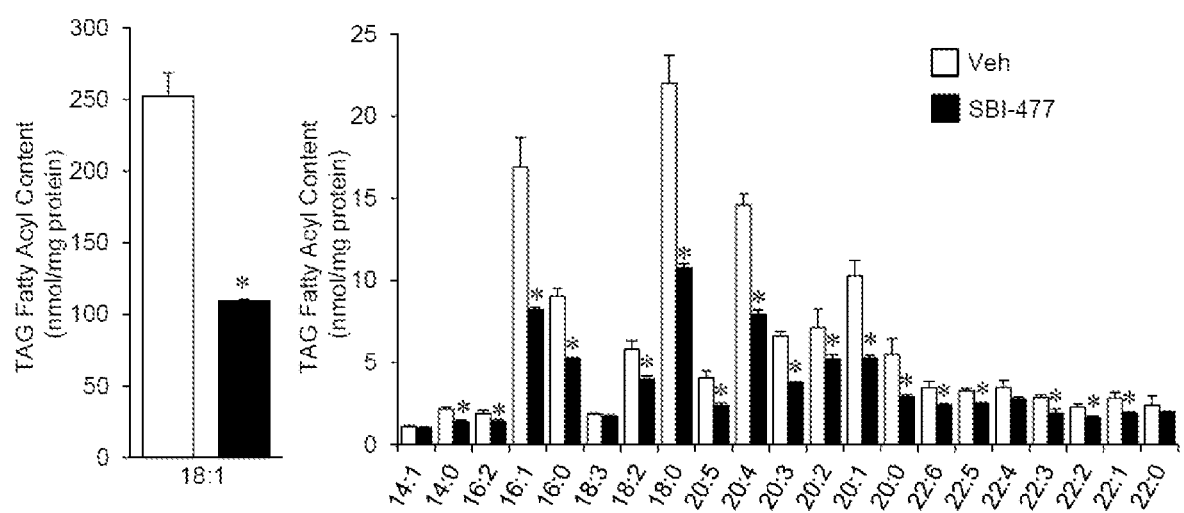

To assess the effects of SBI-477 on triglyceride synthesis and remodeling, quantitative lipidomic analyses were conducted on extracts of oleate-loaded human skeletal myotubes following a 24 hour exposure to SBI-477, compared to vehicle. The effects of SBI-477 were broad, reducing all TAG species measured, with greatest effects on TAG species with acyl chain lengths from 16-20. 18:1 species were markedly reduced by SBI-477, consistent with oleate loading (FIGS. 2A and 2B). Levels of TAG and DAG species were also reduced following exposure to the compound (FIG. 2A). The levels of specific lipid species implicated in insulin resistance or cellular lipotoxicity were also examined. Levels of ceramide and total sphingomyelin were not significantly altered with SBI-477 treatment in oleate-loaded myotubes. However, a significant reduction in a subset of sphingomyelin species including those containing a 16:0 acyl chain was observed with SBI-477 treatment. Interestingly, however, these changes were not observed in non-oleate loaded myotubes. These results indicate that SBI-477 inhibits incorporation of all fatty acids, including those of exogenous origin, into the neutral lipid TAG pool.

Intracellular TAG can be formed through reacylation of DAG species generated from several pathways including a de novo glycerolphosphate biosynthetic pathway that involves dephosphorylation of phosphatidic acid (DAGPA), reacylation of monoacylglycerol (DAGMAG), and to a lesser extent, hydrolysis of phosphatidyl inositol (DAGPI). To explore the effects of SBI-477 on specific TAG biosynthesis pathways, a bioinformatics lipidomics modeling approach was used as previously described (Han, et al., *Lipid Res.* 2013; 54(4):1023-1032). This approach uses the individual TAG ion profile, as determined by mass spectrometry, to predict the relative contribution of each pathway to the overall cellular TAG pool. Experiments were conducted in skeletal myocytes in the absence and presence of oleate loading. In the absence of exogenous oleic acid, SBI-477 markedly reduced contribution by the de novo glycerolphosphate biosynthetic pathway (K1) resulting in shift (10-fold increase) to the monoacylglycerol reacylation pathway (K2) (Table 3).

TABLE 3

Triglyceride remodeling induced by SBI-477

| Pathway | BAS/ Vehicle | BSA/ SBI-477 | Oleate/ Vehicle | Oleate/ SBI-477 |
|---------|--------------|--------------|-----------------|-----------------|
| K1 | 0.96 ± 0.03 | 0.50 ± 0.08* | 0.25 ± 0.02 | 0.36 ± 0.03* |
| K2 | 0.04 ± 0.03 | 0.44 ± 0.10* | 0.75 ± 0.02 | 0.63 ± 0.03* |
| K3 | 0.00 | 0.05 ± 0.03 | 0.00 | 0.01 ± 0.02 |

In contrast, incubation with SBI-477 resulted in a modest decrease in K2 with a shift to K1 in the oleate-loaded condition. These results, together with the lipidomic profiling data, indicate that SBI-477 inhibits several cellular TAG synthesis pathways and that the mechanism for inhibition of TAG biosynthesis by SBI-477 is distinct depending on whether the source of fatty acid is exogenous or synthesized de novo. Notably, it was not found that SBI-477 directly inhibits the activity of SCD-1, DGAT1/2 or MGAT1/2/3 (data not shown) which led to the discovery of a novel inhibitory mechanism.

Stimulation of Muscle Glucose Uptake and Insulin Signaling by SBI-477

Figure 3A:
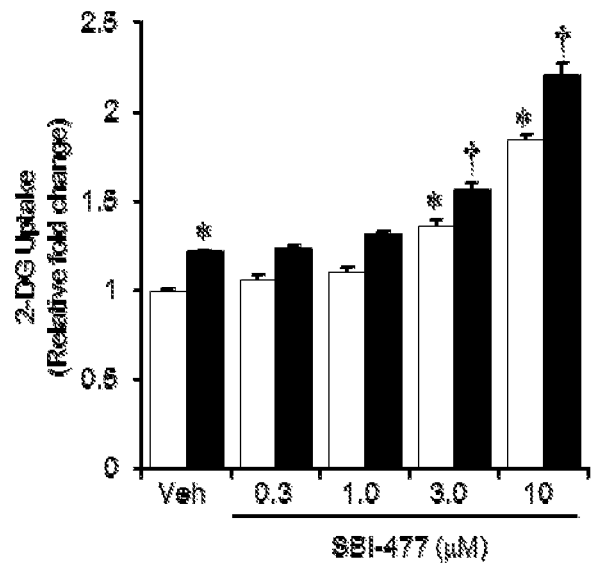
FIGS. 3A, B, C, E and F show SBI-477 stimulation of glucose uptake and activates insulin signaling in the absence of insulin. Human skeletal myotubes were incubated with SBI-477 at the indicated concentration for 24 hours and then treated with or without insulin (100 nM) for 30 minutes. Glucose ([3H]-2-deoxyglucose, 2-DG) uptake (FIG. 3A) and glycogen synthesis rates (FIGS. 3B and 3C) were measured (n=5) as described in Methods. *$p<0.05$ vs. Vehicle, no insulin, †$p<0.05$ vs. Vehicle/insulin by two-way ANOVA with Tukey's post hoc test.

Subsequent studies sought to determine whether the IMCL-lowering effects of the molecular probe, SBI-477, was linked to changes in myocyte glucose uptake. SBI-477 increased both basal and insulin stimulated glucose uptake in human skeletal myotubes (approximately 84% at 10 μM SBI-477; FIG. 3A). Several compounds identified as hits from the AML12 hepatocyte high throughput screen (HTS) were tested for their ability to increase glycogen synthesis in H9c2 myotubes. Glycogen synthesis was used as a surrogate readout for glucose uptake in these cells. As shown, only SBI-477 (MLS-0227479) increased insulin-stimulated glycogen synthesis as compared to vehicle. Several examples of hits from the AML12 hepatocyte HTS were tested for their ability to increase glycogen synthesis in H9c2 myotubes. The tested compounds were:

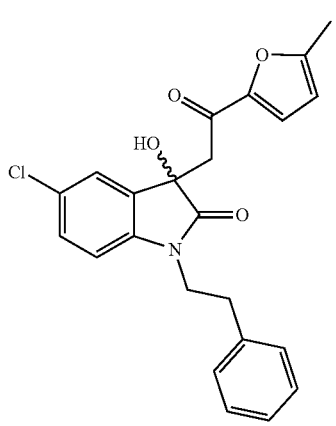

MLS-0435812

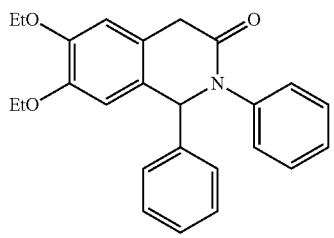

MLS-0219458

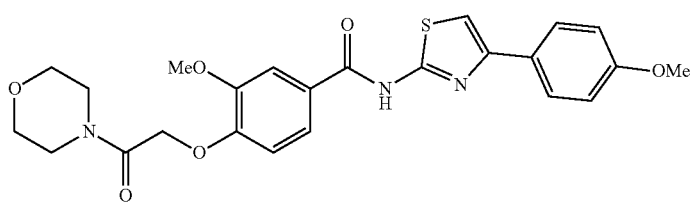

MLS-0227479

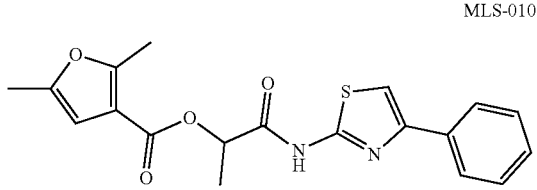

MLS-0108647

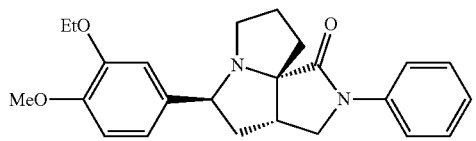

MLS-0288160

-continued

MLS-0377328

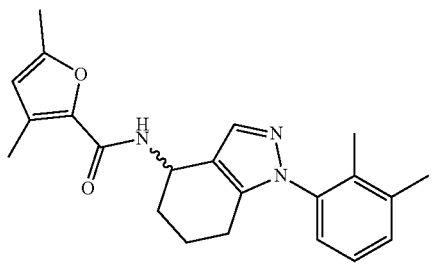

MLS-0348610

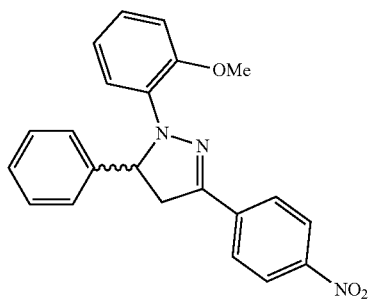

MLS-0270695

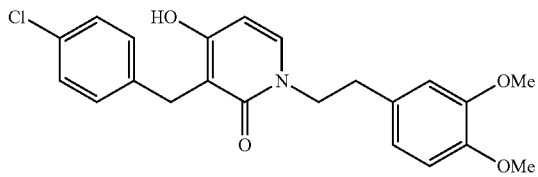

MLS-0054531

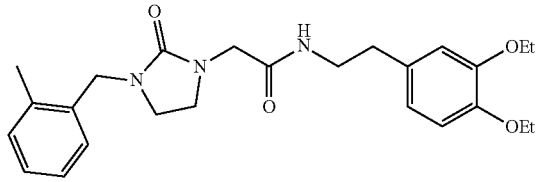

MLS-0390149

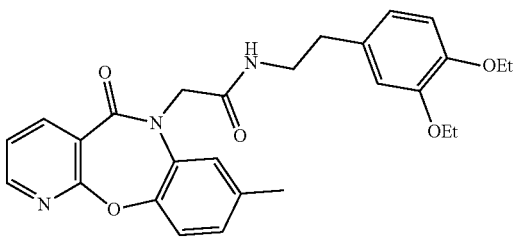

MLS-0270695

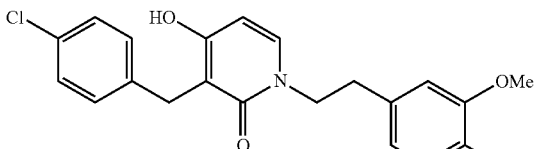

MLS-0389060

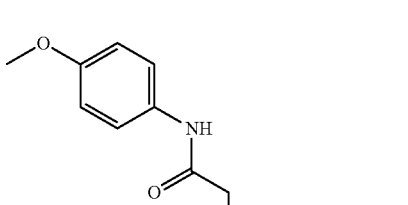

MLS-0389124

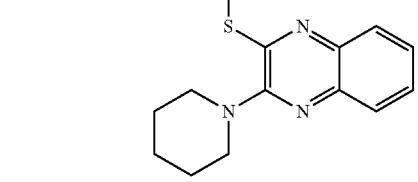

Figure 3B:
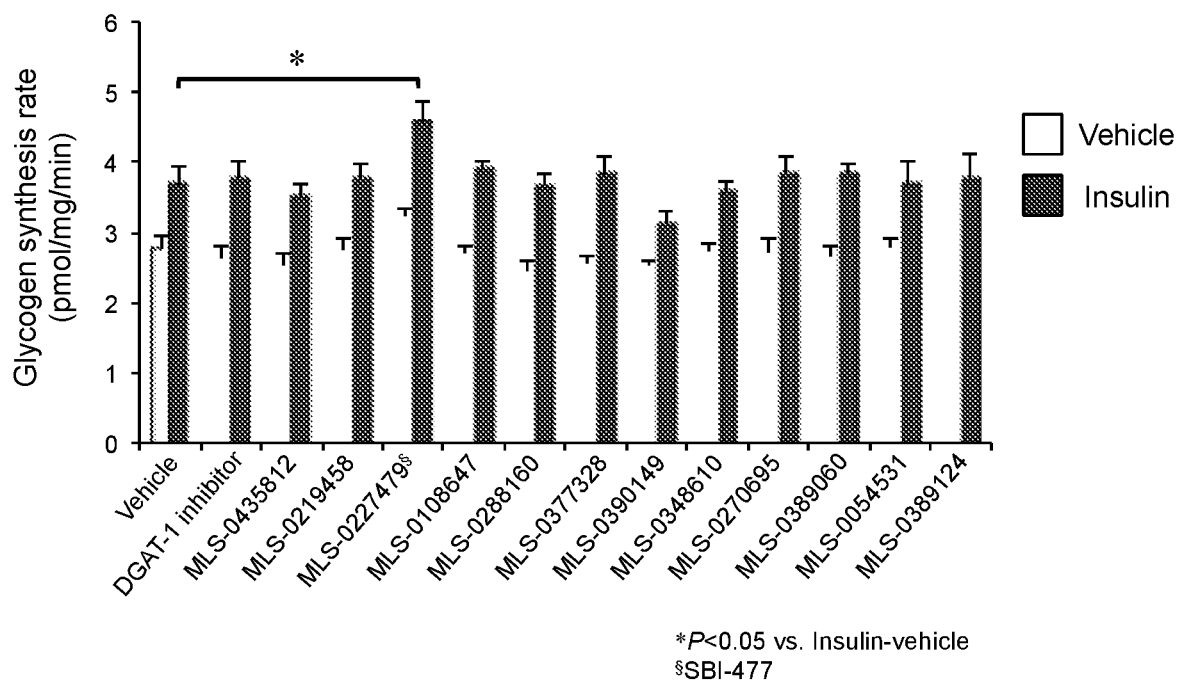
(FIG. 3E) Western blot analysis of human myotubes treated with SBI-477 for 24 hours was performed to determine the effect on steps of the insulin signaling pathway using specific Akt and IRS-1 phosphorylation sites as endpoints. Insulin treatment (100 nM) for 30 minutes was used as positive control.
(FIG. 3F) Quantitation of the western blot data in (FIG. 3D) is shown (n=5). *$p<0.05$ or **$p<0.01$ vs. Vehicle by one-way ANOVA with Bonferroni post hoc test. The data represent mean±SD.
FIGS. 3D and G show SBI-477-mediated increase in glucose uptake in oleate-loaded skeletal myotubes (FIG. 3D) SBI-477 increases glucose uptake in oleate-loaded human skeletal myotubes. Basal and insulin-stimulated [3H]2-DG uptake was measured in human skeletal myotubes following treatment with SBI-477 for 24 hours in the presence of 100 µM oleate or BSA as a control. *$p<0.05$ vs. vehicle, †$p<0.05$ vs. vehicle/insulin by one-way ANOVA with Bonferroni post hoc test.
FIG. 3G—Western blot analysis (left) of human myotubes treated with SBI-477 for 24 hours was performed to determine activation of S6K and AMPK using the indicated phospho-specific antibodies. Insulin treatment (100 nM) for 30 minutes was used as positive control. Quantitation (right) of the Western blot data is shown (n=4-5). *$p<0.05$ vs. Vehicle by one-way ANOVA with Bonferroni post hoc test. The data represent mean±SD.
Figure 3C:
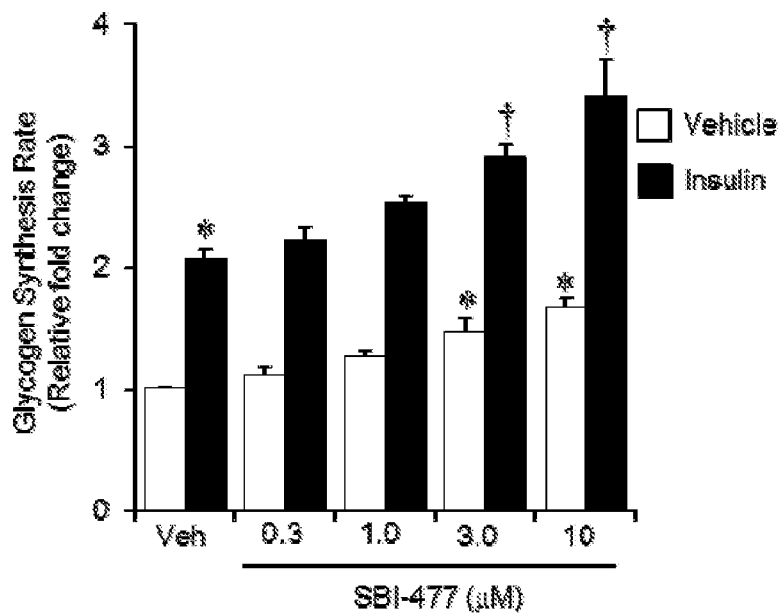
Figure 3D:
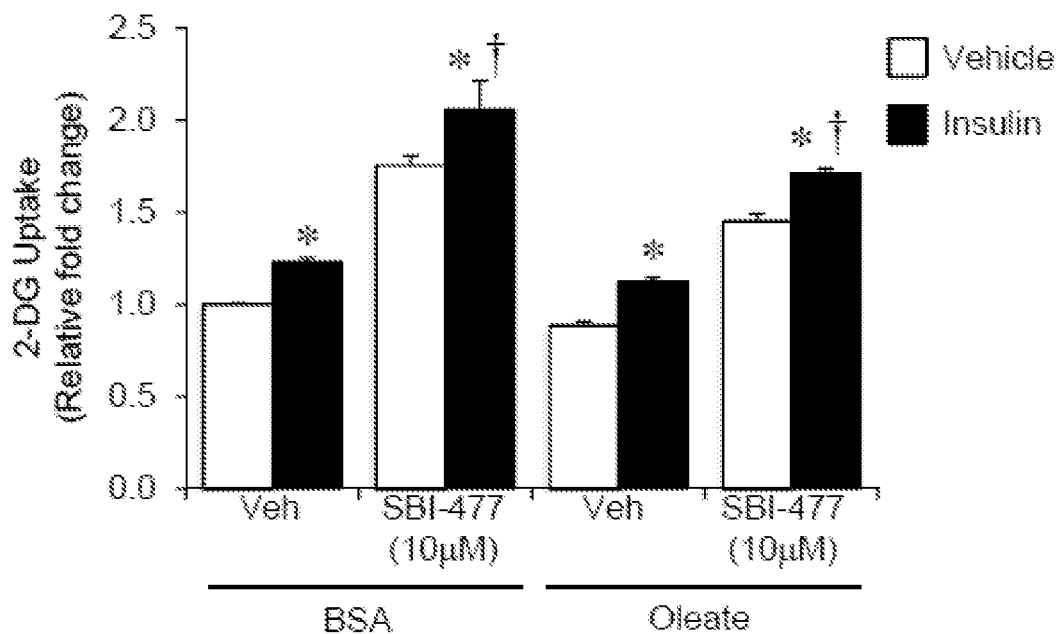
Figure 3E:
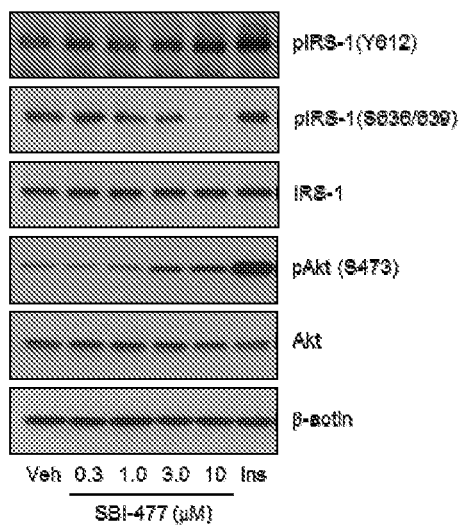
Figure 3F:
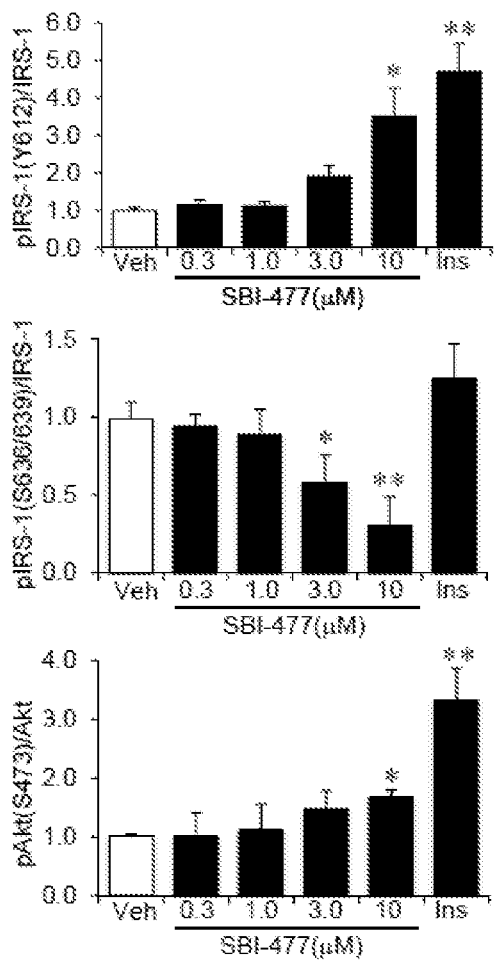

As shown in FIG. 3B, only SBI-477 (MLS-0227479) increased insulin-stimulated glycogen synthesis as compared to vehicle. Glycogen synthesis rates were enhanced by SBI-477 treatment in a dose dependent manner (FIG. 3C). The effects on glucose uptake were independent of, but additive with, that of insulin. Similar effects on glucose uptake were observed in oleate-loaded myotubes (FIG. 3D). Interestingly, SBI-477 activated insulin signaling in the absence of insulin. Specifically, tyrosine phosphorylation of the insulin receptor substrate 1 (IRS-1) was increased by SBI-477 (FIGS. 3E and 3F). Conversely, IRS-1 phosphorylation at serine sites 636/639, which has been shown to confer inhibition of insulin signaling (Bouzakri, et al., Diabetes. 2003; 52(6):1319-1325), was decreased by exposure to SBI-477. Phosphorylation of the downstream effector kinase, Akt, was also increased by SBI-477. The effects on insulin signaling triggered by SBI-477 were observed after 24 hours of compound exposure but not with acute treatment (data not shown). These results indicate that SBI-477 stimulates glucose uptake by activating insulin signaling through a mechanism that does not require insulin engaged to its receptor.

Figure 3G:
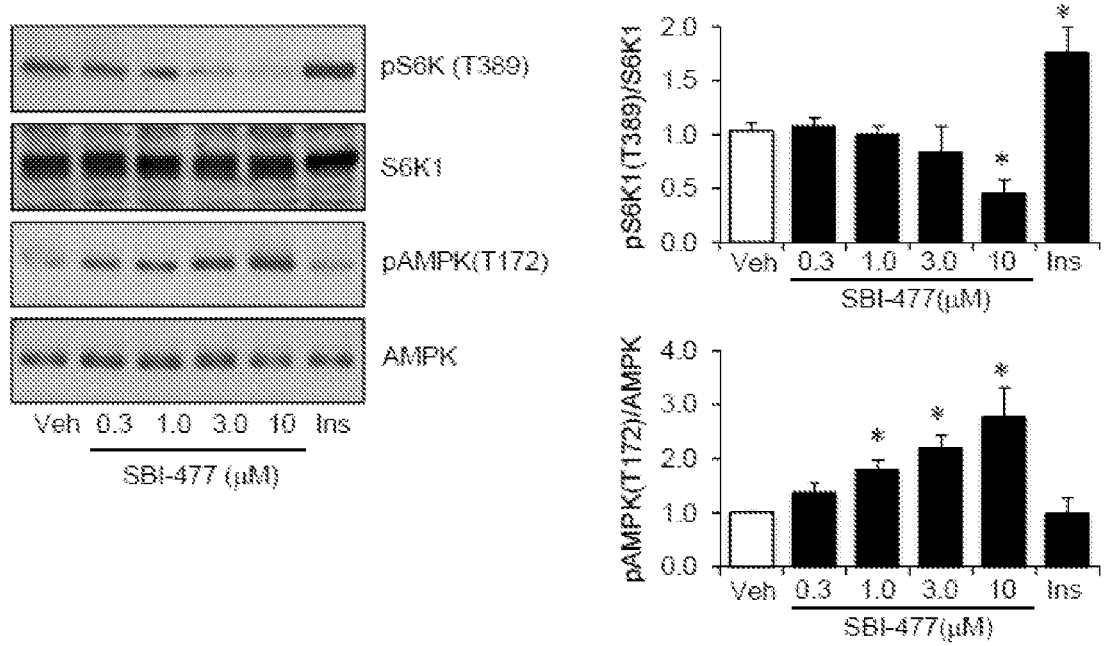

Signaling events downstream of insulin signaling were also assessed. Surprisingly, levels of pS6K (T389), a target of insulin—mTORC1 signaling, were reduced by SBI-477 treatment (FIG. 3G). Accordingly, other signaling pathways upstream of mTORC1 were examined. Notably, SBI-477 treatment resulted in activation of AMPK, an inhibitor of mTOR signaling, consistent with the observed inhibitory phosphorylation of S6K (FIG. 3G). It is possible, therefore, that activation of AMPK inhibits mTORC1 activity, despite activation of insulin signaling, in the context of SBI-477 exposure.

Figure 4A:
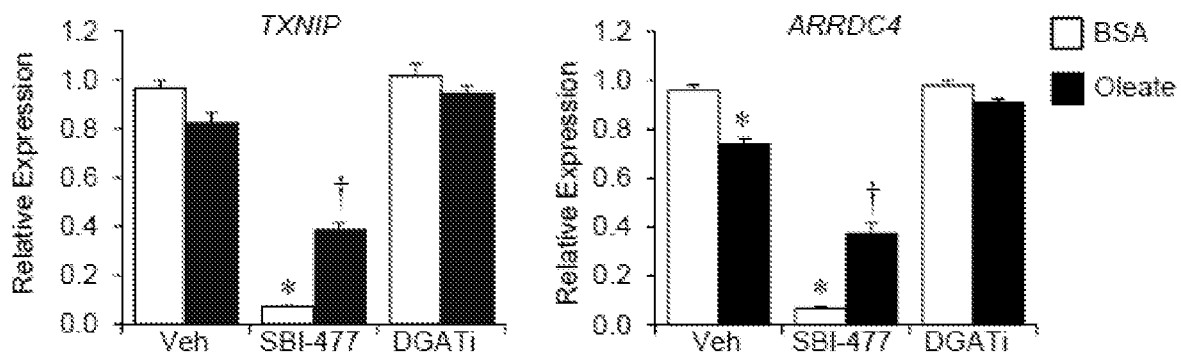
FIGS. 4A-C show downregulation of TXNIP and ARRDC4 expression by SBI-477.
Figure 4B:
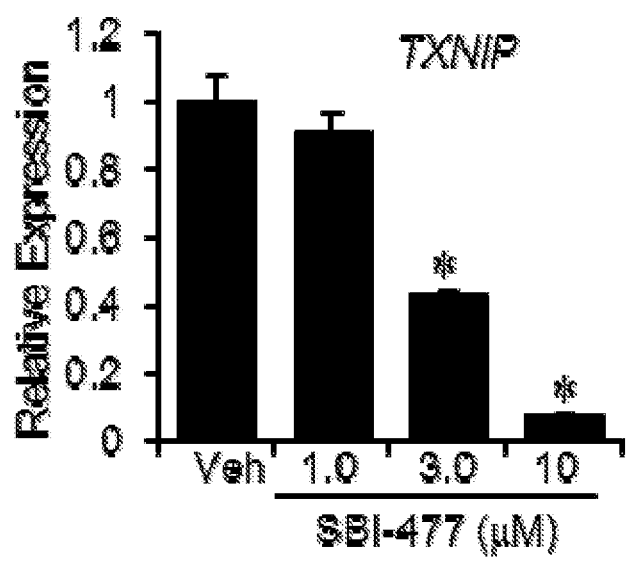
Figure 4C:
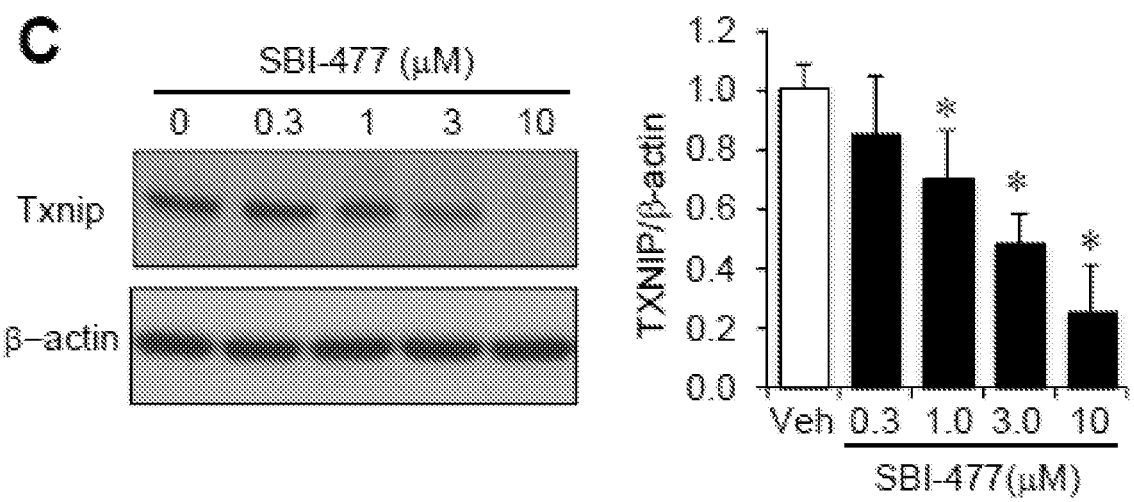

SBI-477 Reduces Expression of TXNIP and ARRDC4, Negative Regulators of Insulin Signaling, Via Deactivation of the Transcription Factor MondoA To gain further insight into the downstream actions of SBI-477, transcriptional profiling were conducted in primary human skeletal myotubes. Heat map visualization of differentially expressed transcripts revealed that 24 hour exposure to SBI-477 prevented many of the transcriptomic changes resultant from oleate loading, and regulated a distinct subset of transcripts compared with that of a DGAT1 inhibitor (data not shown). Examination of the highly regulated transcripts regulated by SBI-477, but not the DGAT inhibitor, identified thioredoxin interacting protein (TXNIP) and arrestin-domain containing 4 (ARRDC4) as markedly downregulated. TXNIP and ARRDC4 have been shown to function as potent negative regulators of glucose uptake and insulin signaling (Parikh, et al. *PLoS Med* 2007; 4(5):e158; Yoshihara, et al. *Nat Commun.* 2010; 1:127). SBI-477 conferred robust, dose-dependent downregulation of TXNIP and ARRDC4 expression in human myotubes, an effect that was also observed under oleate-loaded conditions, albeit to a lesser extent (FIGS. 4A-4B). TXNIP protein levels were also reduced by SBI-477 in dose-dependent manner (FIG. 4C).

Figure 5A:
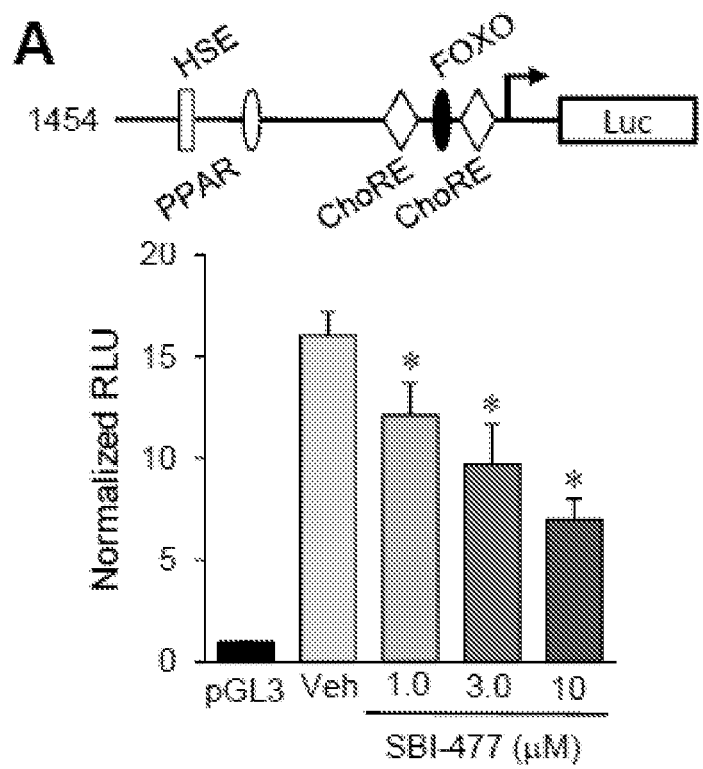
FIGS. 5A-5D show SBI-477 inhibition of MondoA-mediated activation of the TXNIP gene promoter via effects on nuclear localization.
Figure 5B:
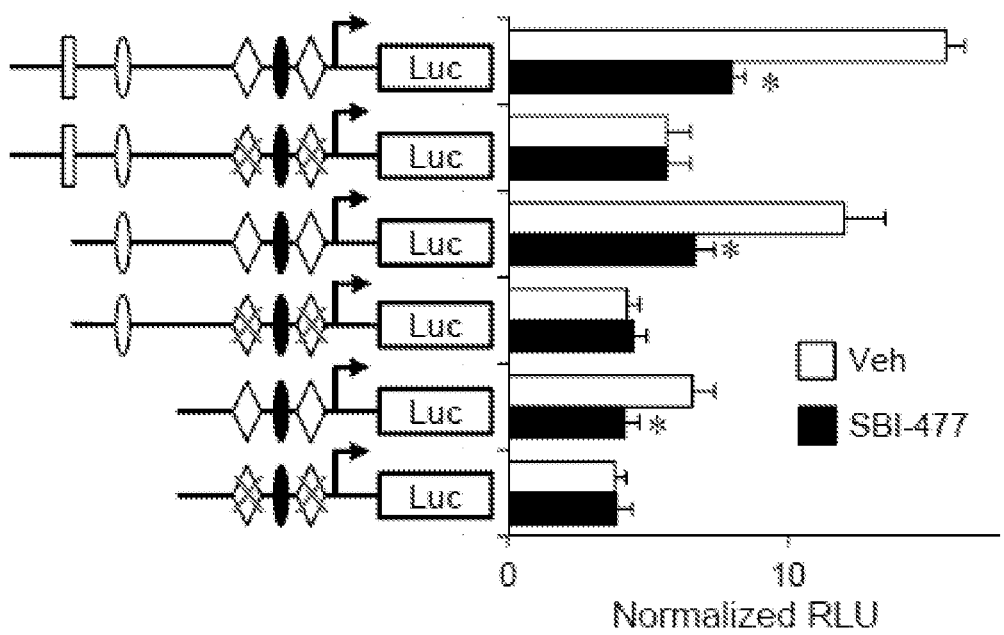

Given the marked down regulation of TXNIP and ARRDC4 transcript levels by SBI-477, effects at the transcriptional level were explored next. For these studies, a reporter construct containing approximately 1.5 kb of the human TXNIP promoter was transfected into H9c2 myocytes (Oslowski, et al., *Cell Metab.* 2012; 16(2):265-273). SBI-477 decreased promoter activity in a dose dependent manner (FIG. 5A). Regulation of TXNIP expression is known to be regulated, at least in part, by two carbohydrate response elements (ChoRE) within its promoter region (Cha-Molstad, et al., *J Biol Chem.* 2009; 284(25):16898-16905). Mutational analysis confirmed that the SBI-477-mediated inhibition of TXNIP promoter is dependent upon an intact ChoRE (FIG. 5B).

Figure 5C:
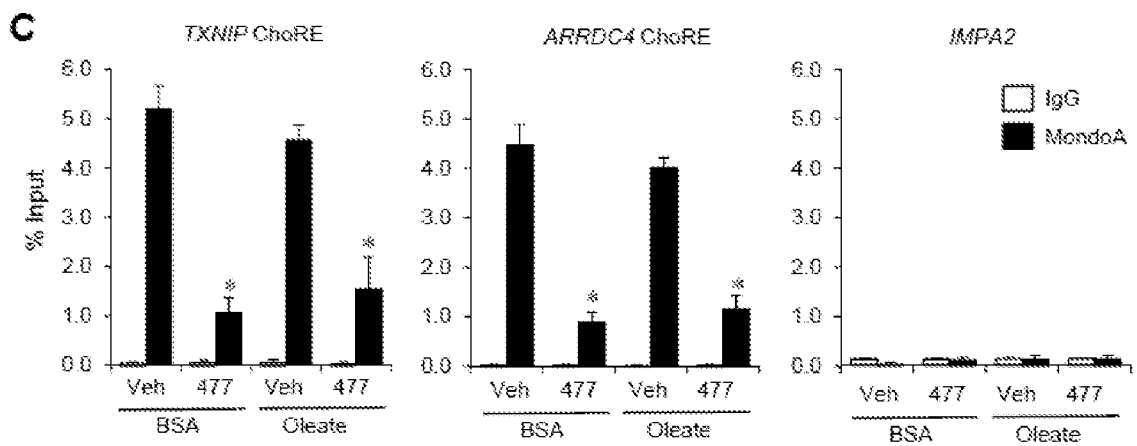

ChoREs were originally characterized as bound by heterodimers comprised of the Carbohydrate Responsive Element-Binding Protein (ChREBP; MondoB) and Max-like protein X (MLX) transcription factors. A highly related protein, MondoA is muscle-enriched and has been shown to bind to similar consensus sites (Billin, et al. *Mol Cell Biol.* 2000; 20(23):8845-8854). There studies confirmed that human myotubes in culture predominantly express MondoA compared to ChREBP (MondoB) using immunoblotting (data not shown). Both ChREBP and MondoA have been shown to regulate TXNIP and ARRDC4 expression (Cha-Molstad, et al., *J Biol Chem.* 2009; 284(25):16898-16905; Stoltzman, et al., *Proc Natl Acad Sci USA.* 2008; 105(19):6912-6917). Therefore, additional studies sought to determine if SBI-477 affected occupation of the ChoREs located in the TXNIP and ARRDC4 promoter regions. Chromatin immunoprecipitation (ChIP) studies confirmed occupation of MondoA on ChoREs located within both the TXNIP and ARRDC4 promoter regions but not on a control Mef2 binding site in the IMPA2 gene promoter in human skeletal myotubes (FIG. 5C). The occupation by MondoA was inhibited by SBI-477 (FIG. 5C). Thus, SBI-477 reduces the binding of MondoA to the TXNIP and ARRDC4 promoter regions.

Figure 5D:
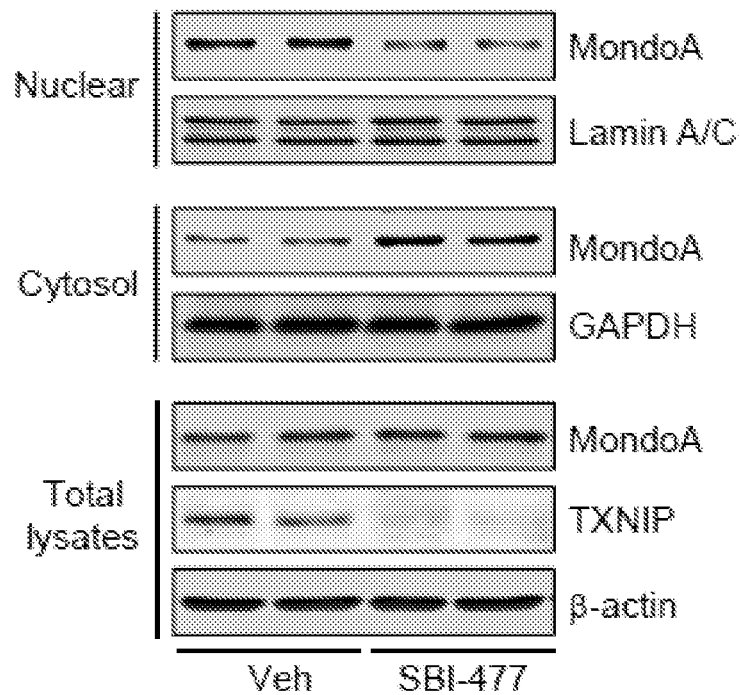

The activity of ChREBP and MondoA is governed, in part, by nuclear-cytoplasmic shuttling mechanisms that are incompletely understood but likely involve glucose metabolites and phosphorylation (Stoltzman, et al., *Proc Natl Acad Sci USA.* 2008; 105(19):6912-6917; Filhoulaud, et al., *Trends Endocrinol Metab.* 2013; 24(5):257-268). Accordingly, the effect of SBI-477 on intracellular localization of MondoA was assessed. Immunolocalization studies confirmed that treatment with SBI-477 resulted in near complete nuclear exclusion of MondoA in human skeletal myoblasts (data not shown). The results of immunoblotting studies conducted with fractionated cellular extracts further supported this conclusion (FIG. 5D). Taken together, these results demonstrate that downregulation of TXNIP and ARRDC4 expression downstream of SBI-477 involves deactivation of MondoA via effects on nuclear localization.

Figure 6A:
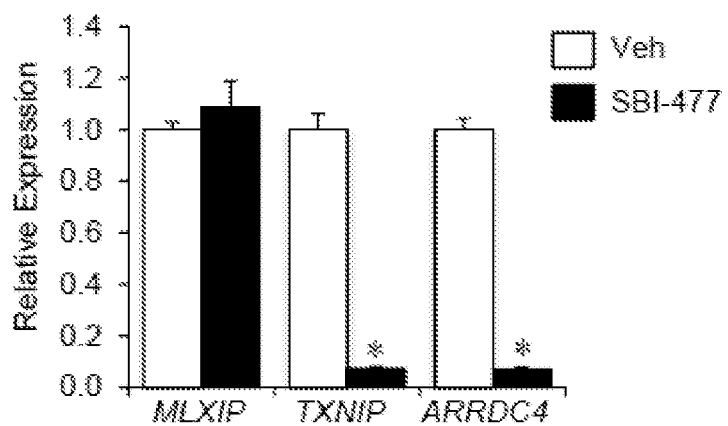
FIGS. 6A to 6F show that MondoA depletion mimics action of SBI-477 in human skeletal myotubes. TXNIP and ARRDC4 gene expression was measured following treatment with 10 mM SBI-477 (FIG. 6A) or siRNA-mediated MondoA (MLXIP) KD (FIG. 6B) (n=4). *p<0.05 vs. Vehicle or non-targeting siRNA control (siCon).
Figure 6B:
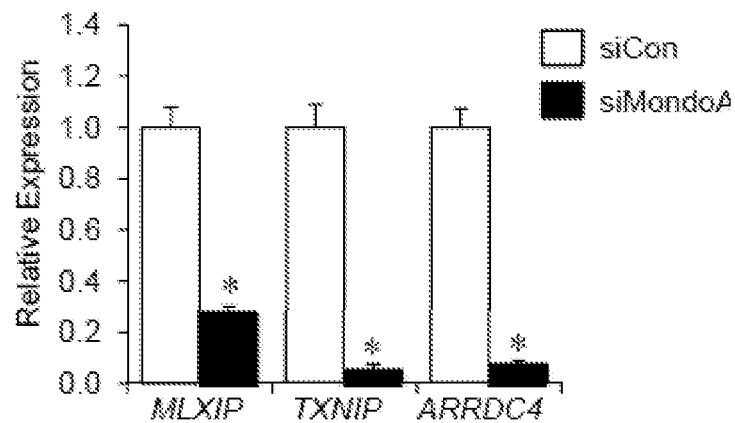
Figure 6C:
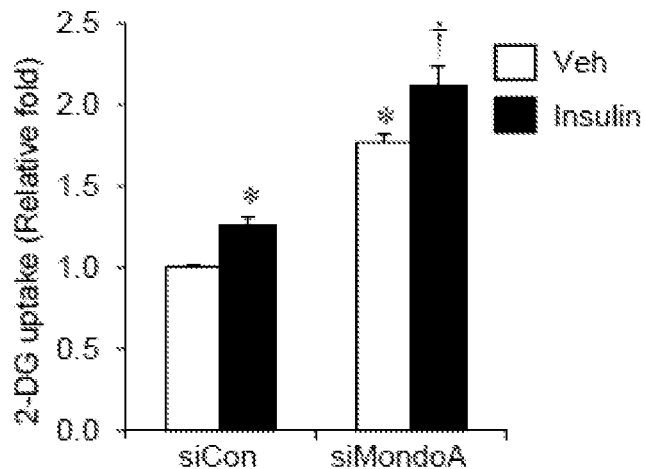

MondoA Coordinately Regulates Pathways Involved in Myocyte Glucose Uptake and TAG Synthesis siRNA-mediated knockdown (KD) studies were performed in human skeletal myocytes to determine whether inhibition of MondoA was responsible for the observed effects of SBI-477 on myocyte glucose uptake. Following MondoA (MLXIP) KD (FIG. 6G), expression of TXNIP and ARRDC4 was reduced to a similar degree as treatment with SBI-477 (FIGS. 6A and 6B). Insulin independent glucose uptake was enhanced following MondoA KD in human myotubes (FIG. 6C).

Figure 6D:
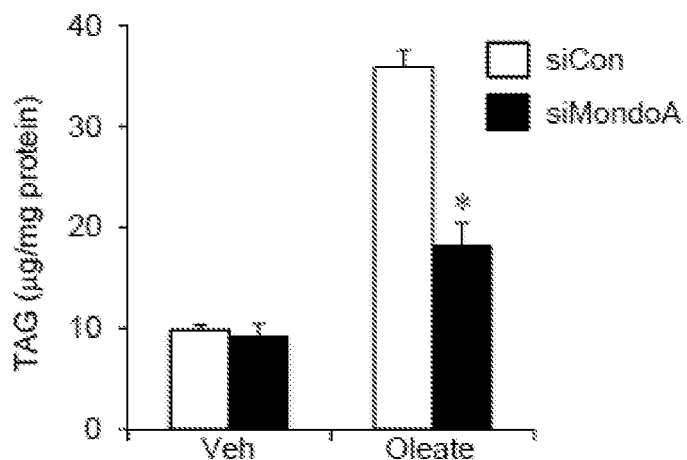
Figure 6E:
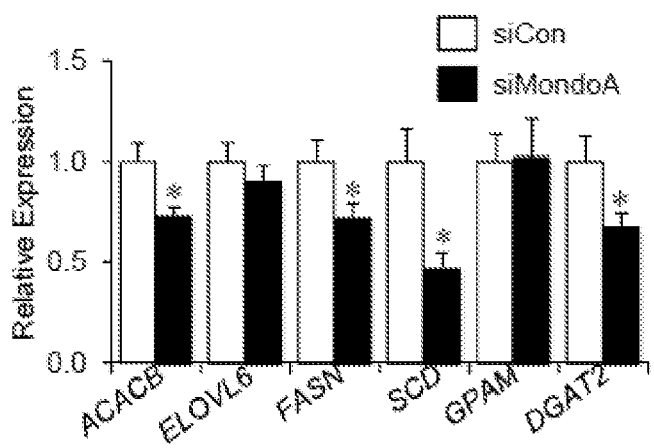
Figure 6F:
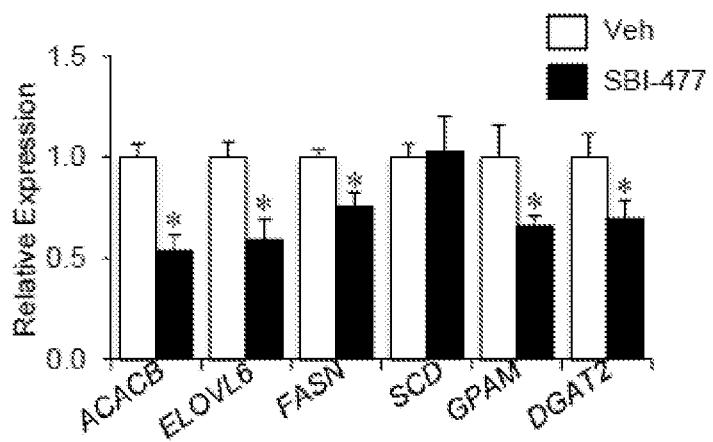
Figure 6G:
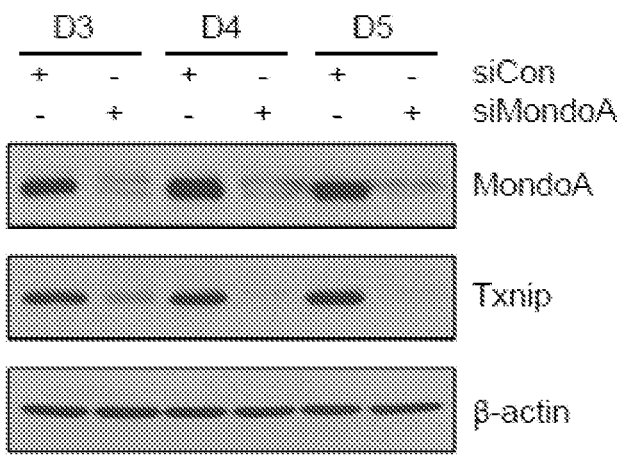
FIG. 6G shows MondoA and TXNIP protein levels as determined by immunoblotting on day 3, 4, and 5 after siMondoA or non-targeting control siRNA (siCon) knockdown in human myotubes.

MondoA KD also inhibited TAG accumulation following oleate loading (FIG. 6D). Given that the lipidomic studies implicated a mechanism targeting TAG synthesis, a determination was sought as to whether the SBI-477-MondoA pathway affected the expression of genes involved in this pathway. MondoA KD reduced the expression of several genes in the lipogenesis and TAG synthesis pathways including FASN, GPAM, EVOVL6, ACACB (ACCP) and DGAT2 (FIG. 6E). A very similar, although not identical, gene regulatory pattern was observed with SBI-477 treatment (FIG. 6F). Thus, depletion of MondoA reproduced the actions of SBI-477 on both glucose and lipid metabolism.

Figure 6H:
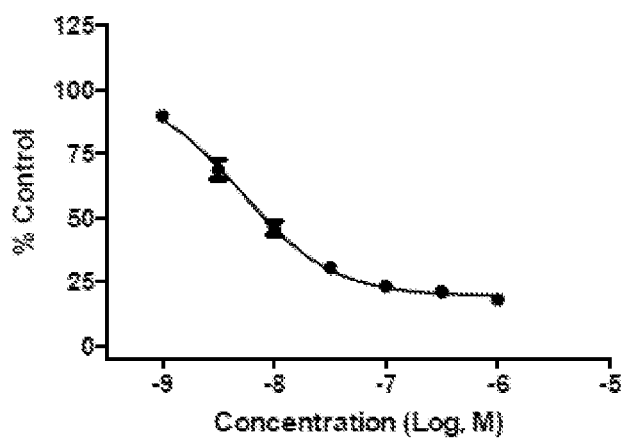
FIG. 6H shows a dose-response curve for the inhibition of triglyceride accumulation for SBI-993 in human skeletal myotubes.
Figure 6I:
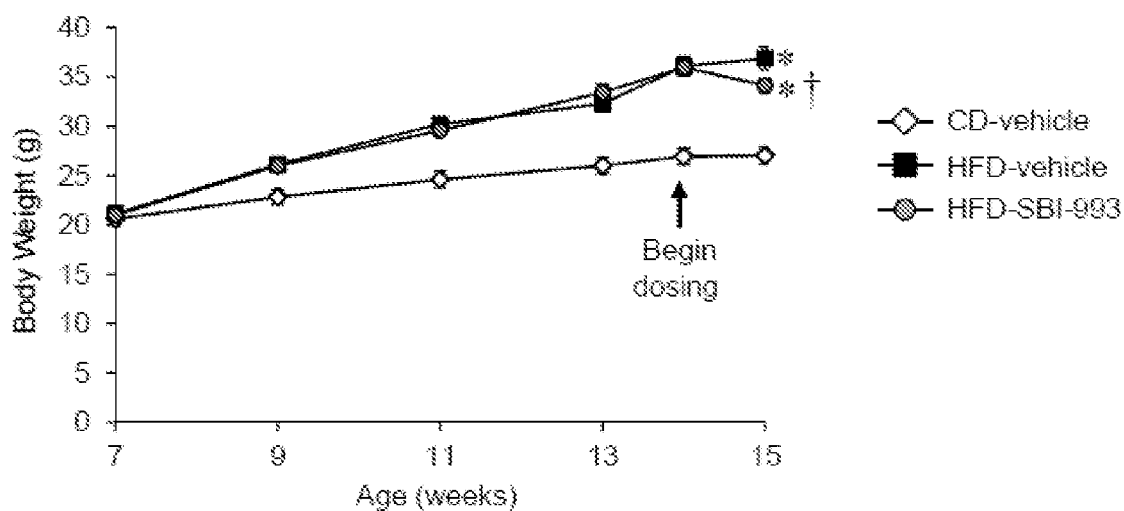
FIG. 6I shows body weight of mice over the study beginning at 7 weeks of age and start of high-fat diet (HFD) (n=6-10). Data represents mean±SEM. *p<0.05 vs. CD-vehicle; †p<0.05 vs. HFD-vehicle by one-way ANOVA.

To determine if the effects conferred by SBI-477 observed in myocytes in culture are relevant in vivo, studies were conducted in C57BL/6 mice with diet-induced obesity. For these studies, an analog of SBI-477, named SBI-993 was used, which exhibited improved potency and suitable pharmacokinetic properties for in vivo bioavailability (FIG. 6H). SBI-993 reduced TXNIP and ARRDC4 expression to a similar degree as SBI-477 in human myotubes (data not shown). Mice were fed a 60% high fat diet (HFD) for 8 weeks resulting in significant weight gain (FIG. 6I). During the final week of HFD feeding, SBI-993 or vehicle control was administered as a once daily dose (50 mg/kg s.c.) for 7 days. Plasma concentration of SBI-993 (4.97±0.97 µM) 4 hours following the final dose was above the cellular EC50. SBI-993 treatment resulted in a small but significant reduction in body weight as compared to vehicle (FIG. 6I).

Figure 7A:
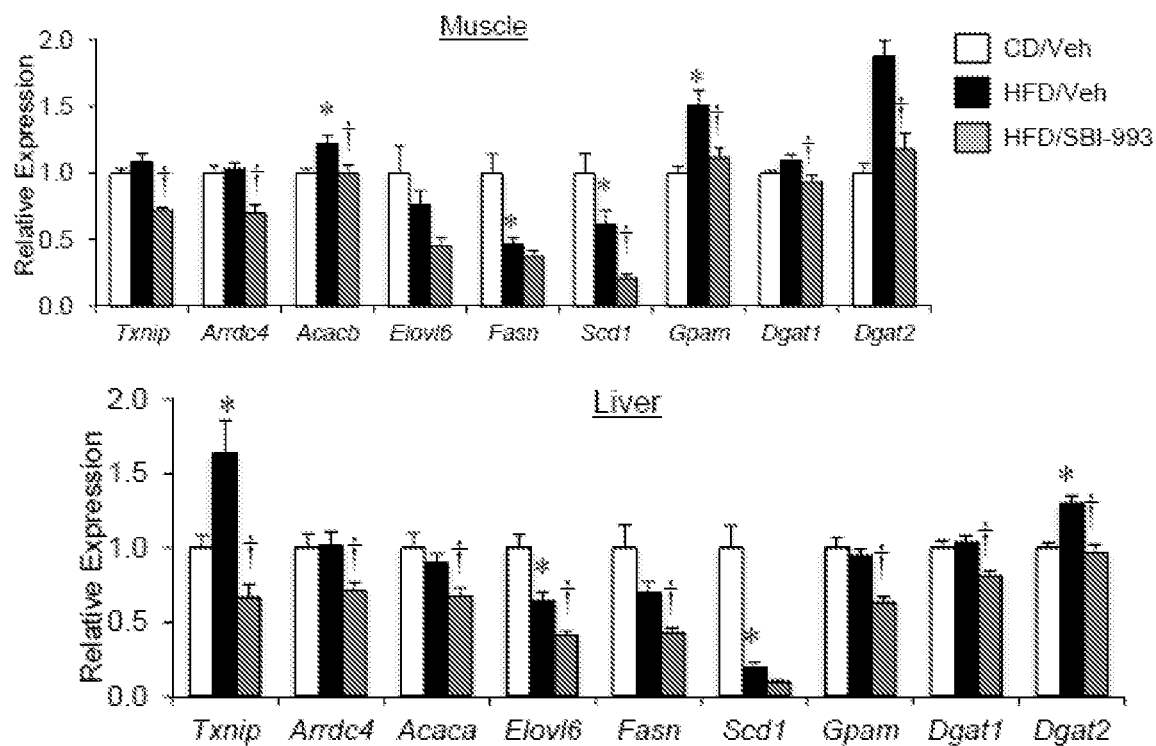
FIGS. 7A-D show SBI-993 inhibition of muscle and hepatic TAG accumulation and reduces MondoA target gene expression in vivo. Mice maintained on a high-fat diet for 8 weeks were administered SBI-993 (50 mg/kg, q.d., s.c.) or a vehicle (Veh) control for the final week of high-fat feeding. Target gene expression (FIG. 7A) and total triglyceride content (FIG. 7B) were measured in skeletal muscle (gastrocnemius) and liver in mice maintained on control diet (CD) or high-fat diet (HFD) (n=6-10 mice/group). *p<0.05 vs. CD/Veh, †p<0.05 vs. HFD/Veh by one-way ANOVA with Bonferroni post hoc test.

The effect of SBI-993 on MondoA target gene expression was used as a biomarker to confirm its expected actions in vivo. SBI-993 treatment reduced the expression of TAG synthesis and lipogenic genes in both muscle and liver (FIG. 7A). In addition, SBI-993 administration reduced Txnip and Arrdc4 expression, an effect that was especially robust in liver (FIG. 7A, bottom). ChIP analysis demonstrated that occupation of both ChREBP and MondoA on the Txnip and pyruvate kinase (Pklr) gene promoters was reduced in liver by SBI-993 (FIG. 7E).

Figure 7B:
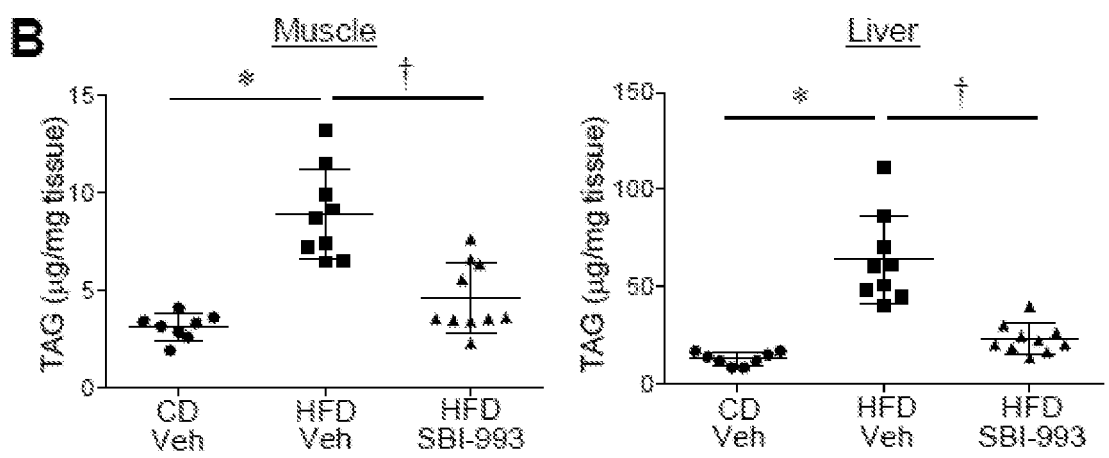
Figure 7C:
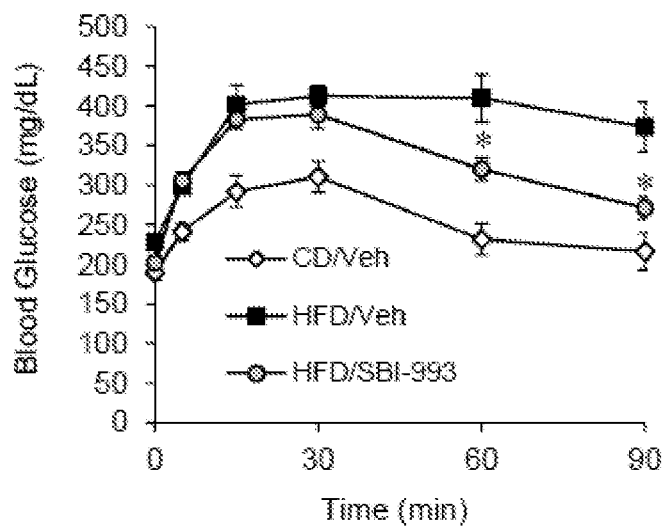
Figure 7D:
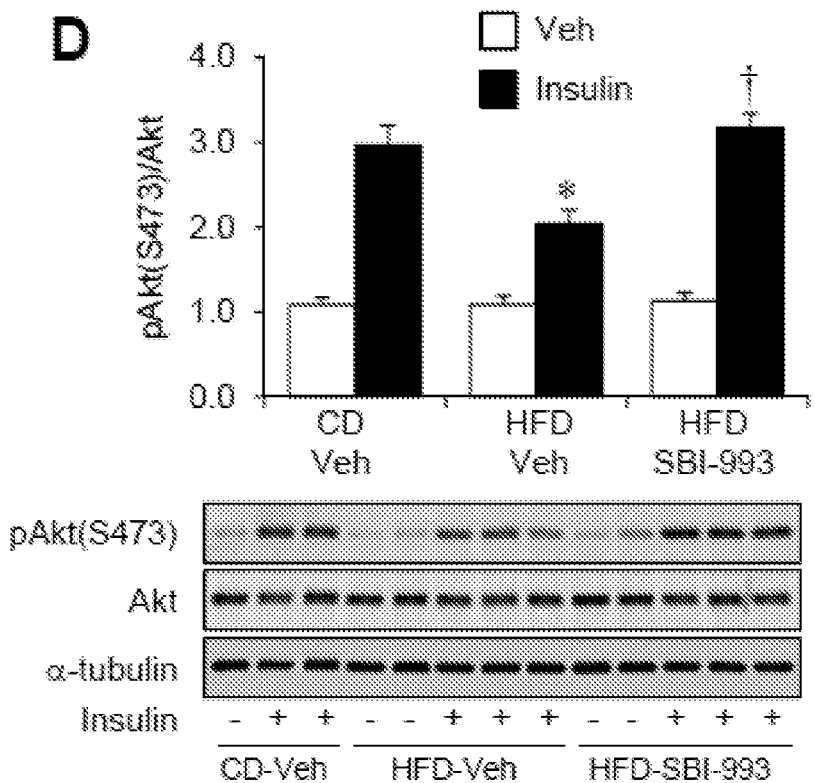
Figure 7E:
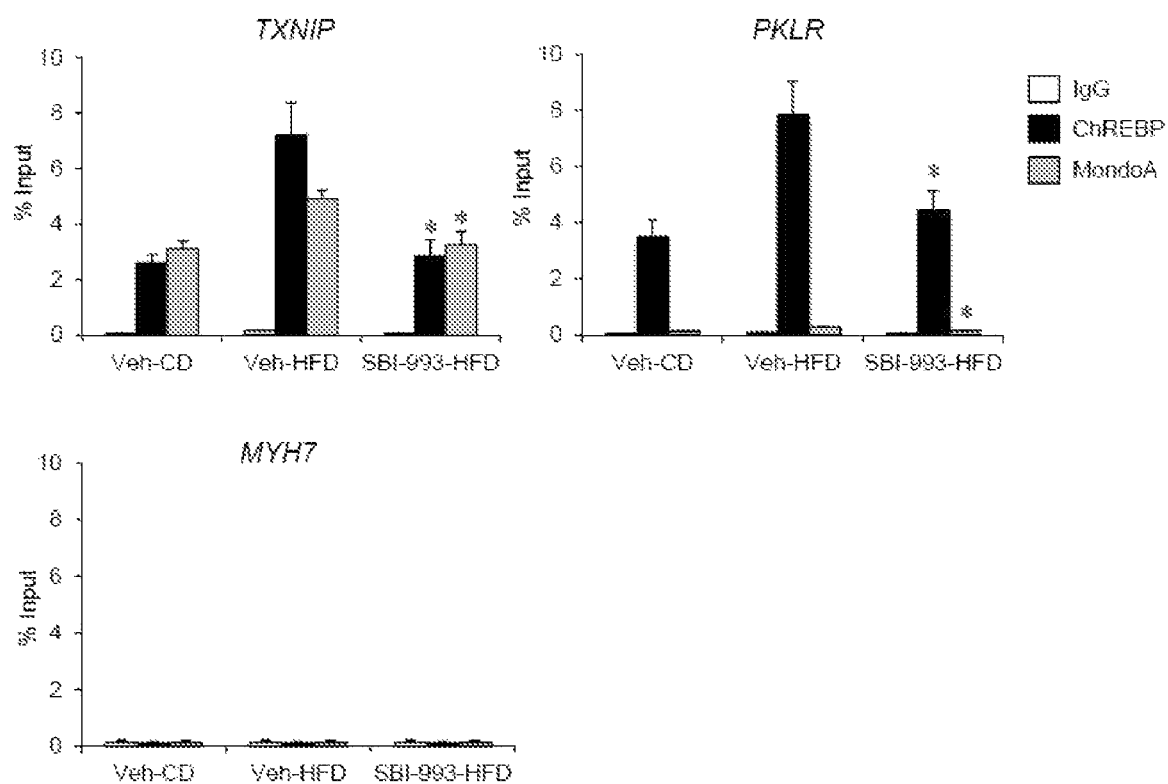
FIG. 7E shows SBI-993 reduction of ChREBP and MondoA occupation on target gene promoter elements in liver. ChIP-qPCR analysis was performed with nuclear extracts from liver tissue of mice following 1 week administration of SBI-993 or a vehicle control. Antibodies directed against ChREBP (black bars), MondoA (gray bars) or an IgG(open bars) control were used. Occupation of carbohydrate response elements from the Txnip and pyruvate kinase (Pklr) gene promoters is shown as % input. Occupation of an unrelated region within intron 26 of the Myh7 gene was used a negative control. *p<0.05 vs. Veh-HFD for indicated antibody by one-way ANOVA followed by Bonferroni post hoc test. CD, control diet; HFD, high fat diet.
Figure 7F:
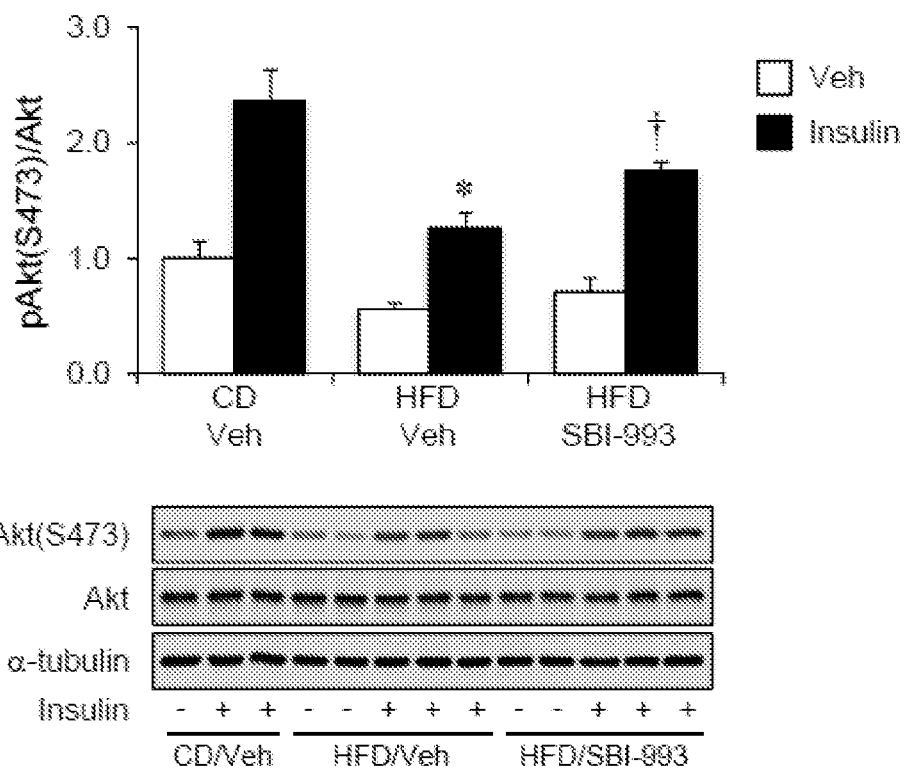
FIG. 7F shows SBI-993 inhibition of hepatic steatosis. Western blot analysis of liver whole cell lysates from mice receiving an acute insulin challenge (1.5 U/kg for 10 minutes) to examine insulin signaling using phosphorylated Akt (S473). Top panel is quantification of western blot analysis (n=4-6/condition). Representative western blots are shown in the bottom panel.

Consistent with the observed actions in vitro, TAG levels were significantly reduced in skeletal muscle following SBI-993 administration (FIG. 7B, left). Hepatic steatosis was also substantially ameliorated with compound treatment (FIG. 7B, right and data not shown). The decreased lipid deposition in liver and skeletal muscle was associated with improved glucose tolerance in mice administered SBI-993 (FIG. 7C). Finally, SBI-993 improved insulin signaling in both muscle and liver following an acute insulin challenge (FIGS. 7D and 7F). These data demonstrate that this compound class ameliorates obesity related lipotoxicity, including lipid accumulation and glucose tolerance, concomitant with reduced MondoA/ChREBP signaling and improved insulin action.

Discussion

Excessive cellular neutral lipid accumulation is a hallmark of caloric excess and obesity. It is now well established that expansion of intramyocellular lipid (IMCL) is strongly associated with the development of insulin resistance (Krssak, et al., *Diabetologia.* 1999; 42(1):113-116; Pan, et al., *J Clin Invest.* 1995; 96(6):2802-2808; Jacob, et al., *Diabetes.* 1999; 48(5):1113-1119; and Coen, et al., *Trends Endocrinol Metab.* 2012; 23(8):391-398). However, the intracellular lipid depot per se is likely not directly involved in this pathologic process, as insulin sensitive conditions may also be associated with increased IMCL such as is exhibited by endurance athletes (Goodpaster, et al., *J Clin Endocrinol Metab.* 2001; 86(12):5755-5761). Although specific lipid species such as diacylglycerols (DAG) and ceramides have been shown to contribute to muscle insulin resistance in some studies (Montell, et al., *Am J Physiol Endocrinol Metab.* 2001; 280(2):E229-237; Yu, et al., *J Biol Chem.* 2002; 277(52):50230-50236; Adams, et al. *Diabetes.* 2004; 53(1):25-31; Bergman, et al., *Diabetologia.* 2012; 55(4): 1140-1150; Szendroedi, et al., *Proc Natl Acad Sci USA.* 2014; 111(26):9597-9602.), this conclusion has not been consistently supported by all published work (Skovbro, et al., *Diabetologia.* 2008; 51(7):1253-1260; Anastasiou, at al., *Metabolism.* 2009; 58(11):1636-1642; Amati, et al., *Diabetes.* 2011; 60(10):2588-2597).

In addition, the normal biological processes that coordinately control myocyte lipid storage and glucose import are poorly understood. Therefore, an unbiased chemical biology screen was conducted to identify regulatory circuits that coordinately control myocyte lipid stores and glucose uptake. Delineation of the downstream actions of a molecule identified in this screen, revealed that the transcription factor, MondoA, coordinately regulates genes involved in myocyte TAG synthesis and TXNIP and ARRDC4, known inhibitors of insulin signaling. Thus, inhibition of MondoA by SBI-477 results in reduced cellular TAG accumulation and enhanced glucose uptake. This mechanism was shown to be operative in vivo in skeletal muscle and liver, suggesting that this regulatory pathway is relevant to multiple cell types.

MondoA was first described as a heterodimeric partner of the Mlx transcription factor (Billin, et al., *Mol Cell Biol.* 2000; 20(23):8845-8854). It has been proposed that MondoA, and its more intensively studied hepatic-enriched relative, ChREBP (MondoB), serve as intracellular glucose and energy sensors (Filhoulaud, et al., *Trends Endocrinol Metab.* 2013; 24(5):257-268; Dentin, et al., *J Biol Chem.* 2004; 279(19):20314-20326; Peterson, et al., *Mol Cell Biol.* 2010; 30(12):2887-2895). Increased levels of glucose-6-phosphate and other carbohydrate intermediates have been shown to stimulate the nuclear import of ChREBP and MondoA resulting in a feedback loop that results in the control of glucose uptake and metabolism (Stoltzman, et al., *Proc Natl Acad Sci USA.* 2008; 105(19):6912-6917; Peterson, at al., *Mol Cell Biol.* 2010; 30(12):2887-2895; Kabashima, et al., *Proc Natl Acad Sci USA.* 2003; 100(9):5107-5112; Sakiyama, et al, *J Biol Chem.* 2008; 283(36):24899-24908; Stoltzman, et al., *J Biol Chem.* 2011; 286(44):38027-38034). The results described herein demonstrate that MondoA activates expression of genes involved in myocyte TAG synthesis and de novo lipogenesis. This regulation is reminiscent of the effects of ChREBP on hepatic lipogenesis (Dentin, et al., *Diabetes.* 2006; 55(8):2159-2170; Iizuka, et al., *Am J Physiol Endocrinol Metab.* 2006; 291(2):E358-364). Depletion of MondoA reduced TAG levels in oleate-loaded myocytes, an effect that mimicked the inhibitory effects of SBI-477. This mechanism was also shown in vivo as administration of SBI-993 resulted in a reduction in muscle TAG levels and reduced hepatic steatosis associated with reduced expression of lipogenic and TAG synthesis genes. MondoA suppresses myocyte glucose uptake via activation of the α-arrestin proteins TXNIP and ARRDC4, establishing a negative feedback loop to restrict glucose entry (Stoltzman, et al., *Proc Natl Acad Sci USA.* 2008; 105(19):6912-6917; Kaadige, et al., *Proc Natl Acad Sci USA.* 2009; 106(35):14878-14883).

Overexpression of either TXNIP or ARRDC4 inhibits cellular glucose uptake (Parikh, et al., *PLoS Med* 2007; 4(5):e158; Patwari, et al. *J Biol Chem.* 2009; 284(37): 24996-25003) by repressing insulin signaling via mechanisms that are as yet undetermined (Yoshihara, et al., *Nat Commun.* 2010; 1:127). Interestingly, TXNIP expression is increased in human skeletal muscle of type 2 diabetes patients and inversely correlated with insulin-stimulated glucose uptake (Parikh, et al., *PLoS Med.* 2007; 4(5):e158;). In addition, deletion of TXNIP in the ob/ob background improved insulin sensitivity with activation of the insulin signaling pathway in skeletal muscle (Yoshihara, et al., *Nat Commun.* 2010; 1:127). SBI-477 administration phenocopied the effects on TXNIP and ARRDC4 expression observed with MondoA depletion in skeletal myocytes, resulting in enhanced cellular glucose uptake. SBI-477 exerts this effect by markedly reducing nuclear levels of MondoA.

The MondoA-mediated mechanism described here was identified by a cell-based phenotypic small molecule screen. Phenotypic screens allow for unbiased identification of molecules that function as probes of specific cellular processes and mechanisms with high relevance to biology and disease. However, a current challenge of phenotypic screens relates to the difficulty in identifying the direct molecular target. While not being bound by theory, it is possible that SBI-477 directly targets enzymes involved in de novo lipogenesis or TAG synthesis. Targets such as DGAT, MGAT or SCD-1 were ruled out, but the possibility that SBI-477 inhibits other enzymes in this or related pathways cannot be excluded yet. However, the results are consistent with a mechanism that imposes upstream control of MondoA signaling. SBI-477 may also affect the level of an intracellular signal that controls nuclear localization of both MondoA and ChREBP. Indeed, previous studies have identified several candidate mediators for the control of ChREBP/MondoA cellular localization and activity including intermediates of glucose metabolism, OGlcNAc modification, and phosphorylation (Peterson, at al., *Mol Cell Biol.* 2010; 30(12):2887-2895, Sakiyama, et al, *J Biol Chem.* 2008; 283(36):24899-24908; Kawaguchi; at al., *Proc Natl Acad Sci USA.* 2001; 98(24):13710-13715; Bricambert, et al., *J Clin Invest.* 2010; 120(12):4316-4331; Guinez, et al., *Diabetes.* 2011; 60(5):1399-1413). However, given the impact of SBI-477 on lipid metabolism, it is also possible that a lipid signal influences MondoA nuclear localization.

Figure 8:
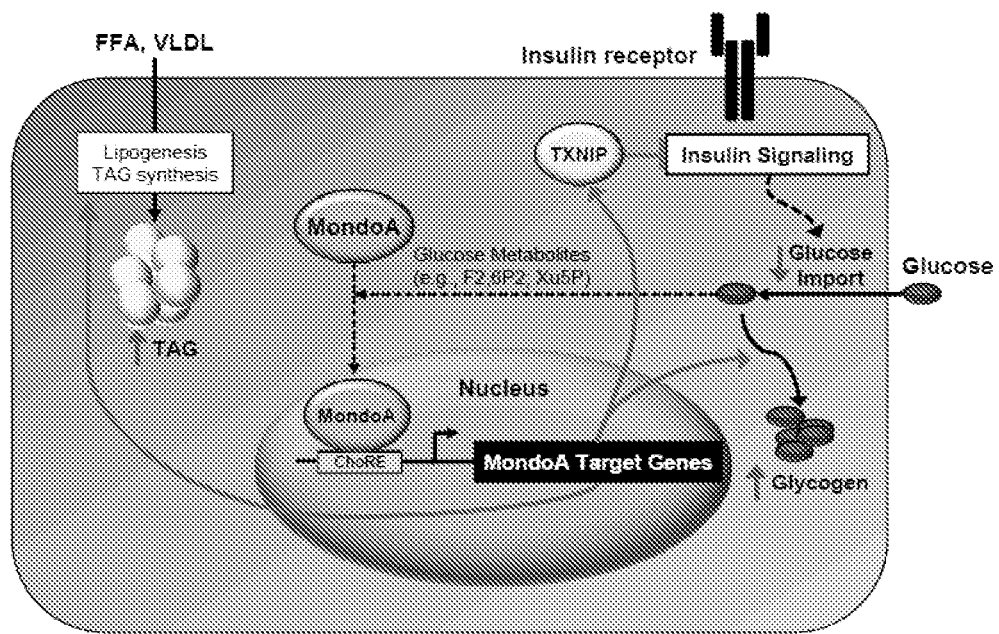
FIG. 8 is a schematic showing how MondoA directs myocyte fuel homeostatic checkpoint functions. The proposed gene regulatory (red arrows) and metabolic "checkpoint" responses (blue arrows) downstream of MondoA are shown. MondoA is a glucose "sensor", directly activated by glycolytic metabolites that stimulate nuclear import of MondoA. Once activated, MondoA functions as a "brake" to limit carbon entry into the cell via increasing levels of TXNIP, an inhibitor of insulin signaling and glucose uptake. In addition, MondoA promotes energy storage through activation of enzymes involved in lipid and glycogen synthesis. Thus, MondoA may serve to limit carbon intake and fuel burning during conditions of "plenty". However, in states of chronic nutrient excess, persistent activation of MondoA may become maladaptive, contributing to a vicious cycle of cellular lipid accumulation (TAG synthesis) and insulin resistance (TXNIP-mediated suppressive effects). FFA, free fatty acid; VLDL, very low-density lipoprotein; ChoRE, carbohydrate response element; TXNIP, thioredoxin-interacting protein.

The results described suggest a role of MondoA signaling in muscle. MondoA may serve to maintain cellular carbon and energy homeostasis. Specifically, in states of acute fuel excess and ample energy stores, MondoA may serve to reduce fuel catabolism by triggering metabolic checkpoint functions that redirect carbon sources by inhibiting glucose uptake via suppression of insulin signaling, and incorporation of fatty acids into lipid storage depots (FIG. 8). MondoA has also been shown to activate genes involved in glycogen synthesis, further supporting a role in diversion of fuel to storage depots (Petrie, et al., *Mol Cell Biol.* 2013; 33(4):725-738). The known mechanisms of MondoA regulation are also consistent with this notion. For example, MondoA nuclear levels are increased by glucose metabolites, including phosphometabolites, which could serve as indicators of high glucose flux and ample energy phosphate stores (Petrie, et al., *Mol Cell Biol.* 2013; 33(4):725-738; Sloan, et al., *Genes Cancer.* 2010; 1(6):587-596). In addition, inhibition of oxidative phosphorylation results in deactivation of MondoA, which would release its inhibition on glucose import and fuel catabolic flux (Yu, et al., *J Biol Chem.* 2010; 285(33):25822-25830). Accordingly, MondoA may serve to limit carbon intake and fuel burning during periods of acute fuel excess. In states of chronic caloric excess, persistent activation of MondoA may become maladaptive (FIG. 8), contributing to a vicious cycle of cellular lipid accumulation (TAG synthesis) and insulin resistance (TXNIP-mediated effects).

The findings demonstrate that the regulatory circuit defined in the cell studies is operative in vivo.

Following administration of a high fat diet in mice, a structural homolog of SBI-477, SBI-993, reduced TAG levels in muscle, and to a greater extent in liver. The reduction of intramyocellular and hepatic triglyceride accumulation was associated with improved insulin signaling and glucose tolerance. It should be noted that the compound caused modest weight loss. Some contribution to the metabolic effects of SBI-993 by the modest weight loss effects cannot be excluded. Notably, the weight loss was not due to reduced food intake (data not shown) making a generalized toxic effect of the compound unlikely. In addition, the effects on tissue lipids and Txnip gene expression were disproportionate to the modest weight loss. Interestingly, the ChIP results demonstrated that SBI-993 reduced occupation of ChREBP in addition to MondoA on liver target genes, suggesting that the compound likely affects both MondoA and ChREBP in liver. Taken together, the findings provide a therapeutic target for insulin resistance and tissue lipotoxicity caused by chronic caloric excess.

Preparation of Compounds Using General Synthetic Schemes

Compounds Prepared Using Scheme 3

3-methoxy-N-(4-(4-methoxyphenyl)thiazol-2-yl)-4-((2-morpholino-2-oxoethyl)amino)benzamide (Cpd. 75)

The commercially available 3-methoxy-4-nitrobenzoic acid (1.0 eq) was dissolved in acetonitrile (0.25 M) and treated with triethylamine (2.0 eq) and HATU (1.0 eq). To this mixture was then added 4-(4-methoxyphenyl)thiazol-2-amine (1.0 eq). The resulting solution was warmed to 65° C. and stirred until the reaction was complete. At this time the solution was cooled to room temperature and diluted with water. The resulting precipitate was collected via filtration, washed with additional water, and dried in vacuo to give 3-methoxy-N-(4-(4-methoxyphenyl)thiazol-2-yl)-4-nitrobenzamide as a pale yellow solid (82% yield). A dry round bottom flask was charged with 10% palladium on carbon (0.05 eq) under an atmosphere of nitrogen. EtOAc (~0.2 M) was then added, followed by 3-methoxy-N-(4-(4-methoxyphenyl)thiazol-2-yl)-4-nitrobenzamide (1.0 eq). A hydrogen-filled balloon was then affixed to the flask and the airspace was evacuated and back-filled with hydrogen. The mixture was vigorously stirred until the reaction was complete, adding additional catalyst as needed and some methanol to ensure solubility. The mixture was then filtered through celite, washing with methanol to give 3-methoxy-N-(4-(4-methoxyphenyl)thiazol-2-yl)-4-nitrobenzamide as a yellow solid. This solid (1.0 eq) was then dissolved in acetonitrile (0.1 M) and treated with excess glyoxylic acid (~15 eq of a 50% aqueous solution). Sodium cyanoborohydride (5.0 eq) was then added and stirred at room temperature until the reaction was complete. The solution was then quenched with acetic acid, and partitioned between EtOAc and 1N HCl. The organic portion was then concentrated to a yellow solid that was used without further purification. The crude (2-methoxy-4-((4-(4-methoxyphenyl)thiazol-2-yl)carbamoyl) phenyl)glycine (1.0 eq) was dissolved in DMF and treated with morpholine (10.0 eq). To this room temperature solution was added HATU (3.0 eq) and stirring was continued until the reaction was complete. The solution was then quenched with water which initiated the formation of a white precipitate. This impure solid was collected via filtration and then purified on silica gel (hexane/EtOAc gradient 35%-100%) to give 3-methoxy-N-(4-(4-methoxyphenyl)thiazol-2-yl)-4-((2-morpholino-2-oxoethyl)amino) benzamide as a white solid. $^1$H-NMR (DMSO-$d_6$, 500 MHz): δ 12.33 (s, 1H), 7.88 (d, J=8.8 Hz, 2H), 7.75 (dd, J=8.3, 1.9 Hz, 1H), 7.67 (d, J=2.0 Hz, 1H), 7.44 (s, 1H), 7.00 (d, J=8.9 Hz, 2H), 6.67 (d, J=8.5 Hz, 1H), 5.84 (t, J=4.6 Hz, 1H), 4.05 (d, J=4.6 Hz, 2H), 3.94 (s, 3H), 3.79 (s, 3H), 3.63 (br, 2H), 3.58 (br, 2H), 3.51 (br, 4H). $^{13}$C-NMR (DMSO-$d_6$, 125 MHz): δ 167.19, 164.61, 158.90, 158.87, 148.82, 145.38, 141.20, 127.36, 127.05, 123.02, 118.38, 114.02, 108.83, 108.75, 106.03, 65.98, 65.90, 55.72, 55.12, 44.28, 43.82, 41.87. MS [M+H]: 483.22.

N-(4-(4-methoxyphenyl)thiazol-2-yl)-4-(2-morpholinoethoxy)benzamide (Cpd. 78)

A vial was charged with commercially available 4-(2-morpholinoethoxy)benzoic acid (1.2 eq), 4-(4-methoxyphenyl)thiazol-2-amine (1.0 eq), and anhydrous DMF (0.15 M). To this solution was then added triethylamine (2.0 eq), then HATU (1.2 eq). The mixture was then warmed to 75° C. and stirred until the reaction was complete. The solution was then cooled to room temperature, diluted with water and extracted with EtOAc. The organic portion was then washed with brine and dried over sodium sulfate.

Concentration in vacuo and purification on silica gel ($CH_2Cl_2$/MeOH gradient) gave N-(4-(4-methoxyphenyl)thiazol-2-yl)-4-(2-morpholinoethoxy)benzamide. $^1$H-NMR (MeOD-$d_4$, 500 MHz): δ 8.03 (d, J=8.9 Hz, 2H), 7.86 (d, J=8.7 Hz, 2H), 7.25 (s, 1H), 7.11 (d, J=8.8 Hz, 2H), 6.96 (d, J=8.7 Hz, 2H), 4.25 (t, J=5.3 Hz, 2H), 3.83 (s, 3H), 3.76-3.70 (m, 4H), 2.89-2.81 (m, 3H), 2.62 (m, 4H). MS [M+H]: 440.31.
Compounds Prepared Using Scheme 4

4-(2,3-dihydro-4H-benzo[b][1,4]oxazin-4-yl)-N-(4-(4-methoxyphenyl)thiazol-2-yl)-4-oxobutanamide (Cpd. 81)

A microwave vial was charged with 3,4-dihydro-2H-benzo[b][1,4]oxazine (1.0 eq), succinic anhydride (1.0 eq) and acetonitrile (0.33 M) and heated at 100° C. for 30 min. To this room temperature solution was then added triethylamine (2.0 eq), 4-(4-methoxyphenyl)thiazol-2-amine (1.0 eq), and HATU (1.2 eq). The solution was again heated to 100° C. for 45 minutes. After cooling to room temperature, the solution was diluted with water which initiated the precipitation of a solid. This solid was collected via filtration and then further purified on silica gel (hexane/EtOAc gradient 5%-80%) to give 4-(2,3-dihydro-4H-benzo[b][1,4] oxazin-4-yl)-N-(4-(4-methoxyphenyl)thiazol-2-yl)-4-oxobutanamide as a white solid. $^1$H-NMR (CDCl$_3$, 500 MHz): δ 9.81 (s, 1H), 7.75 (d, J=8.8 Hz, 2H), 7.10 (s, 1H), 6.98 (s, 1H), 6.95-6.87 (m, 4H), 4.31 (m, 2H), 3.98 (br, 2H), 3.83 (s, 3H), 3.04 (br, 2H), 2.81 (m, 2H). MS [M+H]: 424.28.

N-(4-(4-methoxyphenyl)thiazol-2-yl)-4-morpholino-4-oxobutanamide (Cpd. 82)

A microwave vial was charged with morpholine (1.0 eq), succinic anhydride (1.0 eq) and acetonitrile (0.4 M) and heated at 100° C. for 30 min. To this room temperature solution was then added triethylamine (2.0 eq), 4-(4-methoxyphenyl)thiazol-2-amine (1.0 eq), and HATU (1.2 eq). The solution was again heated to 100° C. for 45 minutes. After cooling to room temperature, the solution was diluted with water. The solid thus formed did not dissolve in water, or in EtOAc. This solid was collected via filtration and was shown to be clean N-(4-(4-methoxyphenyl)thiazol-2-yl)-4-morpholino-4-oxobutanamide. $^1$H-NMR (CDCl$_3$, 500 MHz): δ 10.23 (s, 1H), 7.75 (d, J=8.8 Hz, 2H), 6.97 (s, 1H), 6.93 (d, J=8.8 Hz, 2H), 3.84 (s, 3H), 3.69 (m Hz, 6H), 3.56-3.48 (m, 2H), 2.89-2.82 (m, 2H), 2.81-2.76 (m, 2H). $^{13}$C-NMR (CDCl$_3$, 125 MHz): δ 170.44, 170.35, 159.75, 157.75, 149.70, 127.56, 127.47, 114.28, 105.96, 67.03, 66.63, 55.56, 45.97, 42.55, 31.60, 28.50. MS [M+H]: 376.14.
Compounds Prepared Using Scheme 5

Scheme 5

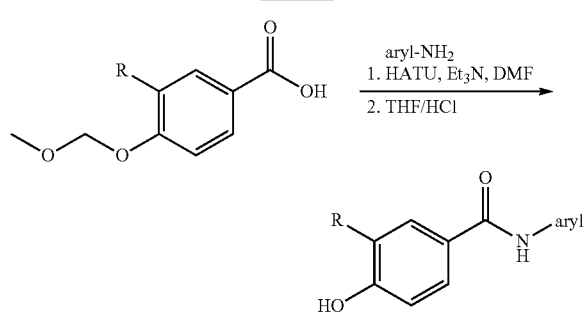

A vial was charged with the arylamine (1.0 eq), triethylamine (3.0 eq), and DMF (~0.4 M). To this solution was then added the 3-methoxy-4-(methoxymethoxy)benzoic acid (1.2 eq). Finally, HATU (1.2 eq) was added and the vial was warmed to 75° C. Stirring at 75° C. was continued until full consumption of the carboxylic acid by LCMS. The solution was then cooled to room temperature, diluted with EtOAc, and washed with water and brine. Concentration in vacuo gave an oil that was used without further purification. This oil was directly dissolved in THF (2 mL) and treated with 1N HCl (0.5 mL). The solution was then warmed to 65° C. and stirred until the acetal deprotection was complete by LCMS. Upon completion, the solution was cooled to room temperature, diluted with EtOAc and sequentially washed with water and brine. The solution was dried over sodium sulfate, concentrated in vacuo, and purified on silica gel (hex/EtOAc gradient) to give the clean phenol.

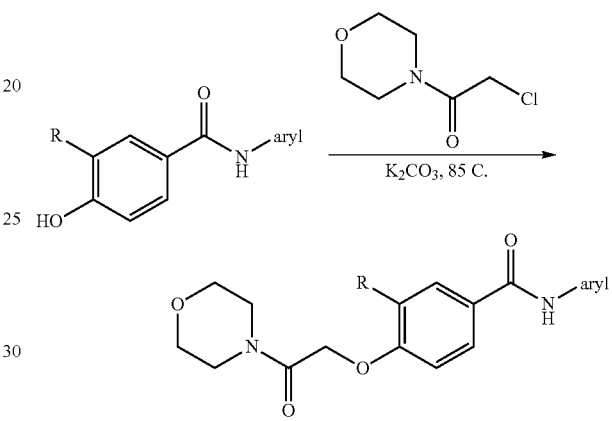

A vial was charged with the phenol (1.0 eq) and acetonitrile (0.3 M). Potassium carbonate (2.0 eq) was added, followed by 2-chloro-1-morpholinoethan-1-one (1.0 eq). This solution was then warmed to 85° C. and stirred for 4-5 h. The solution was cooled to room temperature and diluted with water and twice extracted with EtOAc. Purification on silica gel (hex/EtOAc gradient 10%-100%) gave the expected product.

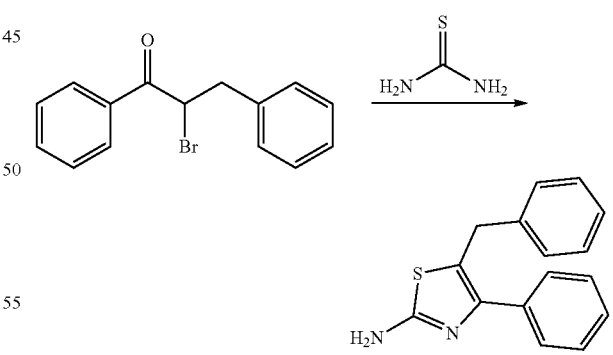

A microwave vial was charged with 2-bromo-1,3-diphenylpropan-1-one (1.0 eq), thiourea (1.05 eq), and ethanol (0.2 M). The mixture was heated at 60° C. for 15 min and then partitioned between water and dichloromethane. The organic portion was then dried over sodium sulfate and concentrated in vacuo. Purification on silica gel gave 5-benzyl-4-phenylthiazol-2-amine (69% yield). $^1$H-NMR (500 MHz, CDCl$_3$) δ 7.44-7.40 (m, 2H), 7.30 (m, 3H), 7.24-7.19 (m, 2H), 7.12 (m, 3H), 3.97 (s, 2H), 3.27 (m, 2H).

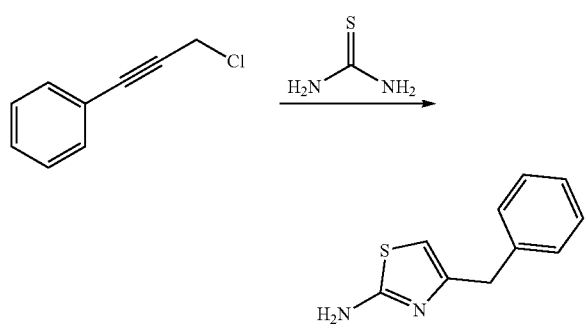

A microwave vial was charged with (3-chloroprop-1-yn-1-yl)benzene (1.0 eq), thiourea (1.0 eq) and acetonitrile (0.25 M). Potassium carbonate (1.0 eq) was then added and the combined mixture was heated at 110° C. for 30 min. The solution was then diluted with water and extracted with EtOAc. The organic portion was concentrated in vacuo and purified on silica gel (hexane/EtOAc gradient 2%-65%) to give 4-benzylthiazol-2-amine. $^1$H-NMR (500 MHz, CDCl$_3$) δ 7.31 (m, 2H), 7.27 (m, 2H), 7.23 (m, 1H), 6.01 (s, 1H), 5.43 (s, 2H), 3.89 (s, 2H).

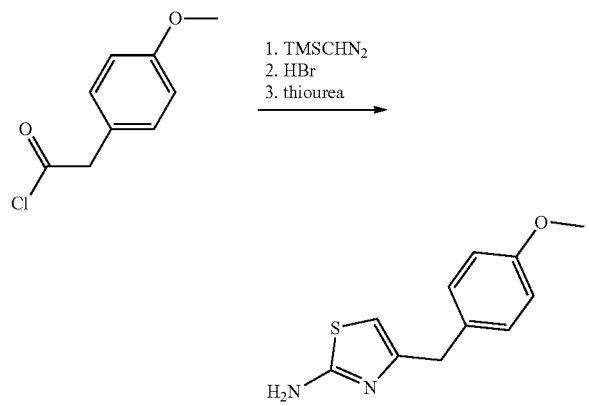

A flask was charged with 2-(4-methoxyphenyl)acetyl chloride (1.0 eq) and MeCN at room temperature. Trimethylsilyl diazomethane (5.2 eq) was carefully added dropwise to the solution. The resulting mixture was stirred for 3 h and then concentrated in vacuo to give an orange oil. This oil was then dissolved in THF (0.5 M) and treated with HBr (33%, 5.2 eq) at 0° C. After 1 h, the solution was poured into water and extracted with EtOAc. The organic portion was dried over magnesium sulfate and concentrated in vacuo. This 1-bromo-3-(4-methoxyphenyl)propan-2-one (1.0 eq) was then dissolved in EtOH and treated with thiourea (1.9 eq). The mixture was then warmed to 75° C. for 1 h. The solution was partitioned between EtOAc and water, and then dried over magnesium sulfate. Concentration and purification on silica gel (hexane/EtOAc gradient 10%-100%) gave 4-(4-methoxybenzyl)thiazol-2-amine. $^1$H-NMR (500 MHz, Chloroform-d) δ 7.17 (d, J=8.6 Hz, 2H), 6.84 (d, J=8.6 Hz, 2H), 5.98 (t, J=1.1 Hz, 1H), 5.08 (br, 2H), 3.80 (s, 2H), 3.79 (s, 3H).

2-(2-methoxy-4-(((4-(4-methoxyphenyl)thiazol-2-yl)amino)methyl)phenoxy)-1-morpholinoethan-1-one (Cpd. 89)

A microwave vial was charged with 3-methoxy-4-(methoxymethoxy)-N-(4-(4-methoxyphenyl)thiazol-2-yl) benzamide (1.0 eq) and THF (0.1 M). BH$_3$.THF (15 eq of a 1.0 M solution) was carefully added and the solution was heated to 75° C. for 60 min. The solution was then quenched with aqueous HCl and then warmed again to 75° C. for 30 min at which time the acetal deprotection was complete. The solution was then diluted with EtOAc and washed with NaHCO$_3$ and brine. The organic portion was dried over sodium sulfate, concentrated in vacuo, and purified on silica gel (hexane/EtOAc gradient 10%-40%) to give 2-methoxy-4-(((4-(4-methoxyphenyl)thiazol-2-yl)amino)methyl)phenol. This phenol (1.0 eq) was then dissolved in acetonitrile (0.1 M) and treated with 2-chloro-1-morpholinoethan-1-one (1.0 eq) and potassium carbonate (2.0 eq). This mixture was heated in a microwave at 85° C. for 4 h. The inorganic salts were then removed via filtration and the filtrate was concentrated in vacuo. Purification on silica gel (hexane/acetone gradient) gave 2-(2-methoxy-4-(((4-(4-methoxyphenyl)thiazol-2-yl)amino)methyl)phenoxy)-1-morpholinoethan-1-one. $^1$H-NMR (500 MHz, CDCl$_3$) δ 7.73 (d, J=8.8 Hz, 2H), 6.95 (d, J=1.7 Hz, 1H), 6.93-6.88 (m, 4H), 6.57 (s, 1H), 5.70 (br, 1H), 4.73 (s, 2H), 4.43 (d, J=4.2 Hz, 2H), 3.83 (s, 3H), 3.83 (s, 3H), 3.65 (m, 8H). MS [M+H]: 470.25.

3-methoxy-N-(4-(4-methoxyphenyl)thiazol-2-yl)-4-(2-morpholinoethoxy)benzamide (Cpd. 90)

A microwave vial was charged with ethyl 3-methoxy-4-(2-morpholino-2-oxoethoxy)benzoate (1.0 eq) and THF (0.1 M). BH$_3$.THF (15 eq of a 1.0 M solution) was carefully added and the resulting solution was warmed to 75° C. for 1 h. This solution was quenched with water and concentrated in vacuo. The material was then dissolved in THF/water (2:1) and treated with LiOH (5 eq). This mixture was then heated at 85° C. for 1 h and concentrated in vacuo. This material was then treated with acetonitrile (0.1 M), triethylamine (4.0 eq) and HATU (1.0 eq). 4-(4-methoxyphenyl)thiazol-2-amine (1.0 eq) was then added and the combined solution was warmed to 65° C. The reaction was sluggish, so additional HATU was added as needed to complete the reaction. The solution was then quenched with water and thrice extracted with EtOAc. The combined organics were dried over sodium sulfate and concentrated in vacuo. Purification on silica gel (hexane/acetone gradient) gave 3-methoxy-N-(4-(4-methoxyphenyl)thiazol-2-yl)-4-(2-morpholinoethoxy)benzamide. $^1$H-NMR (CDCl$_3$, 500 MHz): δ 9.59 (s, 1H), 7.75 (d, J=8.8 Hz, 2H), 7.53 (d, J=2.1 Hz, 1H), 7.46 (dd, J=8.4, 2.1 Hz, 1H), 7.05 (s, 1H), 6.97-6.92 (m, 3H), 4.25 (t, J=6.0 Hz, 2H), 3.93 (s, 3H), 3.85 (s, 3H), 3.76 (t, J=4.7 Hz, 4H), 2.92 (t, J=6.0 Hz, 2H), 2.66 (br, 4H). MS [M+H]: 470.23.

N-(3-methoxy-4-(2-morpholino-2-oxoethoxy)phenyl)-4-(4-methoxyphenyl)thiazole-2-carboxamide (Cpd. 91)

A microwave vial was sequentially charged with 2-methoxy-4-nitrophenol (1.0 eq), MeCN (0.2 M), 2-chloro-1-morpholinoethan-1-one (1.0 eq) and potassium carbonate (2.0 eq). The mixture was heated at 120° C. until the reaction was complete, at which time the inorganic solids were removed via filtration and the filtrate was concentrated in vacuo to give 2-(2-methoxy-4-nitrophenoxy)-1-morpholinoethan-1-one as a yellow solid. $^1$H-NMR (500 MHz, CDCl$_3$) δ 7.88 (dd, J=8.9, 2.6 Hz, 1H), 7.78 (d, J=2.6 Hz, 1H), 6.99 (d, J=8.9 Hz, 1H), 4.86 (s, 2H), 3.96 (s, 3H), 3.67 (t, J=4.5 Hz, 4H), 3.62 (dd, J=10.7, 4.9 Hz, 3H). A round bottom flask was then charged with Pd/C (10%, 0.05 eq) and EtOAc (0.2

M) under an atmosphere of nitrogen. 2-(2-methoxy-4-nitrophenoxy)-1-morpholinoethan-1-one (1.0 eq) was then added, followed by MeOH (0.3 M) to aid in dissolution. A hydrogen-filled balloon was affixed to the flask and the mixture was vigorously stirred overnight. Upon completion, the mixture was filtered through celite and washed with methanol. Concentration in vacuo gave 2-(4-amino-2-methoxyphenoxy)-1-morpholinoethan-1-one. $^1$H-NMR (500 MHz, CDCl$_3$) δ 6.80 (d, J=8.5 Hz, 1H), 6.30 (d, J=2.6 Hz, 1H), 6.20 (dd, J=8.4, 2.6 Hz, 1H), 4.63 (s, 2H), 3.80 (s, 3H), 3.71-3.59 (m, 8H). A microwave tube was charged with ethyl 2-amino-2-thioxoacetate (1.0 eq), 2-bromo-1-(4-methoxyphenyl)ethan-1-one (1.0 eq), and aqueous EtOH (0.5 M, 50%). The solution was then heated at 75° C. for 60 min. The solution was poured into water and extracted with dichloromethane. Concentration in vacuo and purification on silica gel (hexane/EtOAc gradient 20%-50%) gave ethyl 4-(4-methoxyphenyl)thiazole-2-carboxylate. $^1$H-NMR (500 MHz, CDCl$_3$) δ 7.90 (d, J=8.8 Hz, 2H), 7.62 (s, 1H), 6.96 (d, J=8.9 Hz, 2H), 4.51 (q, J=7.1 Hz, 2H), 3.86 (s, 3H), 1.46 (t, J=7.1 Hz, 3H). This material (1.0 eq) was then dissolved in aqueous THF (0.3 M, 4:1 THF:H$_2$O) and treated with LiOH (4.0 eq). The mixture was stirred for 60 min, then poured into aqueous HCl (1 N) and extracted twice with dichloromethane. The organic portions were combined, dried over sodium sulfate, and concentrated in vacuo to give 4-(4-methoxyphenyl)thiazole-2-carboxylic acid as a yellow solid. A vial was then charged with 4-(4-methoxyphenyl)thiazole-2-carboxylic acid (1.0 eq) and 2-(4-amino-2-methoxyphenoxy)-1-morpholinoethan-1-one (1.0 eq) in MeCN (0.2 M). Triethylamine (2.0 eq) and HATU (1.0 eq) were then added and the resulting mixture was stirred at room temperature for 2 h. The solution was then poured into water and twice extracted with dichloromethane. Concentration and purification on silica gel (hexane/EtOAc gradient 50%-100%) gave N-(3-methoxy-4-(2-morpholino-2-oxoethoxy)phenyl)-4-(4-methoxyphenyl)thiazole-2-carboxamide. $^1$H-NMR (500 MHz, Acetone-d$_6$) δ 10.04 (s, 1H), 8.10 (s, 1H), 7.99 (d, J=8.8 Hz, 2H), 7.68 (d, J=2.4 Hz, 1H), 7.44 (dd, J=8.7, 2.4 Hz, 1H), 7.06 (d, J=8.7 Hz, 1H), 7.02 (d, J=8.8 Hz, 2H), 4.85 (s, 2H), 3.89 (s, 3H), 3.85 (s, 3H), 3.61 (m, 8H). MS [M+H]: 484.18.

Compounds Prepared Using Scheme 6

General Synthetic Scheme 6

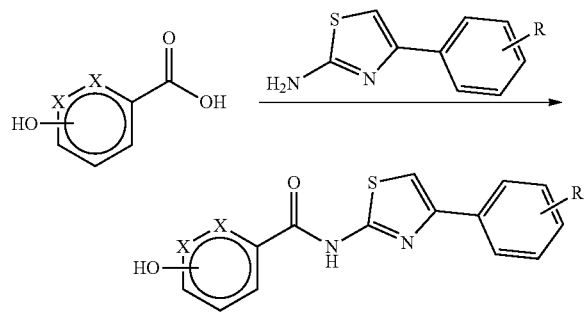

A vial was charged with a phenolic carboxylic acid (1.0 eq) and MeCN (0.15 M). To this solution was then added triethylamine (3.0 eq) and a 4-aryl-2-aminothiazole (1.0 eq). HATU (1.0 eq) was lastly added and the solution was heated at 75° C. until conversion was complete. The solution was quenched with water which caused the precipitation of the product, which was used without further purification.

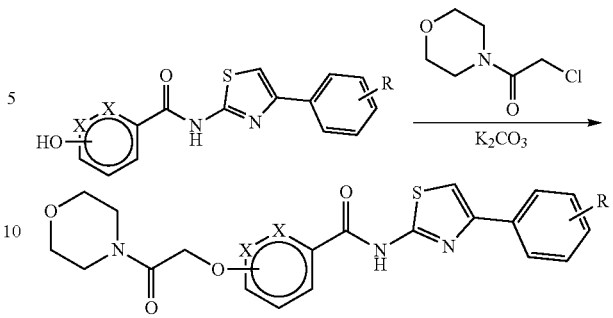

A microwave vial was charged with the above-prepared phenol (1.0 eq) and a 2:1 MeCN:DMF mixture. To this solution was then added 2-chloro-1-morpholinoethan-1-one (1.0 eq) and potassium carbonate (2.0 eq). The vial was then heated at 85° C. until alkylation was complete. The solution was then quenched with water and purified directly on reverse phase preparatory HPLC.

N-(4-(4-methoxyphenyl)thiazol-2-yl)-4-(2-morpholino-2-oxoethoxy)cyclohexane-1-carboxamide (Cpd. 97)

A vial was charged with 4-oxocyclohexane-1-carboxylic acid (1.0 eq) and MeCN (0.15 M) at room temperature. To this solution was then added triethylamine (3.0 eq) and HATU (1.0 eq). 4-(4-methoxyphenyl)thiazol-2-amine (1.0 eq) was lastly added and the solution was warmed to 70° C. for 4 h. The solution was then cooled to room temperature and diluted with water which initiated the precipitation of N-(4-(4-methoxyphenyl)thiazol-2-yl)-4-oxocyclohexane-1-carboxamide. $^1$H-NMR (500 MHz, CDCl$_3$) δ 7.77 (d, J=8.8 Hz, 2H), 7.06 (s, 1H), 6.97 (d, J=8.8 Hz, 2H), 3.85 (s, 3H), 2.59 (m, 1H), 2.47 (m, 2H), 2.25-2.08 (m, 4H), 2.03 (m, 2H). This ketone (1.0 eq) was then dissolved in dichloromethane/methanol (4:1) and treated with sodium borohydride (2.0 eq) at room temperature. After 10 min the reaction was completed and the solution was quenched with HCl (1 N). Dichloromethane was used to extract the solution two times, the combined organic portions were dried over sodium sulfate and concentrated in vacuo to give 4-hydroxy-N-(4-(4-methoxyphenyl)thiazol-2-yl)cyclohexane-1-carboxamide. This material (1.0 eq) was then dissolved in THF (0.1 M) and treated with potassium t-butoxide (1.1 eq) at room temperature. 2-chloro-1-morpholinoethan-1-one (1.1 eq) was then added and the solution was warmed to 60° C. until alkylation was complete. The solution was then poured into aqueous NH$_4$Cl and extracted with EtOAc. The organic portion was washed with brine and dried over sodium sulfate. Concentration in vacuo gave N-(4-(4-methoxyphenyl)thiazol-2-yl)-4-(2-morpholino-2-oxoethoxy)cyclohexane-1-carboxamide as a white solid that was washed twice with hexane and thrice with Et$_2$O to give the clean product. $^1$H-NMR (500 MHz, DMSO-d$_6$) δ 7.82 (d, J=8.3 Hz, 2H), 7.44 (d, J=30.6 Hz, 1H), 6.98 (d, J=8.3 Hz, 2H), 5.27 (s, 1H), 3.79 (d, J=2.0 Hz, 3H), 3.73 (s, 2H), 3.61-3.43 (m, 8H), 2.78-2.57 (m, 1H), 1.93-1.77 (m, 4H), 1.56-1.40 (m, 2H), 1.31-1.03 (m, 2H). MS [M+H]: 460.22

4-(ethylamino)-3-(2-hydroxyethoxy)-N-(4-(4-methoxyphenyl)thiazol-2-yl)benzamide (Cpd. 99)

A vial was charged with 4-oxocyclohexane-1-carboxylic acid (1.0 eq) and MeCN (0.15 M) at room temperature. To this solution was then added triethylamine (3.0 eq) and HATU (1.0 eq). 4-(4-methoxyphenyl)thiazol-2-amine (1.0 eq) was lastly added and the solution was warmed to 70° C. for 4 h. The solution was then cooled to room temperature and diluted with water which initiated the precipitation of N-(4-(4-methoxyphenyl)thiazol-2-yl)-4-oxocyclohexane-1-carboxamide. $^1$H-NMR (500 MHz, CDCl$_3$) δ 7.77 (d, J=8.8 Hz, 2H), 7.06 (s, 1H), 6.97 (d, J=8.8 Hz, 2H), 3.85 (s, 3H), 2.59 (m, 1H), 2.47 (m, 2H), 2.25-2.08 (m, 4H), 2.03 (m, 2H). This ketone (1.0 eq) was then dissolved in dichloromethane/methanol (4:1) and treated with sodium borohydride (2.0 eq) at room temperature. After 10 min the reaction was completed and the solution was quenched with HCl (1 N). Dichloromethane was used to extract the solution two times, the combined organic portions were dried over sodium sulfate and concentrated in vacuo to give 4-hydroxy-N-(4-(4-methoxyphenyl)thiazol-2-yl)cyclohexane-1-carboxamide. This material (1.0 eq) was then dissolved in THF (0.1 M) and treated with potassium t-butoxide (1.1 eq) at room temperature. 2-chloro-1-morpholinoethan-1-one (1.1 eq) was then added and the solution was warmed to 60° C. until alkylation was complete. The solution was then poured into aqueous NH$_4$Cl and extracted with EtOAc. The organic portion was washed with brine and dried over sodium sulfate. Concentration in vacuo gave N-(4-(4-methoxyphenyl)thiazol-2-yl)-4-(2-morpholino-2-oxoethoxy)cyclohexane-1-carboxamide (Cpd. 97) as a white solid that was washed twice with hexane and thrice with Et$_2$O to give the clean product.

A round bottom flask was charged with methyl 3-hydroxy-4-nitrobenzoate (1.0 eq) and 2-(2-bromoethoxy)tetrahydro-2H-pyran (1.5 eq) in DMF (0.4 M). Potassium carbonate (2.0 eq) was then added and the mixture was warmed to 80° C. After 5 h, the solution was diluted with EtOAc and washed four times with water and once with brine.

The solution was then dried over sodium sulfate, concentrated in vacuo, and purified on silica gel (hexane/EtOAc gradient 2%-25%) to give methyl 4-nitro-3-(2-((tetrahydro-2H-pyran-2-yl)oxy)ethoxy)benzoate as a yellow oil. $^1$H-NMR (500 MHz, CDCl$_3$) δ 7.80 (d, J=1.5 Hz, 1H), 7.78 (d, J=8.4 Hz, 1H), 7.66 (dd, J=8.4, 1.5 Hz, 1H), 4.69 (t, J=3.5 Hz, 1H), 4.39-4.28 (m, 2H), 4.07 (ddd, J=11.6, 5.0, 3.9 Hz, 1H), 3.93 (s, 3H), 3.83 (dtt, J=10.1, 7.2, 3.3 Hz, 2H), 3.54-3.47 (m, 1H), 1.78 (m, 1H), 1.69 (m, 1H), 1.56 (m, 2H), 1.53-1.46 (m, 2H). $^{13}$C-NMR (126 MHz, CDCl$_3$) δ 165.13, 151.87, 142.77, 134.70, 125.14, 121.59, 116.19, 99.06, 69.66, 65.30, 62.05, 52.78, 30.39, 25.36, 19.17.

A round bottom flask was charged with Pd/C (10%, 0.05 eq) under an atmosphere of nitrogen. EtOAc (0.25 M) was added, followed by methyl 4-nitro-3-(2-((tetrahydro-2H-pyran-2-yl)oxy)ethoxy)benzoate (1.0 eq). A hydrogen-filled balloon was then affixed to the flask and the airspace was evacuated and backfilled with hydrogen three times. The mixture was vigorously stirred at room temperature for 7 h and then filtered through celite, washing with methanol. Concentration in vacuo gave methyl 4-amino-3-(2-((tetrahydro-2H-pyran-2-yl)oxy)ethoxy)benzoate. $^1$H-NMR (500 MHz, Chloroform-d) δ 7.55 (dd, J=8.2, 1.7 Hz, 1H), 7.50 (d, J=1.8 Hz, 1H), 6.69 (d, J=8.2 Hz, 1H), 4.70 (t, J=3.6 Hz, 1H), 4.23 (t, J=4.8 Hz, 2H), 4.07 (dt, J=11.0, 4.8 Hz, 1H), 3.94-3.79 (m, 5H), 3.58-3.48 (m, 1H), 1.83 (m, 1H), 1.74 (m, 2H), 1.70-1.47 (m, 4H).

This aniline (1.0 eq) was then dissolved in THF/MeOH (2:1) and treated with AcOH (1.0 eq) and acetaldehyde (5.0 eq) at 0° C. NaCNBH$_3$ (1.5 eq) was then added and the solution was warmed to room temperature for 45 min. The solution was partially concentrated in vacuo, diluted with EtOAc and sequentially washed with HCl (1 N), NaHCO$_3$, water, and brine. The organic portion was then dried over sodium sulfate and concentrated in vacuo to give methyl 4-(ethylamino)-3-(2-((tetrahydro-2H-pyran-2-yl)oxy)ethoxy)benzoate as a yellow oil. $^1$H-NMR (500 MHz, Chloroform-d) δ 7.63 (dd, J=8.4, 1.8 Hz, 1H), 7.44 (d, J=1.8 Hz, 1H), 6.52 (d, J=8.3 Hz, 1H), 4.79 (br, 1H), 4.70 (t, J=3.6 Hz, 1H), 4.22 (t, J=4.8 Hz, 2H), 4.07 (dt, J=11.2, 4.6 Hz, 1H), 3.89 (ddd, J=11.2, 8.4, 2.9 Hz, 1H), 3.84 (s, 3H), 3.83-3.76 (m, 1H), 3.57-3.49 (m, 1H), 3.22 (q, J=7.1 Hz, 2H), 1.90-1.79 (m, 1H), 1.79-1.69 (m, 1H), 1.67-1.49 (m, 4H), 1.28 (t, J=7.2 Hz, 3H).

The resulting compound (1.0 eq) was then dissolved in THF/water (2:1) and treated with LiOH (4.0 eq). The resulting mixture was heated to reflux overnight. The solution was then cooled to room temperature, acidified with 10% citric acid and thrice extracted with EtOAc. The combined organic fractions were washed with brine and dried over sodium sulfate. The solution was concentrated to an oil and then precipitated from Et$_2$O/hexanes to give 4-(ethylamino)-3-(2-((tetrahydro-2H-pyran-2-yl)oxy)ethoxy)benzoic acid as a white solid. $^1$H-NMR (500 MHz, Chloroform-d) δ 7.73 (dd, J=8.4, 1.8 Hz, 1H), 7.50 (d, J=1.7 Hz, 1H), 6.56 (d, J=8.4 Hz, 1H), 4.72 (t, J=3.6 Hz, 1H), 4.24 (t, J=4.8 Hz, 2H), 4.08 (dt, J=11.2, 4.6 Hz, 1H), 3.90 (ddd, J=11.2, 8.5, 2.9 Hz, 1H), 3.84 (dt, J=11.2, 4.8 Hz, 1H), 3.59-3.52 (m, 1H), 3.25 (q, J=7.2 Hz, 2H), 1.85 (tdd, J=11.9, 7.1, 3.2 Hz, 1H), 1.75 (ddt, J=13.1, 9.6, 3.4 Hz, 1H), 1.70-1.50 (m, 4H), 1.30 (t, J=7.2 Hz, 3H).

A vial was charged with 4-(ethylamino)-3-(2-((tetrahydro-2H-pyran-2-yl)oxy)ethoxy)benzoic acid (1.0 eq) and DMF (0.1 M) at room temperature. To this solution was added triethylamine (2.0 eq) and 4-(4-methoxyphenyl)thiazol-2-amine (1.0 eq). Lastly, HATU (1.1 eq) was added and the solution was warmed to 85° C. The solution was poured into water and twice extracted with EtOAc. The solution was then dried over sodium sulfate, concentrated in vacuo and purified on reverse phase preparatory HPLC to 4-(ethylamino)-N-(4-(4-methoxyphenyl)thiazol-2-yl)-3-(2-((tetrahydro-2H-pyran-2-yl)oxy)ethoxy)benzamide. $^1$H-NMR (400 MHz, Chloroform-d) δ 7.73 (dd, J=8.6, 1.5 Hz, 2H), 7.63-7.58 (m, 1H), 7.53 (d, J=1.8 Hz, 1H), 6.99-6.94 (m, 3H), 6.60 (d, J=8.4 Hz, 1H), 4.71 (d, J=3.6 Hz, 1H), 4.28 (t, J=4.8 Hz, 2H), 4.10 (dt, J=9.9, 4.6 Hz, 1H), 3.98-3.80 (m, 6H), 3.60-3.50 (m, 1H), 3.26 (q, J=7.1 Hz, 2H), 1.91-1.71 (m, 2H), 1.69-1.50 (m, 4H), 1.31 (td, J=7.2, 1.4 Hz, 3H).

This material (1.0 eq) was dissolved in THF/1N HCl (3:1) and warmed to 65° C. for 30 min. The solution was then poured into NaHCO$_3$ and twice extracted with dichloromethane. The solution was concentrated and purified on reverse phase preparatory HPLC to give 4-(ethylamino)-3-(2-hydroxyethoxy)-N-(4-(4-methoxyphenyl)thiazol-2-yl)benzamide (Cpd. 99). $^1$H-NMR (500 MHz, Chloroform-d) δ 7.73 (d, J=8.6 Hz, 2H), 7.55 (dd, J=8.3, 1.9 Hz, 1H), 7.46 (d, J=1.9 Hz, 1H), 7.00-6.93 (m, 3H), 6.59 (d, J=8.3 Hz, 1H), 4.24 (t, J=4.5 Hz, 2H), 4.05 (t, J=4.5 Hz, 2H), 3.85 (s, 3H), 3.24 (q, J=7.2 Hz, 2H), 1.28 (t, J=7.2 Hz, 3H). $^{13}$C-NMR (126 MHz, CDCl3) δ 164.41, 159.72, 159.67, 148.77, 144.92, 142.94, 127.45, 126.64, 122.47, 118.05, 114.22, 110.15, 108.22, 105.96, 70.15, 61.29, 55.36, 37.62, 14.52. MS [M+H]: 414.23

3-methoxy-4-(2-morpholino-2-oxoethoxy)-N-(5-(3-(trifluoromethyl)benzyl)thiazol-2-yl)benzamide (Cpd. 100)

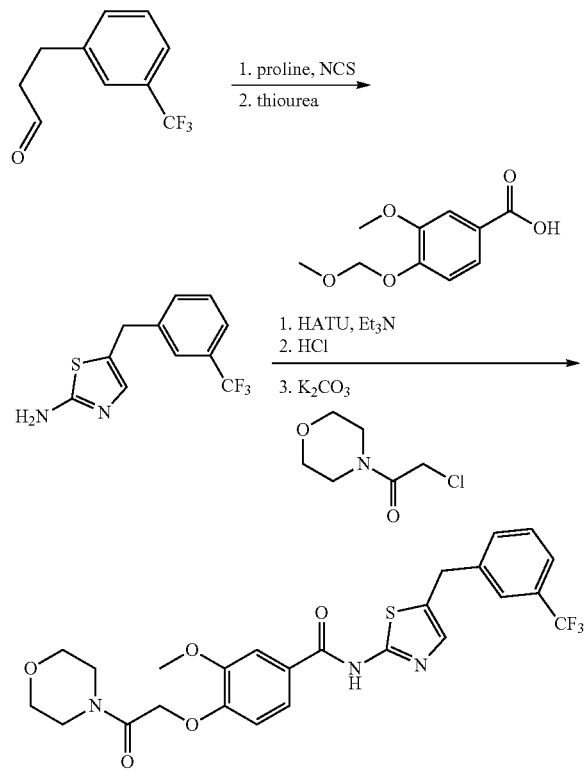

A round bottom flask was charged with 3-(3-(trifluoromethyl)phenyl)propanal (1.0 eq) and dichloromethane (0.5 M) and then cooled to 0° C. To this solution was then added L-proline (0.2 eq) and N-chlorosuccinimide (1.3 eq). The resulting solution was then stirred at room temperature for 1.5 h. The solution was then diluted with hexane, stirred vigorously and filtered. The filtrate was diluted with EtOAc and sequentially washed with NaHCO$_3$ and brine. The solution wad dried over sodium sulfate and concentrated in vacuo to give a yellow oil that was then dissolved in ethanol (0.3 M). Thiourea (1.0 eq) was then added and the solution was heated to reflux until the reaction was complete. It was then cooled to room temperature, concentrated in vacuo, and partitioned between EtOAc and aqueous NaHCO$_3$. The solution was then concentrated and purified on silica gel to give 5-(3-(trifluoromethyl)benzyl)thiazol-2-amine as a beige solid. $^1$H-NMR (500 MHz, CDCl$_3$) δ 7.50 (d, J=7.4 Hz, 1H), 7.47 (s, 1H), 7.46-7.38 (m, 2H), 6.82 (d, J=1.2 Hz, 1H), 4.02 (s, 2H). This aminothiazole (1.0 eq) was dissolved in DMF (0.1 M) and treated with triethylamine (2.0 eq) and 3-methoxy-4-(methoxymethoxy)benzoic acid (1.0 eq). Lastly, HATU (1.1 eq) was added and the solution was warmed to 70° C. overnight. Upon completion, the solution was diluted with water and purified directly on reverse phase preparatory HPLC to give 3-methoxy-4-(methoxymethoxy)-N-(5-(3-(trifluoromethyl)benzyl)thiazol-2-yl)benzamide. $^1$H-NMR (500 MHz, CDCl$_3$) δ 7.58 (d, J=1.9 Hz, 1H), 7.54-7.48 (m, 3H), 7.47-7.42 (m, 2H), 7.22 (d, J=8.4 Hz, 1H), 7.03 (s, 1H), 5.30 (s, 2H), 4.14 (s, 2H), 3.92 (s, 3H), 3.52 (s, 3H). The acetal was removed by dissolving the compound (1.0 eq) in THF/1N HCl (4:1) and stirring at 45° C. until the reaction was complete. The solution was then poured into aqueous NaHCO$_3$ and thrice extracted with dichloromethane. The combined organic portions were dried over sodium sulfate and concentrated to a brown solid. $^1$H-NMR (500 MHz, Chloroform-d) δ 7.54 (d, J=7.5 Hz, 2H), 7.50 (d, J=7.4 Hz, 1H), 7.48-7.39 (m, 3H), 6.92 (d, J=8.1 Hz, 1H), 6.81 (s, 1H), 4.09 (s, 2H), 3.86 (s, 3H). The 4-hydroxy-3-methoxy-N-(5-(3-(trifluoromethyl)benzyl)thiazol-2-yl)benzamide (1.0 eq) was then transferred to a microwave tube and dissolved in MeCN (0.1 M). 2-chloro-1-morpholinoethan-1-one (1.05 eq), potassium carbonate (2.0 eq), and a catalytic amount of KI were then added and the mixture was warmed to 85° C. for 60 min. The inorganic salts were removed via filtration and the filtrate was purified via reverse phase preparatory HPLC to give 3-methoxy-4-(2-morpholino-2-oxoethoxy)-N-(5-(3-(trifluoromethyl)benzyl)thiazol-2-yl)benzamide as a white solid. $^1$H-NMR (500 MHz, DMSO-d$_6$) δ 7.71-7.57 (m, 6H), 7.21 (s, 1H), 6.81 (d, J=8.0 Hz, 1H), 5.20 (s, 2H), 4.14 (s, 2H), 3.82 (s, 3H), 3.67 (br, 2H), 3.62 (br, 2H), 3.58 (br, 2H), 3.46 (br, 2H). MS [M+H]: 536.27

Ethyl 6-(5-((4-(2-chloro-4-methoxyphenyl)thiazol-2-yl)carbamoyl)-2-(2-morpholino-2-oxoethoxy) phenoxy)hexanoate (Cpd. 101)

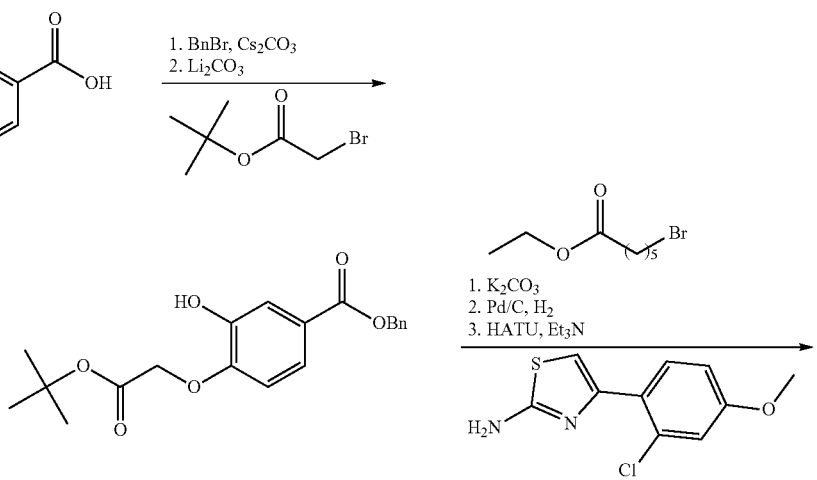

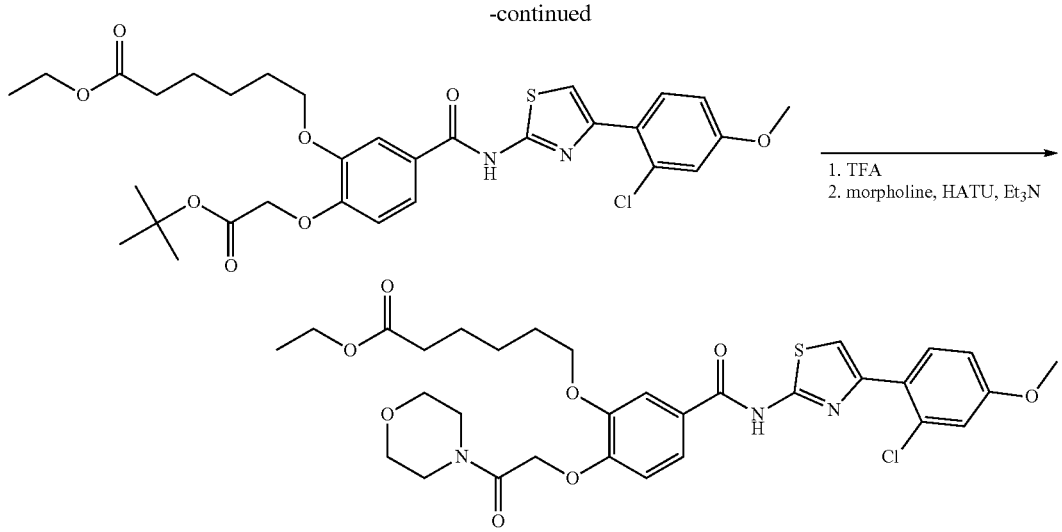

A vial was charged with 3,4-dihydroxybenzoic acid (1.0 eq) and aqueous methanol (9:1 MeOH:H₂O). To this solution was then added cesium carbonate (0.5 eq), gas evolution was noted. After 2.5 h, the solution was concentrated in vacuo, then azeotroped with toluene to further dry. The resulting solid was suspended in DMF (0.15 M) and cooled to 0° C. at which time benzyl bromide (1.0 eq) was added and stirred for 18 h. The solution was then diluted with EtOAc and sequentially washed with water, NaHCO₃, and brine. The solution was then dried over sodium sulfate and concentrated in vacuo. Purification on silica gel (hexane/EtOAc gradient 2%-50%) gave benzyl 3,4-dihydroxybenzoate (31% yield). ¹H-NMR (500 MHz, Chloroform-d) δ 7.66-7.59 (m, 2H), 7.43 (d, J=7.1 Hz, 2H), 7.39 (t, J=7.3 Hz, 2H), 7.35 (d, J=7.2 Hz, 1H), 6.91 (d, J=8.3 Hz, 1H), 5.63 (s, 1H), 5.32 (s, 2H), 5.25 (s, 1H).

A vial was charged with benzyl 3,4-dihydroxybenzoate (1.0 eq), Li₂CO₃ (1.0 eq) and DMF (0.4 M) and warmed to 50° C. tert-butyl 2-bromoacetate (1.0 eq) was then slowly added dropwise and stirred for 22 h. The solution was then cooled to room temperature, diluted with water and extracted with EtOAc. Concentration and purification on silica gel (hexane/EtOAc gradient 2%-50%) gave benzyl 4-(2-(tert-butoxy)-2-oxoethoxy)-3-hydroxybenzoate. ¹H-NMR (500 MHz, Chloroform-d) δ 7.68 (d, J=2.0 Hz, 1H), 7.62-7.59 (m, 1H), 7.46-7.42 (m, 2H), 7.38 (t, J=7.4 Hz, 2H), 7.36-7.30 (m, 1H), 6.88 (s, 1H), 6.86 (d, J=8.5 Hz, 1H), 5.33 (s, 2H), 4.59 (s, 2H), 1.48 (s, 9H).

Potassium carbonate (2.0 eq) was added to a solution of benzyl 4-(2-(tert-butoxy)-2-oxoethoxy)-3-hydroxybenzoate (1.0 eq) and ethyl 6-bromohexanoate (1.2 eq) in DMF (0.25 M). The mixture was then heated at 80° C. for 2 h, then at 60° C. overnight. The reaction was then partitioned between water and EtOAc and the organic portion was dried over sodium sulfate and concentrated in vacuo. Purification on silica gel (hexane/EtOAc gradient 2%-40%) gave benzyl 4-(2-(tert-butoxy)-2-oxoethoxy)-3-((6-ethoxy-6-oxohexyl)oxy)benzoate (29% yield). ¹H-NMR (400 MHz, Chloroform-d) δ 7.65 (dd, J=8.4, 2.0 Hz, 1H), 7.59 (d, J=2.0 Hz, 1H), 7.46-7.41 (m, 2H), 7.41-7.33 (m, 3H), 6.77 (d, J=8.5 Hz, 1H), 5.34 (s, 2H), 4.62 (s, 2H), 4.13 (q, J=7.1 Hz, 2H), 4.06 (t, J=6.7 Hz, 2H), 2.33 (t, J=7.5 Hz, 2H), 1.87 (dt, J=14.3, 6.8 Hz, 2H), 1.71 (p, J=7.5 Hz, 2H), 1.51 (m, 2H), 1.47 (s, 9H), 1.25 (t, J=7.1 Hz, 3H).

A vial was charged with benzyl 4-(2-(tert-butoxy)-2-oxoethoxy)-3-((6-ethoxy-6-oxohexyl)oxy)benzoate (1.0 eq) and EtOAc (0.1 M) under a nitrogen atmosphere. To this solution was then added Pd/C (10%, 0.1 eq) and a hydrogen-filled balloon was affixed to the reaction vessel. The mixture was vigorously stirred for 18 h, and then filtered through celite (washing with MeOH) and concentrated to give 4-(2-(tert-butoxy)-2-oxoethoxy)-3-((6-ethoxy-6-oxohexyl)oxy) benzoic acid. ¹H-NMR (400 MHz, Chloroform-d) δ 7.67 (dd, J=8.5, 2.0 Hz, 1H), 7.58 (d, J=1.9 Hz, 1H), 6.79 (d, J=8.5 Hz, 1H), 4.64 (s, 2H), 4.13 (q, J=7.1 Hz, 2H), 4.08 (t, J=6.7 Hz, 2H), 2.34 (t, J=7.5 Hz, 2H), 1.89 (dt, J=14.4, 6.8 Hz, 2H), 1.80-1.66 (m, 2H), 1.48 (s, 9H), 1.26 (t, J=7.1 Hz, 3H) two protons under solvent peaks.

A reaction vial was charged with 4-(2-(tert-butoxy)-2-oxoethoxy)-3-((6-ethoxy-6-oxohexyl)oxy)benzoic acid (1.0 eq) and triethylamine (2.0 eq) in MeCN. To this solution was then added 4-(2-chloro-4-methoxyphenyl)thiazol-2-amine (1.0 eq) followed by HATU (1.0 eq). The solution was warmed to 75° C. until the reaction was complete. The solution was then diluted with EtOAc and thrice washed with water. Concentration and purification on silica gel (hexane/EtOAc 5%-50% gradient) gave ethyl 6-(2-(2-(tert-butoxy)-2-oxoethoxy)-5-((4-(2-chloro-4-methoxyphenyl) thiazol-2-yl)carbamoyl)phenoxy)hexanoate. This product was then dissolved in CH₂Cl₂/TFA (4:1) and stirred at room temperature overnight. Concentration in vacuo gave 2-(4-((4-(2-chloro-4-methoxyphenyl)thiazol-2-yl)carbamoyl)-2-((6-ethoxy-6-oxohexyl)oxy)phenoxy)acetic acid which was used without further purification.

A flask was charged with 2-(4-((4-(2-chloro-4-methoxyphenyl)thiazol-2-yl)carbamoyl)-2-((6-ethoxy-6-oxohexyl)oxy)phenoxy)acetic acid (1.0 eq) and DMF (0.25 M) at room temperature. To this solution was then added triethylamine (2.0 eq) and morpholine (4.0 eq). Lastly, HATU (2.0 eq) was added and stirred for 1 h. The solution was then diluted with EtOAc and twice washed with water. Concentration gave a white solid which was purified on silica gel (hexane/EtOAc gradient 15%-100%) to give ethyl 6-(5-((4-(2-chloro-4-methoxyphenyl)thiazol-2-yl)carbamoyl)-2-(2-morpholino-2-oxoethoxy)phenoxy)hexanoate. ¹H-NMR (500 MHz, DMSO-d₆) δ 12.61 (s, 1H), 7.85 (d, J=8.7 Hz, 1H), 7.77 (d, J=2.1 Hz, 1H), 7.71 (dd, J=8.5, 2.1 Hz, 1H), 7.53 (s, 1H), 7.13 (d, J=2.7 Hz, 1H), 7.03 (dd, J=8.7, 2.6 Hz, 1H), 7.00 (d, J=8.6 Hz, 1H), 4.96 (s, 2H), 4.13-4.01 (m, 4H), 3.82 (s, 3H), 3.62 (br, 2H), 3.57 (br, 2H), 3.51-3.43 (m, 4H), 2.69 (s, 1H), 2.33 (t, J=7.4 Hz, 2H), 1.77 (p, J=6.8 Hz, 2H), 1.62 (p, J=7.5 Hz, 2H), 1.46 (p, J=7.6, 7.2 Hz, 2H), 1.17 (t, J=7.1 Hz, 3H). MS [M+H]: 646.33

N-(4-(2-chloro-4-methoxyphenyl)thiazol-2-yl)-4-(2-morpholino-2-oxoethoxy)-3-(5-(1-(25-oxo-29-((3aR,4S,6aS)-2-oxohexahydro-1H-thieno[3,4-d]imidazol-4-yl)-3,6,9,12,15,18,21-heptaoxa-24-azanonacosyl)-1H-1,2,3-triazol-4-yl)pentanamido)benzamide (Cpd. 103)

N-(4-(2-chloro-4-methoxyphenyl)thiazol-2-yl)-3-(hept-6-ynamido)-4-(2-morpholino-2-oxoethoxy)benzamide (10 mg, 16.4 µmol) was weighed into a 4 mL vial. Biotin-PEG$_7$-azide was added as a solution in acetonitrile (0.12 mL, 100 mg/mL, 16.4 µmol) followed by Hunig's base (14.3 µL, 82 µmol) and CuI as a solution in acetonitrile (0.1 mL, 6 mg/mL, 3.3 µmol). The reaction was stirred at 23° C. for 18 h. The crude product was purified by RP-HPLC and after evaporation of the combined fractions yielded the product (13 mg, 65%) as a white foamy solid. $^1$HNMR (500 MHz, Methanol-d$_4$) δ 8.66 (d, J=2.3 Hz, 1H), 8.49 (s, 1H), 7.93 (s, 1H), 7.85 (d, J=8.7 Hz, 1H), 7.81 (s, 1H), 7.78 (dd, J=8.6, 2.3 Hz, 1H), 7.45 (s, 1H), 7.17 (d, J=8.7 Hz, 1H), 7.03 (d, J=2.6 Hz, 1H), 6.93 (dd, J=8.7, 2.6 Hz, 1H), 5.01 (s, 2H), 4.52 (t, J=5.0 Hz, 2H), 4.45 (dd, J=7.9, 4.8 Hz, 1H), 4.26 (dd, J=7.9, 4.4 Hz, 1H), 3.84 (t, J=5.1 Hz, 2H), 3.83 (s, 3H), 3.73-3.65 (m, 4H), 3.64-3.60 (m, 3H), 3.59-3.47 (m, 28H), 3.35-3.31 (m, 2H), 3.15 (ddd, J=9.0, 5.9, 4.5 Hz, 1H), 2.88 (dd, J=12.7, 5.0 Hz, 1H), 2.79-2.72 (m, 2H), 2.67 (d, J=12.7 Hz, 1H), 2.57-2.5 (m, 2H), 2.18 (t, J=7.4 Hz, 2H), 1.83-1.73 (m, 4H), 1.72-1.50 (m, 3H), 1.44-1.35 (m, 2H), 1.17 (t, J=7.0 Hz, 1H); LRMS (ESI+ve): calculated for C$_{56}$H$_{70}$ClN$_{10}$O$_{15}$S$_2$ [M+H]=1231.49, observed [M+H]=1231.8.

The Effect of SBI-477 Analogs on TAG Accumulation

Exemplary SBI-477 analogs disclosed above as compounds were tested for their effect on TAG accumulation in primary murine skeletal myocytes as previously described. The following compounds showed activity on triacylglyceride (TAG) accumulation in primary murine skeletal myocytes. Activity Score (IC$_{50}$): A, <1 µM; B, 1 µM-10 µM; C, >10 µM Formula 10

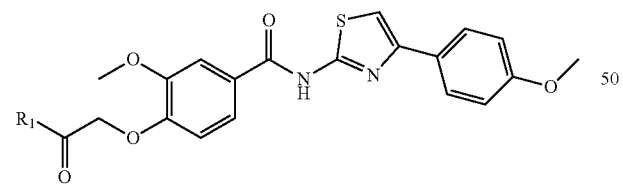

TABLE 4

Compounds based on Formula 10.

| Entry | R1 | Activity | Cmpd # |
|---|---|---|---|
| 1 | morpholine (N-linked) | A | 7 |
| 2 | piperidine (N-linked) | B | 8 |
| 3 | 4-methylpiperazine (N-linked) | A | 9 |
| 4 | thiomorpholine (N-linked) | A | 11 |
| 5 | 4-oxopiperidine (N-linked) | B | 12 |
| 6 | 4-(methylsulfonyl)piperazine (N-linked) | C | 13 |
| 7 | 2-(piperidin-1-yl)ethylamino | B | 14 |
| 8 | 2-(dimethylamino)ethyl(ethyl)amino | C | 15 |
| 9 | methyl glycinate (N-linked) | C | 16 |
| 10 | H$_2$N– | B | 17 |
| 11 | methylamino | A | 18 |
| 12 | dimethylamino | B | 19 |

TABLE 4-continued

Compounds based on Formula 10.

| Entry | R1 | Activity | Cmpd # |
|---|---|---|---|
| 13 | methoxyethylamino | B | 20 |
| 14 | methoxypropylamino | B | 21 |
| 15 | cyclopropylmethylamino | B | 10 |
| 16 | cyclobutylamino | A | 22 |
| 17 | benzylamino | B | 23 |
| 18 | pyridin-2-ylmethylamino | C | 24 |

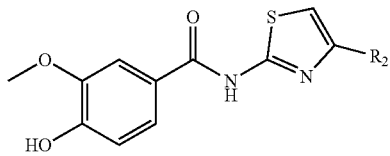

Formula 12

TABLE 5

Activity of compounds based on Formula 12.

| Entry | R₂ | Activity | Cpd. # |
|---|---|---|---|
| 1 | 4-methoxyphenyl | C | 1 |
| 2 | phenyl | C | 2 |
| 3 | 4-methylphenyl | C | 3 |
| 4 | 4-chlorophenyl | B | 4 |
| 5 | 3,4-dichlorophenyl | B | 5 |
| 6 | 4-cyanophenyl | B | 6 |

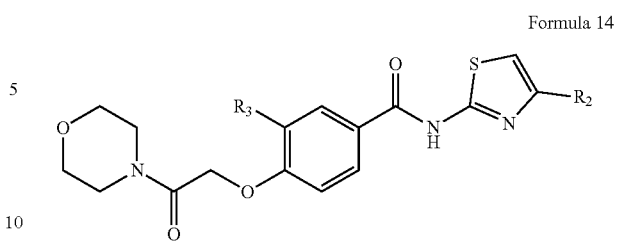

Formula 14

TABLE 6

Activity of compounds based on Formula 14.

| Entry | R₂ | R₃ | Activity | Cpd. # |
|---|---|---|---|---|
| 2 | Ph | —OMe | A | 25 |
| 3 | 4-Me Ph | —OMe | A | 30 |
| 4 | 4-Cl Ph | —OMe | A | 31 |
| 5 | 3,4-Cl Ph | —OMe | A | 37 |
| 6 | 4-CN Ph | —OMe | A | 32 |
| 7 | 3,4-OMe Ph | —OMe | B | 38 |
| 8 | 3-OMe Ph | —OMe | B | 35 |
| 9 | 2,4-OMe Ph | —OMe | A | 36 |
| 10 | 3,4-dioxolane Ph | —OMe | B | 39 |
| 11 | 4-OCF₃ Ph | —OMe | A | 26 |
| 12 | 4-NO₂ Ph | —OMe | A | 33 |
| 13 | 4-pyrrolidine Ph | —OMe | A | 34 |
| 14 | 4-OH Ph | —OMe | A | 27 |
| 15 | 4-OEt Ph | —OMe | A | 28 |
| 16 | 4-O—iPr Ph | —OMe | A | 29 |
| 17 | 4-OMe Ph | —H | A | 41 |
| 18 | 2-Me Ph | —H | A | 47 |
| 19 | 2-Cl Ph | —H | A | 48 |
| 20 | 2-F Ph | —H | A | 49 |
| 21 | 2-OMe Ph | —H | A | 50 |
| 22 | 3-Me Ph | —H | A | 51 |
| 23 | 3-Cl Ph | —H | A | 52 |
| 24 | 3-F Ph | —H | A | 53 |
| 25 | 2-Cl, 4-OiPr Ph | —H | A | 55 |
| 26 | 2-C-, 4-OMe Ph | —H | A | 54 |
| 27 | 2-F, 4-OMe Ph | —H | A | 56 |
| 28 | 4-Et Ph | —H | A | 44 |
| 29 | 4-iPr Ph | —H | A | 45 |
| 30 | 4-OCHF₂ Ph | —H | A | 40 |
| 31 | 4-F Ph | —H | A | 46 |
| 32 | 4-OCH₂CH₂OMe | —H | A | 43 |

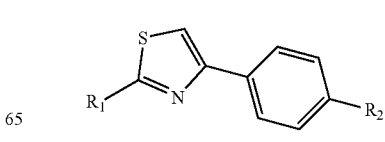

Formula 16

TABLE 7

Activity of compounds based on Formula 16.

| Entry | R₁ | R₂ | Activity | Cpd. # |
|---|---|---|---|---|
| 1 | morpholine-C(O)-CH₂-O-(3-phenyl)-C(O)NH- | 4-OMe | B | 94 |
| 2 | morpholine-C(O)-CH₂-O-(3-phenyl)-C(O)NH- | H | B | 95 |
| 3 | morpholine-C(O)-CH₂-O-(3-phenyl)-C(O)NH- | 3-OMe | B | 96 |
| 4 | morpholine-CH₂-C(O)-O-(pyridin-5-yl)-2-C(O)NH- | 4-OMe | C | 92 |
| 5 | morpholine-CH₂-C(O)-O-(pyridin-2-yl)-5-C(O)NH- | 4-OMe | C | 93 |
| 6 | morpholine-CH₂CH₂-O-(3-OMe-4-phenyl)-C(O)NH- | 4-OMe | B | 90 |
| 7 | morpholine-C(O)-CH₂-O-(3-OMe-4-phenyl)-CH₂-NH- | 4-OMe | B | 89 |
| 8 | morpholine-C(O)-CH₂-O-(3-OMe-4-phenyl)-NH-C(O)- | 4-OMe | C | 91 |

TABLE 7-continued

Activity of compounds based on Formula 16.

| Entry | R₁ | R₂ | Activity | Cpd. # |
|---|---|---|---|---|
| 9 | morpholine-C(O)-CH₂CH₂-C(O)NH- | 4-OMe | B | 82 |
| 10 | 3,4-dihydro-2H-benzo[b][1,4]oxazine-N-C(O)-CH₂CH₂-C(O)NH- | 4-OMe | A | 81 |
| 11 | 4-amino-3-methoxybenzamide | 4-OMe | B | 77 |
| 12 | 4-ethylamino-3-(2-hydroxyethoxy)benzamide | 4-OMe | B | 99 |
| 13 | 4-(2-morpholino-2-oxoethoxy)cyclohexane-1-carboxamide | 4-OMe | C | 97 |

Formula 18

(morpholine-C(O)-CH₂-O)-(3-OMe)-benzamide-NHR

TABLE 8

Activity of compounds based on Formula 18.

| Entry | R | Activity | Cpd. # |
|---|---|---|---|
| 1 | benzothiazol-2-yl | C | 87 |
| 2 | 6-methoxybenzothiazol-2-yl | B | 88 |
| 3 | biphenyl-3-yl | C | 83 |

TABLE 8-continued

Activity of compounds based on Formula 18.

| Entry | R | Activity | Cpd. # |
|---|---|---|---|
| 4 | (5-phenyl-thiazol-2-yl) | C | 79 |
| 5 | (5-(4-methoxyphenyl)-thiazol-2-yl) | C | 80 |
| 6 | (4-benzyl-thiazol-2-yl) | B | 85 |
| 7 | (4-benzyl-5-phenyl-thiazol-2-yl) | A | 84 |
| 8 | (5-(3-trifluoromethylbenzyl)-thiazol-2-yl) | C | 100 |
| 9 | (5-(4-methoxybenzyl)-thiazol-2-yl) | B | 98 |

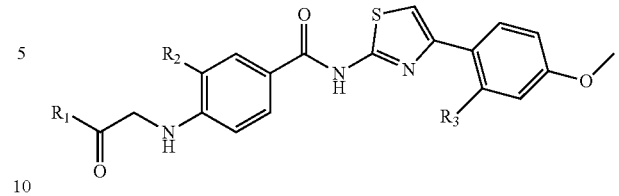

Formula 20

TABLE 9

Activity of compounds based on Formula 20.

| Entry | R$_1$ | R$_2$ | R$_3$ | Activity | Cpd. # |
|---|---|---|---|---|---|
| 1 | morpholine | —OMe | —H | A | 75 |
| 2 | morpholine | —H | —H | A | 66 |
| 3 | —NHMe | —H | —H | A | 67 |
| 4 | —NMe$_2$ | —H | —H | A | 68 |
| 5 | —NHCH$_2$CH$_2$OMe | —H | —H | C | 69 |
| 6 | morpholine | —H | —Cl | A | 70 |
| 7 | —NHMe | —H | —Cl | A | 71 |
| 8 | —NMe$_2$ | —H | —Cl | A | 72 |
| 9 | —NHCH$_2$CH$_2$OMe | —H | —Cl | A | 73 |

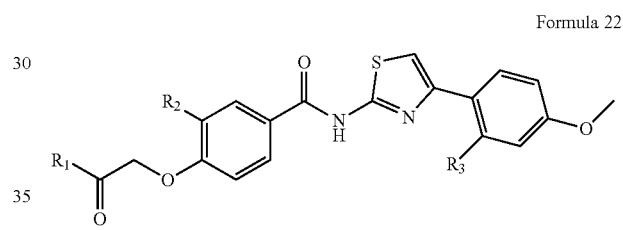

Formula 22

TABLE 10

Activity of compounds based on Formula 22.

| Entry | R$_1$ | R$_2$ | R$_3$ | Activity | Cpd. # |
|---|---|---|---|---|---|
| 5 | —NHMe | —H | —Cl | A | 58 |
| 6 | —NMe$_2$ | —H | —Cl | A | 60 |
| 7 | —NHEt | —H | —Cl | A | 59 |
| 8 | —NH$_2$ | —H | —Cl | B | 57 |

It is understood that the disclosed method and compositions are not limited to the particular methodology, protocols, and reagents described as these may vary. It is also to be understood that the terminology used herein is for the purpose of describing particular forms and embodiments only, and is not intended to limit the scope of the present invention which will be limited only by the appended claims.

"Optional" or "optionally" means that the subsequently described event, circumstance, or material may or may not occur or be present, and that the description includes instances where the event, circumstance, or material occurs or is present and instances where it does not occur or is not present.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific forms and embodiments of the method and compositions described herein. Such equivalents are intended to be encompassed by the following claims.

We claim:
1. A compound represented by the general Formula II:

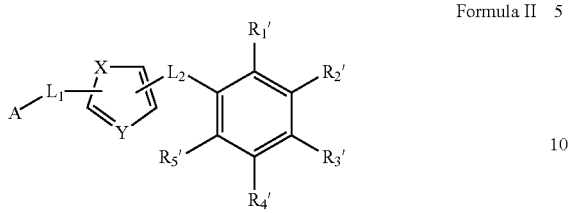

Formula II wherein A is

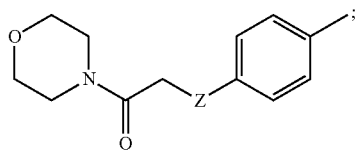

Z is O or —NH—;
L1 is —C(O)NR'—, —NR'C(O)—, —C(O)O—, —OC(O)—, —O—, a bond, substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;
L2 is —C(O)NR'—, —NR'C(O)—, —C(O)O—, —OC(O)—, —O—, absent, a bond, substituted alkyl, unsubstituted alkyl, substituted alkylene, unsubstituted alkylene, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio;
$R_1'$, $R_2'$, $R_3'$, $R_4'$ and $R_5'$ are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, or cyano, or any two adjacent $R_1'$, $R_2'$, $R_3'$, $R_4'$ and $R_5'$ fuse to form substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, or unsubstituted heterocyclyl, and
X and Y are, as valence permits, independently C, O, N, S, $CR_6'R_7'$, or $NR_8'$,
wherein $R_6'$, $R_7'$, and $R_8'$ are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio.

2. The compound of claim 1, wherein the compound of Formula II is represented by the general Formula IV:

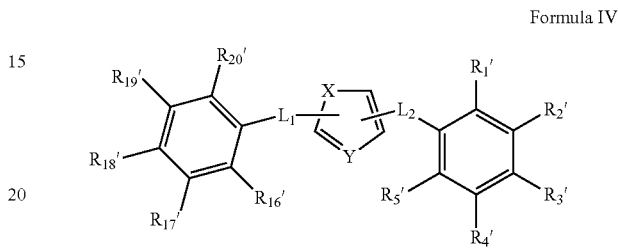

Formula IV wherein $R_{16}'$, $R_{17}'$, $R_{19}'$, and $R_{20}'$, are independently hydrogen, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, or cyano,
$R_{18}'$ is

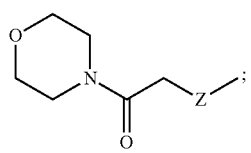

and
Z is —O— or —NH—.

3. The compound of claim 2, wherein the compound of Formula IV is represented by the general Formula VIII:

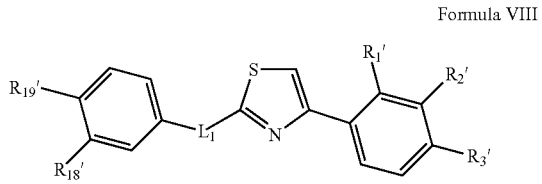

Formula VIII wherein
$L_1$ is —NR'C(O)—, —C(O)NR'—, or substituted amino,
$R_{19}'$ are independently hydrogen, substituted alkoxy, unsubstituted alkoxy, substituted amino, or unsubstituted amino, R$_{18}$' is

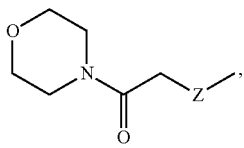

and

Z is —O— or —NH—.

4. The compound of claim 1, wherein the compound of Formula II is represented by the general Formula IX:

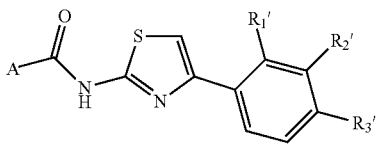

Formula IX wherein

R$_1$', R$_2$' and R$_3$' are independently hydrogen, substituted heterocyclyl, unsubstituted heterocyclyl, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, amide, substituted amide, carbonyl, substituted carbonyl, carboxyl, substituted carboxyl, substituted alkylthio, unsubstituted alkylthio, halogen (F, Cl, Br, I), hydroxyl, nitro, cyano, R$_1$' and R$_2$', or R$_2$' and R$_3$' combine to form substituted heterocyclyl or unsubstituted heterocyclyl, A is

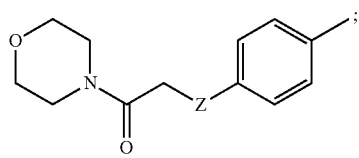

and

Z is O or —NH—.

5. The compound of claim 1, wherein the compound is not SBI-993.

6. A compound represented by the Formula:

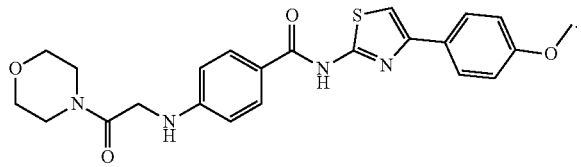 [SMILES: COc1ccc(-c2csc(NC(=O)c3ccc(NCC(=O)N4CCOCC4)cc3)n2)cc1]

7. The compound of claim 1 in a pharmaceutical carrier, said carrier further comprising a Mondo inhibitor.

* * * * *

```
                        SEQUENCE LISTING

<160> NUMBER OF SEQ ID NOS: 70

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
gtcaatcttg agggctaggt ct                                                22

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
ctggttcagc tccagaggtt                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
caggtgggcc tatgagatgt                                                   20

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
ggacgtaatg atccgccatc tt                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic Primer

<400> SEQUENCE: 5
agtttcctgc atgttcattc ct                                                22

<210> SEQ ID NO 6
<211> LENGTH: 22
```

<212> TYPE: DNA
<213> ORGANISM: Artificial Sequence
<220> FEATURE:
<223> OTHER INFORMATION: Synthetic Primer

<400> SEQUENCE: 6
ccacaattcg ggaacatgta tt                                    22

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gtggcttcag caactaccgt                                       20

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
caggaacaga gaaaccacct g                                     21

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
gctctacttc acttggctgg t                                     21

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
cagcaggttg tgtgtcttca c                                     21

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
gcagtcagtt tgtgaccagg                                       20

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
atcagcttct gcttcctcag a                                              21

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
gatgcctcct tcttcggagt                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cctcggagtg aatctgggtt                                                20

<210> SEQ ID NO 15
<211> LENGTH: 22
<212> TYPE: DNA
<213> ORGANISM: Artificial Sequence
<220> FEATURE:
<223> OTHER INFORMATION: Synthetic Primer

<400> SEQUENCE: 15
tcaagagcga gatgtgcata ag                                             22

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
catcagggtt taattcagca g                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
gctcaccaag ctcttcgagt                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
gccggatctt gtctctccac                                                20

<210> SEQ ID NO 19
<211> LENGTH: 23
<212> TYPE: DNA
<213> ORGANISM: Artificial Sequence

```
<220> FEATURE:
<223> OTHER INFORMATION: Synthetic Primer

<400> SEQUENCE: 19
gtgtctccca agtggaagaa ttt                                              23

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
gctcttcctc cgcttcacat                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
cttctctcac gtgggttggc                                                  20

<210> SEQ ID NO 22
<211> LENGTH: 21
<212> TYPE: DNA
<213> ORGANISM: Artificial Sequence
<220> FEATURE:
<223> OTHER INFORMATION: Synthetic Primer

<400> SEQUENCE: 22
atcagcaagc caggtttgta g                                                21

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
agtttcctgc atgttcattc ct                                               22

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
ccacaattcg ggaacatgta tt                                               22

<210> SEQ ID NO 25
<211> LENGTH: 23
<212> TYPE: DNA
<213> ORGANISM: Artificial Sequence
<220> FEATURE:
<223> OTHER INFORMATION: Synthetic Primer

<400> SEQUENCE: 25
tctacaaccc tgaagtgctt gat                                              23
```

```
<210> SEQ ID NO 26
<211> LENGTH: 22
<212> TYPE: DNA
<213> ORGANISM: Artificial Sequence
<220> FEATURE:
<223> OTHER INFORMATION: Synthetic Primer

<400> SEQUENCE: 26
atagaatggg gtactgatgc aa                                                  22

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
ggccagtgct atgctgagat                                                     20

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
atcacacagc cagggtcaag                                                     20

<210> SEQ ID NO 29
<211> LENGTH: 21
<212> TYPE: DNA
<213> ORGANISM: Artificial Sequence
<220> FEATURE:
<223> OTHER INFORMATION: Synthetic Primer

<400> SEQUENCE: 29
cgctcaccaa cagtaaggtg g                                                   21

<210> SEQ ID NO 30
<211> LENGTH: 19
<212> TYPE: DNA
<213> ORGANISM: Artificial Sequence
<220> FEATURE:
<223> OTHER INFORMATION: Synthetic Primer

<400> SEQUENCE: 30
gcttggcagg gagttcctc                                                      19

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
gtgcacaagt ggtgcatcag                                                     20

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 32
cagtgggatc tgagccatca                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
gcatttgact ggaacacgcc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
ctggtggtca gcaggttgtg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
cgtagcgact ccgaagatca                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Primer

<400> SEQUENCE: 36
agcgtacagc gcagaaaaca                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
ccaagcaggc acacacaatg                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Primer

<400> SEQUENCE: 38
gttcgttcct cggagtgagg                                               20

<210> SEQ ID NO 39
```

```
<211> LENGTH: 22
<212> TYPE: DNA
<213> ORGANISM: Artificial Sequence
<220> FEATURE:
<223> OTHER INFORMATION: Synthetic Primer

<400> SEQUENCE: 39
acagttggca caatagacgt tt                                                  22

<210> SEQ ID NO 40
<211> LENGTH: 21
<212> TYPE: DNA
<213> ORGANISM: Artificial Sequence
<220> FEATURE:
<223> OTHER INFORMATION: Synthetic Primer

<400> SEQUENCE: 40
cttccatttc agtgttgcag a                                                   21

<210> SEQ ID NO 41
<211> LENGTH: 20
<212> TYPE: DNA
<213> ORGANISM: Artificial Sequence
<220> FEATURE:
<223> OTHER INFORMATION: Synthetic Primer

<400> SEQUENCE: 41
gctggagtct tgtcaggcat                                                     20

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
gccgctcaca ccatctctta                                                     20

<210> SEQ ID NO 43
<211> LENGTH: 20
<212> TYPE: DNA
<213> ORGANISM: Artificial Sequence
<220> FEATURE:
<223> OTHER INFORMATION: Synthetic Primer

<400> SEQUENCE: 43
tgggagaagt tgagtcgtgc                                                     20

<210> SEQ ID NO 44
<211> LENGTH: 21
<212> TYPE: DNA
<213> ORGANISM: Artificial Sequence
<220> FEATURE:
<223> OTHER INFORMATION: Synthetic Primer

<400> SEQUENCE: 44
catggactcc ctcttccagt c                                                   21

<210> SEQ ID NO 45
<211> LENGTH: 20
<212> TYPE: DNA
<213> ORGANISM: Artificial Sequence
<220> FEATURE:
<223> OTHER INFORMATION: Synthetic Primer

<400> SEQUENCE: 45
```
gatgaaggac accgatcaca                                             20

<210> SEQ ID NO 46
<211> LENGTH: 20
<212> TYPE: DNA
<213> ORGANISM: Artificial Sequence
<220> FEATURE:
<223> OTHER INFORMATION: Synthetic Primer

<400> SEQUENCE: 46
tgctacctgc cacaggagtc                                             20

<210> SEQ ID NO 47
<211> LENGTH: 22
<212> TYPE: DNA
<213> ORGANISM: Artificial Sequence
<220> FEATURE:
<223> OTHER INFORMATION: Synthetic Primer

<400> SEQUENCE: 47
gactcaaaca gtggcttgat ga                                          22

<210> SEQ ID NO 48
<211> LENGTH: 20
<212> TYPE: DNA
<213> ORGANISM: Artificial Sequence
<220> FEATURE:
<223> OTHER INFORMATION: Synthetic Primer

<400> SEQUENCE: 48
cagcatcgat ccgacactca                                             20

<210> SEQ ID NO 49
<211> LENGTH: 20
<212> TYPE: DNA
<213> ORGANISM: Artificial Sequence
<220> FEATURE:
<223> OTHER INFORMATION: Synthetic Primer

<400> SEQUENCE: 49
cggatcttgt cccggcatag                                             20

<210> SEQ ID NO 50
<211> LENGTH: 17
<212> TYPE: DNA
<213> ORGANISM: Artificial Sequence
<220> FEATURE:
<223> OTHER INFORMATION: Synthetic Primer

<400> SEQUENCE: 50
agttcgtgga aggcaat                                                17

<210> SEQ ID NO 51
<211> LENGTH: 17
<212> TYPE: DNA
<213> ORGANISM: Artificial Sequence
<220> FEATURE:
<223> OTHER INFORMATION: Synthetic Primer

<400> SEQUENCE: 51
gtgagagcca gccaaca                                                17

<210> SEQ ID NO 52
<211> LENGTH: 20
<212> TYPE: DNA

```
<213> ORGANISM: Artificial Sequence
<220> FEATURE:
<223> OTHER INFORMATION: Synthetic Primer

<400> SEQUENCE: 52
ccaagctgga gtacgtctgg                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Primer

<400> SEQUENCE: 53
cagagcgctg gtcatgtagt                                              20

<210> SEQ ID NO 54
<211> LENGTH: 23
<212> TYPE: DNA
<213> ORGANISM: Artificial Sequence
<220> FEATURE:
<223> OTHER INFORMATION: Synthetic Primer

<400> SEQUENCE: 54
gtctcagcag tgcaaacaga ctt                                          23

<210> SEQ ID NO 55
<211> LENGTH: 22
<212> TYPE: DNA
<213> ORGANISM: Artificial Sequence
<220> FEATURE:
<223> OTHER INFORMATION: Synthetic Primer

<400> SEQUENCE: 55
gctcgaagcc gaacttgtac tc                                           22

<210> SEQ ID NO 56
<211> LENGTH: 23
<212> TYPE: DNA
<213> ORGANISM: Artificial Sequence
<220> FEATURE:
<223> OTHER INFORMATION: Synthetic Primer

<400> SEQUENCE: 56
tggaagtcca actacttcct caa                                          23

<210> SEQ ID NO 57
<211> LENGTH: 21
<212> TYPE: DNA
<213> ORGANISM: Artificial Sequence
<220> FEATURE:
<223> OTHER INFORMATION: Synthetic Primer

<400> SEQUENCE: 57
atctgctgca tctgcttgga g                                            21

<210> SEQ ID NO 58
<211> LENGTH: 18
<212> TYPE: DNA
<213> ORGANISM: Artificial Sequence
<220> FEATURE:
<223> OTHER INFORMATION: Synthetic Primer

<400> SEQUENCE: 58
ccgggcagcc aatgggag                                                18
```

<210> SEQ ID NO 59
<211> LENGTH: 20
<212> TYPE: DNA
<213> ORGANISM: Artificial Sequence
<220> FEATURE:
<223> OTHER INFORMATION: Synthetic Primer

<400> SEQUENCE: 59
gcaggaggcg gaaacgtctc                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic Primer

<400> SEQUENCE: 60
cggagataac cctgttccgc                                               20

<210> SEQ ID NO 61
<211> LENGTH: 19
<212> TYPE: DNA
<213> ORGANISM: Artificial Sequence
<220> FEATURE:
<223> OTHER INFORMATION: Synthetic Primer

<400> SEQUENCE: 61
caggccgttt actggctga                                                19

<210> SEQ ID NO 62
<211> LENGTH: 21
<212> TYPE: DNA
<213> ORGANISM: Artificial Sequence
<220> FEATURE:
<223> OTHER INFORMATION: Synthetic Primer

<400> SEQUENCE: 62
ctatcggatg gtcagcttca a                                             21

<210> SEQ ID NO 63
<211> LENGTH: 22
<212> TYPE: DNA
<213> ORGANISM: Artificial Sequence
<220> FEATURE:
<223> OTHER INFORMATION: Synthetic Primer

<400> SEQUENCE: 63
gcactggctt ctcatgttta tc                                            22

<210> SEQ ID NO 64
<211> LENGTH: 20
<212> TYPE: DNA
<213> ORGANISM: Artificial Sequence
<220> FEATURE:
<223> OTHER INFORMATION: Synthetic Primer

<400> SEQUENCE: 64
gcctggtaaa caagggccaa                                               20

<210> SEQ ID NO 65
<211> LENGTH: 20
<212> TYPE: DNA
<213> ORGANISM: Artificial Sequence
<220> FEATURE:

<223> OTHER INFORMATION: Synthetic Primer

<400> SEQUENCE: 65
gctgccggaa acggcttata					20

<210> SEQ ID NO 66
<211> LENGTH: 20
<212> TYPE: DNA
<213> ORGANISM: Artificial Sequence
<220> FEATURE:
<223> OTHER INFORMATION: Synthetic Primer

<400> SEQUENCE: 66
gatccaggct ctgcagacag					20

<210> SEQ ID NO 67
<211> LENGTH: 21
<212> TYPE: DNA
<213> ORGANISM: Artificial Sequence
<220> FEATURE:
<223> OTHER INFORMATION: Synthetic Primer

<400> SEQUENCE: 67
cagctagcat ctctcttgcc a					21

<210> SEQ ID NO 68
<211> LENGTH: 22
<212> TYPE: DNA
<213> ORGANISM: Artificial Sequence
<220> FEATURE:
<223> OTHER INFORMATION: Synthetic Primer

<400> SEQUENCE: 68
tgcatacaga cttggtgaat ag				22

<210> SEQ ID NO 69
<211> LENGTH: 22
<212> TYPE: DNA
<213> ORGANISM: Artificial Sequence
<220> FEATURE:
<223> OTHER INFORMATION: Synthetic Primer

<400> SEQUENCE: 69
gaacagtgtg aagactccta tg				22

<210> SEQ ID NO 70
<211> LENGTH: 20
<212> TYPE: DNA
<213> ORGANISM: Artificial Sequence
<220> FEATURE:
<223> OTHER INFORMATION: Synthetic Primer

<400> SEQUENCE: 70
gctaggagca ccagcatcat					20